(12) United States Patent
Alvarez Cordero et al.

(10) Patent No.: US 12,232,990 B2
(45) Date of Patent: Feb. 25, 2025

(54) STENTS WITH INCREASED FLEXIBILITY

(71) Applicant: Sintra Medical LLC, Miami, FL (US)

(72) Inventors: Carlos Gabriel Alvarez Cordero, Monterrey (MX); Ernesto Lorenzo Bonet, Monterrey (MX)

(73) Assignee: Sintra Medical LLC, Miami, FL (US)

( * ) Notice: Subject to any disclaimer, the term of this patent is extended or adjusted under 35 U.S.C. 154(b) by 0 days.

(21) Appl. No.: 18/158,445

(22) Filed: Jan. 23, 2023

(65) Prior Publication Data

US 2023/0157807 A1 May 25, 2023

Related U.S. Application Data

(63) Continuation of application No. 17/575,595, filed on Jan. 13, 2022, now abandoned, which is a continuation of application No. PCT/US2020/042409, filed on Jul. 16, 2020.

(60) Provisional application No. 62/874,890, filed on Jul. 16, 2019.

(51) Int. Cl.
*A61F 2/915* (2013.01)
*A61F 2/07* (2013.01)
*A61F 2/82* (2013.01)

(52) U.S. Cl.
CPC .............. *A61F 2/915* (2013.01); *A61F 2/07* (2013.01); *A61F 2002/072* (2013.01); *A61F 2002/077* (2013.01); *A61F 2002/828* (2013.01); *A61F 2002/91541* (2013.01); *A61F 2002/91566* (2013.01); *A61F 2002/91575* (2013.01); *A61F 2230/0045* (2013.01)

(58) Field of Classification Search
None
See application file for complete search history.

(56) References Cited

U.S. PATENT DOCUMENTS

| 5,913,895 A | 6/1999 | Burpee et al. |
|---|---|---|
| 6,258,116 B1 | 7/2001 | Hojeibane |
| 8,562,665 B2 * | 10/2013 | Jang ..................... A61F 2/91 606/198 |

(Continued)

FOREIGN PATENT DOCUMENTS

| EP | 1151730 B1 | 1/2007 |
|---|---|---|
| EP | 2638882 A1 | 9/2013 |

(Continued)

*Primary Examiner* — Rebecca S Preston
(74) *Attorney, Agent, or Firm* — Shay Glenn LLP

(57) ABSTRACT

Stents that are adapted to be balloon-expanded and include a plurality of rings of repeating cells, wherein adjacent rings are connected by s-shaped or omega-shaped crosslink connectors or a combination of both connectors. The configurations, materials, and/or dimensions of these devices, including the unit cells and/or crosslink connectors allow the stents to be expanded to a greater extent (e.g., up to or greater than 12 mm of diameter), and optionally with reduced foreshortening and without increasing the strain on the materials forming the crosslink connectors and unit cells. The biphasic arrangement of trapezoidal unit cells, as well as the configuration and arrangement of the s-shaped connectors, may allow these stents to expand while maintaining their radial compression strength and longitudinal compression strength with minimal recoil and stent foreshortening.

22 Claims, 39 Drawing Sheets

(56) References Cited

U.S. PATENT DOCUMENTS

| | | | |
|---|---|---|---|
| 11,389,312 B2 | 7/2022 | Alvarez et al. | |
| 2001/0000043 A1* | 3/2001 | Israel | A61F 2/91 606/198 |
| 2002/0007212 A1* | 1/2002 | Brown | A61F 2/89 623/1.16 |
| 2002/0013616 A1* | 1/2002 | Carter | A61F 2/07 623/1.15 |
| 2002/0133224 A1* | 9/2002 | Bajgar | A61L 31/16 623/1.39 |
| 2002/0161429 A1* | 10/2002 | Jang | A61F 2/915 623/1.15 |
| 2002/0165605 A1 | 11/2002 | Penn et al. | |
| 2003/0125800 A1 | 7/2003 | Shulze et al. | |
| 2004/0204751 A1* | 10/2004 | Fischell | A61F 2/91 623/1.34 |
| 2005/0080479 A1* | 4/2005 | Feng | A61F 2/91 623/1.15 |
| 2006/0058870 A1 | 3/2006 | Iki et al. | |
| 2006/0095113 A1 | 5/2006 | Niermann | |
| 2007/0225796 A1* | 9/2007 | Yadin | A61F 2/856 623/1.16 |
| 2007/0255391 A1* | 11/2007 | Hojeibane | A61F 2/915 623/1.15 |
| 2009/0036974 A1* | 2/2009 | Penn | A61F 2/915 623/1.17 |
| 2009/0105809 A1 | 4/2009 | Lee et al. | |
| 2010/0131044 A1* | 5/2010 | Patel | A61F 2/915 623/1.16 |
| 2011/0190861 A1 | 8/2011 | Pericevic et al. | |
| 2011/0238157 A1 | 9/2011 | Li et al. | |
| 2012/0310363 A1 | 12/2012 | Gill et al. | |
| 2013/0178928 A1 | 7/2013 | Vyas et al. | |
| 2014/0277383 A1* | 9/2014 | Sachar | A61F 2/915 623/1.16 |
| 2022/0133464 A1 | 5/2022 | Alvarez Cordero et al. | |

FOREIGN PATENT DOCUMENTS

| | | |
|---|---|---|
| EP | 2881089 A1 | 6/2015 |
| WO | WO2011/032526 A1 | 3/2011 |
| WO | WO2014/176361 A1 | 10/2014 |

* cited by examiner

Stent Graft 5 x 18 mm
| | |
|---|---|
| Initial length | 17.95 mm |
| Initial diameter | 2.107 mm |
| Final diameter with balloon | 5.490 mm |
| Final diameter 30s after balloon removed | 5.007 mm |
| Final length | 17.70 mm |
| Recoil (%) | 8.8% |
| Foreshortening (%) | 1.4% |

FIG. 18A

Stent Graft 5 x 38 mm
| | |
|---|---|
| Initial length | 38.06 mm |
| Initial diameter | 2.217 mm |
| Final diameter with balloon | 5.210 mm |
| Final diameter 30s after balloon removed | 4.900 mm |
| Final length | 37.73 mm |
| Recoil (%) | 5.9 % |
| Foreshortening (%) | 0.87 % |

FIG. 18B

Stent Graft 6 x 18 mm
| | |
|---|---|
| Initial length | 17.62 mm |
| Initial diameter | 2.207 mm |
| Final diameter with balloon | 5.747 mm |
| Final diameter 30s after balloon removed | 5.303 mm |
| Final length | 17.11 mm |
| Recoil (%) | 7.7 % |
| Foreshortening (%) | 2.9 % |

FIG. 18C

Stent Graft 6 x 38 mm
| | |
|---|---|
| Initial length | 37.81 mm |
| Initial diameter | 2.357 mm |
| Final diameter with balloon | 6.277 mm |
| Final diameter 30s after balloon removed | 5.907 mm |
| Final length | 35.83 mm |
| Recoil (%) | 5.9 % |
| Foreshortening (%) | 5.2 % |

FIG. 18D

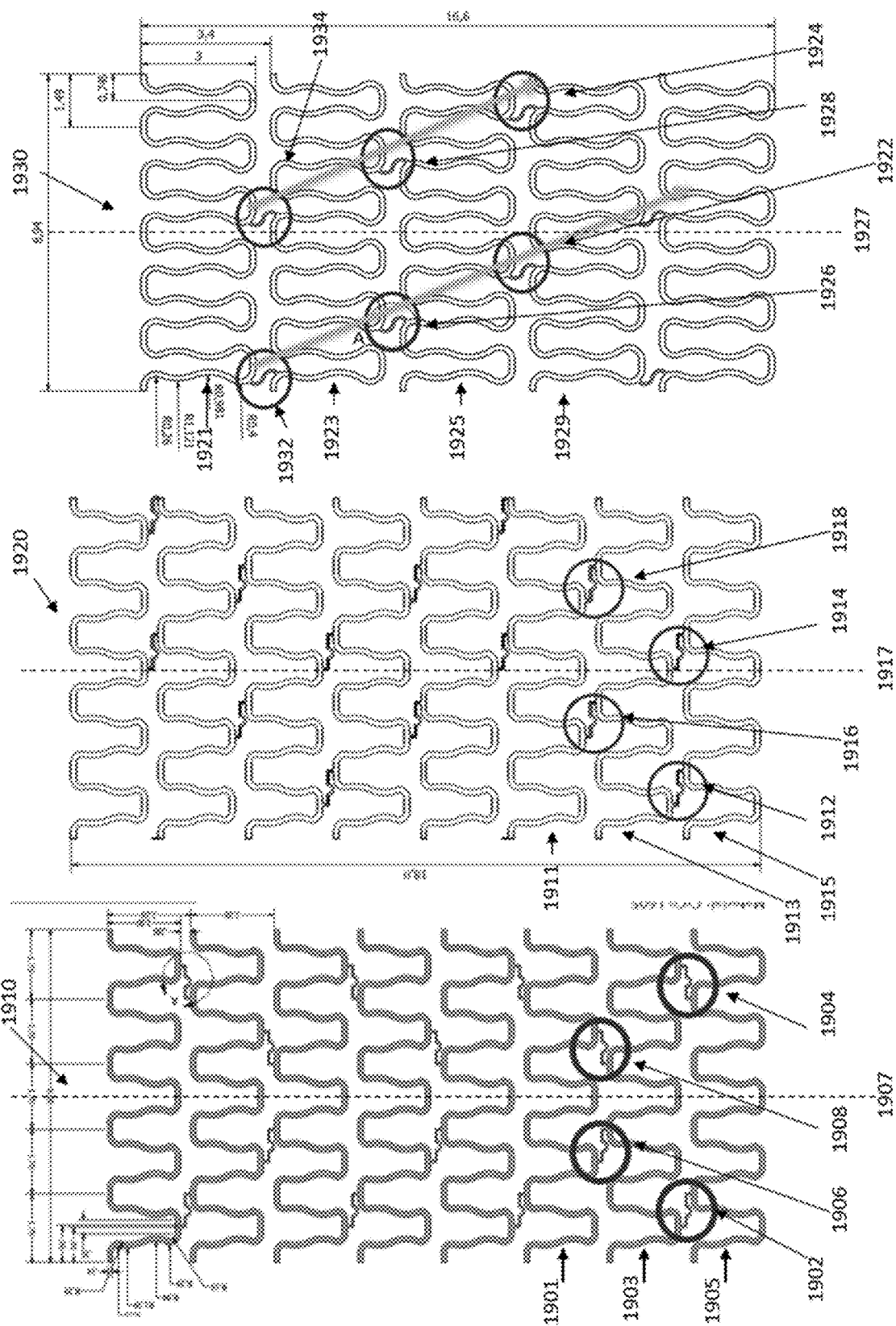

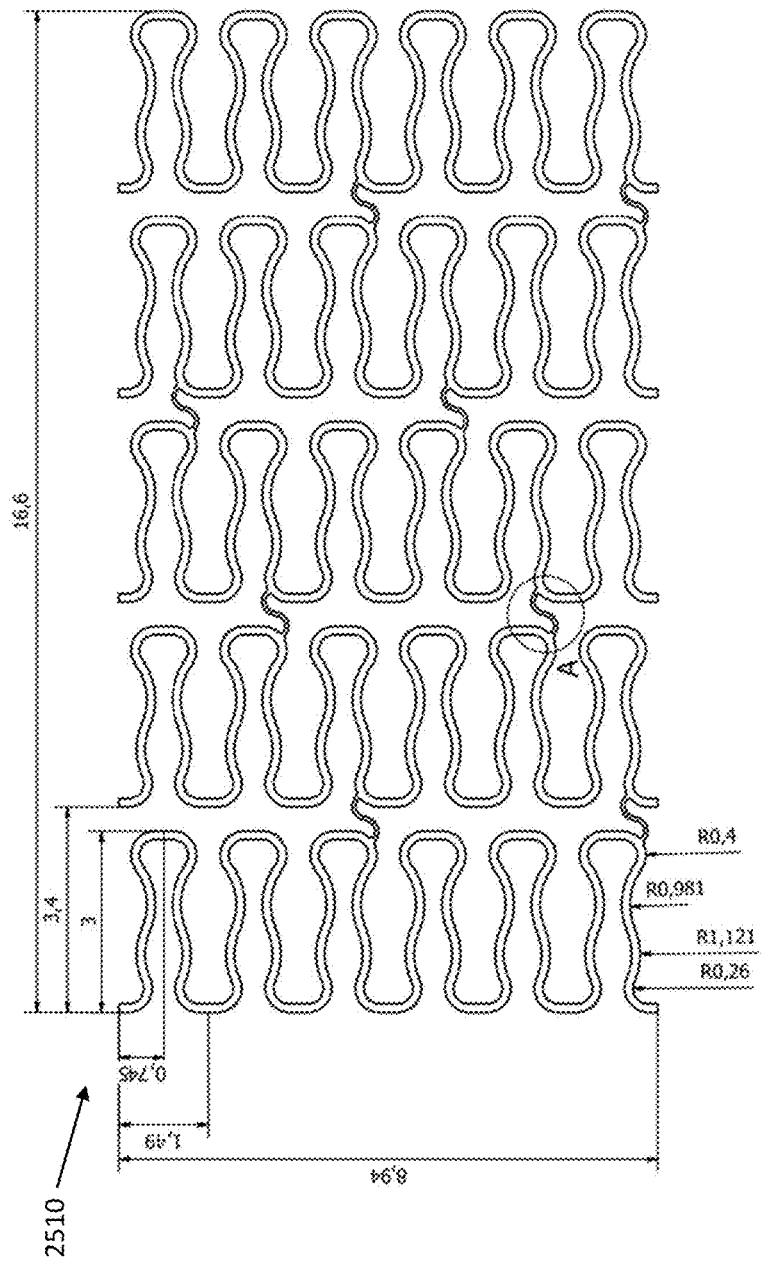
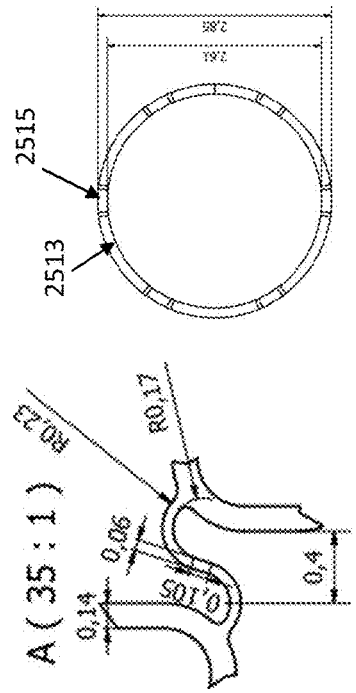
FIG. 25A
FIG. 25B
FIG. 25C

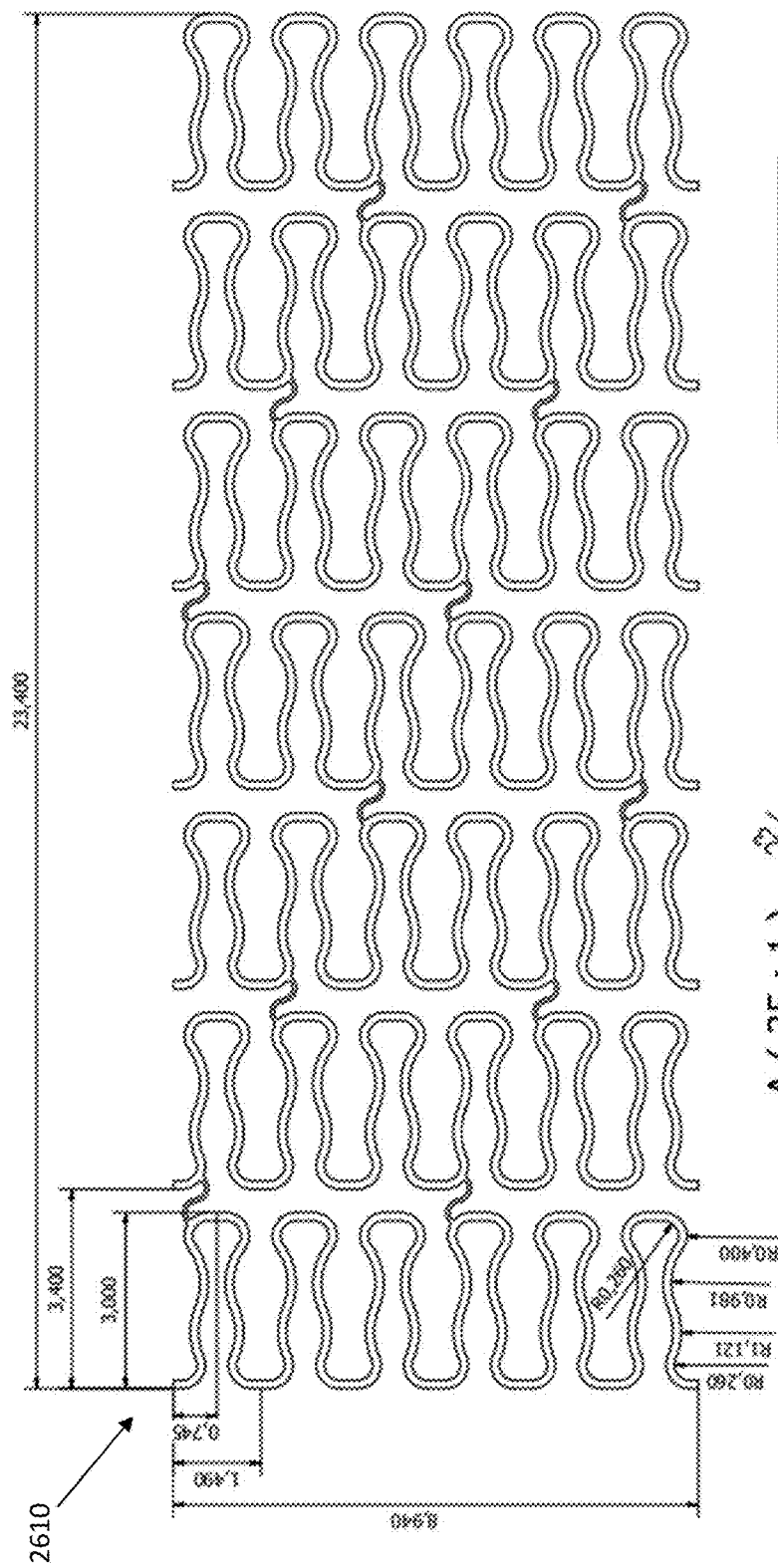
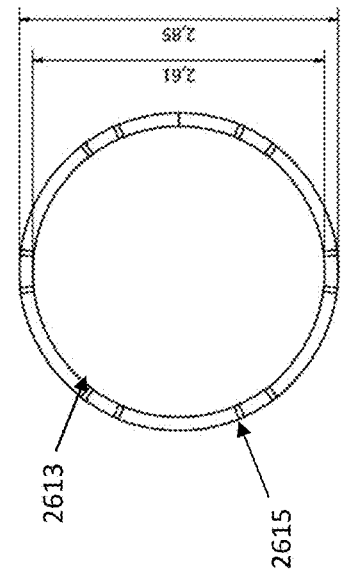
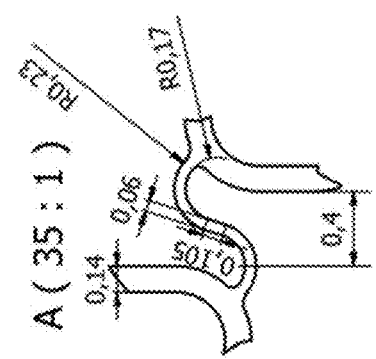
FIG. 26A
FIG. 26B
FIG. 26C

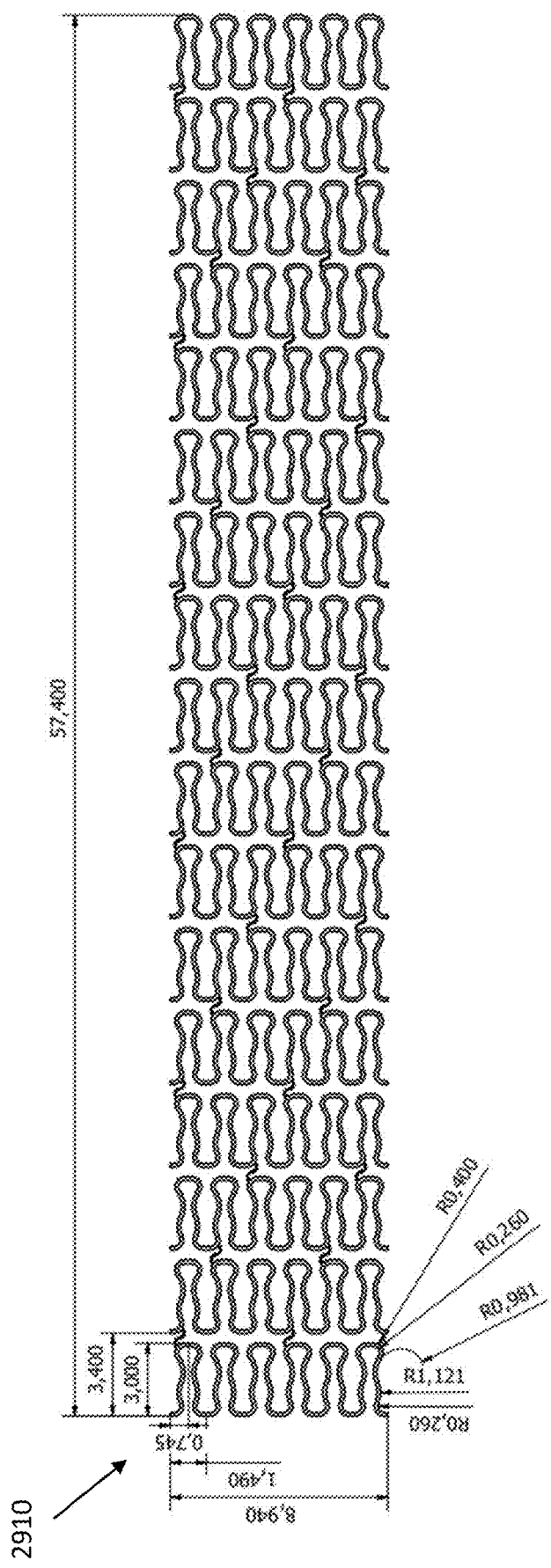
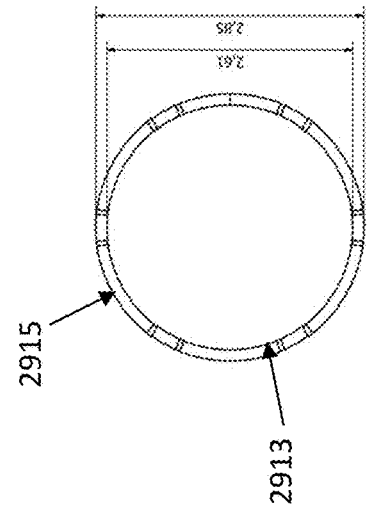
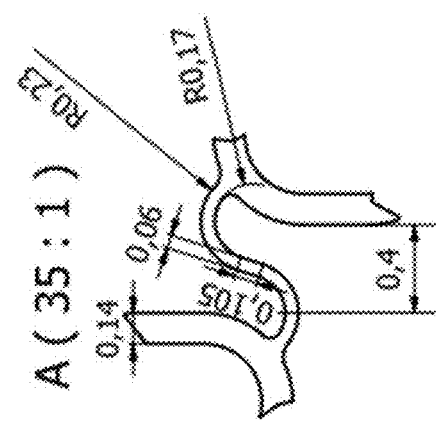
FIG. 29A
FIG. 29B
FIG. 29C

| Data | N total | Mean | Standard Deviation | Sum | Minimum | Median | Maximum |
|---|---|---|---|---|---|---|---|
| | | | Crimped Test Descriptive Statistics [mm] | | | | |
| 5x18 | 3.00 | 1.80 | 0.06 | 5.40 | 1.73 | 1.82 | 1.85 |
| 8x38 | 3.00 | 1.91 | 0.04 | 5.73 | 1.87 | 1.91 | 1.95 |
| 10x58 | 3.00 | 2.07 | 0.08 | 6.20 | 1.98 | 2.10 | 2.12 |

STENTS WITH INCREASED FLEXIBILITY

PRIORITY CLAIM

This application is a continuation of U.S. patent application Ser. No. 17/575,595, filed Jan. 13, 2022, titled "STENTS WITH INCREASED FLEXIBILITY," now U.S. Patent Application Publication No. 2022/0133464, which is a continuation of International Patent Application No. PCT/US2020/042409, filed Jul. 16, 2020, titled "STENTS WITH INCREASED FLEXIBILITY," which claims priority to U.S. Provisional Patent Application No. 62/874,890, titled "STENTS WITH INCREASED FLEXIBILITY" filed on Jul. 16, 2019.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

Described herein are expandable intraluminal grafts ("stents") for use within a body passageway or duct which are particularly useful for repairing blood vessels narrowed or occluded by disease. The stents described herein are configured to change size over a large range, while minimizing the strain on the stent.

BACKGROUND

Intravascular stents may be used in coronary arteries and other body lumens of human patients. Stents are generally tubular-shaped devices which function to hold open a segment of a blood vessel or other body lumen such as a coronary artery. They also are suitable for use to support and hold back a dissected arterial lining that can occlude the fluid passageway. At present, there are numerous commercial stents being marketed throughout the world. For example, prior art stents typically have multiple cylindrical rings connected by one or more connecting links. While some of these stents are flexible and have the appropriate radial rigidity needed to hold open a vessel or artery, there typically is a tradeoff between flexibility and radial strength and the ability to tightly compress or crimp the stent onto a catheter so that it does not move relative to the catheter or dislodge prematurely prior to controlled implantation in a vessel.

Intravascular stents are known and there are numerous structural designs in commercial use. One well known structural pattern includes a tubular stent having rings connected by links. Typically, there are two or more links connecting adjacent rings. While stents having two links between adjacent rings (two-link stents) offer the benefit of low crimp profile and high flexibility, these benefits come with a trade-off in terms of longitudinal stability. Further, peak-to-peak stent patterns (in which the peaks on adjacent rings point toward each other and are essentially axially aligned) offer dense packing of stent rings, which in turn allows for a stent pattern with high radial strength and high radial stiffness. One stent pattern that incorporates these design features is the 2 link offset peak-to-peak style stent. While this stent pattern performs well in terms of traditional stent metrics, it experiences one key tradeoff, namely it will excessively shorten under modest longitudinal compressive loads.

Two-link stents, specifically offset peak-to-peak, where the peaks of adjacent rings point toward each other but are slightly offset circumferentially, excessively shorten under modest (clinically relevant) longitudinal compressive loads. This creates unwanted implications for safety and efficacy of the stent implant. Offset and angled link designs lend readily to collapse behavior, as links do not provide resistance in direction of load, and in addition offset link designs create a bending moment effect, which encourages the bar arms adjacent to link structures to bend and swing excessively (stress is focused in these bar arms).

The methods and apparatuses described herein may be used with and may incorporate features from International Application No. PCT/US2019/013843, filed on Jan. 16, 2019, entitled "STENTS WITH INCREASED FLEXIBILITY," claiming priority to U.S. Provisional Application No. 62/618,007, filed on Jan. 16, 2018, entitled "STENTS WITH INCREASED FLEXIBILITY," each of which is herein incorporated by reference in its entirety.

SUMMARY OF THE DISCLOSURE

The present disclosure relates to stents, such as balloon-expandable vascular prosthesis. In addition to vascular applications, these devices may be used for tracheal, bronchial patency and/or in iliac or renal arteries.

The stents described herein have greater flexibility than prior art stents and expand with less foreshortening, based in part upon a combination of factors, including the configuration of one or more portions of the stent, material properties, and dimensions of one or more portions of the stents.

The stents can include a plurality of annular supports (rings) that are adjacent and extend transversely (e.g., at 90 degrees, but including +/−15 degrees) to the longitudinal distal-to-proximal axis of the device. The rings may be coupled together by one or more crosslink connectors (and in particular, S-shaped crosslink or omega-shaped crosslink, which may also be referred to herein as ring connectors).

At least some of the supports (e.g., rings) may have a configuration that has a repeating pattern (e.g., a biphasic pattern) of a pair of flat-ended, open trapezoidal shapes (which may be rounded at the corners) that are circumferential offset but face each other and may be connected at their ends by connecting members that may be straight or curved (e.g., sigmoid shaped). The trapezoidal shapes may be square, rectangular, isosceles (e.g., a wide-mouthed isosceles in which the open end of the trapezoid would be the longer parallel side, or narrow-mouthed isosceles, in which the open end of the trapezoid would be the shorter parallel side).

Typically, as the stent device is expanded, the flat end of the open trapezoidal shapes stay approximately the same (e.g., same length, and may remain substantially parallel with each other), while the connecting members may bend relative to the flat ends. In some variations, the legs of the open trapezoidal shapes (the legs forming the open ends) may bend relative to the connecting members and/or the flat end(s).

In some variations, the crosslink connectors may be configured as S-shaped connectors, (e.g., the ring connector has an S-shape). An S-shaped ring connector may offer decreased strain when connecting adjacent rings. In some other variations, the crosslink connectors may be configured as omega-shaped crosslink connectors, which may include an arc region (e.g., semi-circular or 180 degree arc, 170 degree arc, 190 degree arc, 200 degree arc, 210 degree arc, etc.) from which a pair of straight legs may extend from either side of the ends of the arc region, e.g., in a single line. For example, each omega-shaped ring connector may include includes an arc region and a pair of linear sections extending from the arc regions on either side of the arc region. One or both ends of the ring connector may be L-shaped. For example, the omega-shaped ring connector may include a first an L-shaped end connecting to the second side of one of the first open trapezoidal portions of the plurality of biphasic cells and a second L-shaped end connecting to the fifth side of one of the second open trapezoidal portions of the plurality of biphasic cells. IN some variations a combination of both s-shaped and omega-shaped connectors may be used in different regions and/or intermixed.

In general, the apparatuses described herein may be configured as balloon-expandable stent grafts that may be used in percutaneous transluminal angioplasty (PTA) procedures, including in particular in peripheral arteries such as tibial, femoral and iliac. Balloon-expandable stents are Endovascular prostheses and may be metallic tubular meshes that expand radially by means of inflation of a balloon. The stent grafts describe here may have a frame (e.g., a cobalt chrome tubular frame/mesh, Nitinol tubular frame/mesh, stainless steel tubular frame/mesh, etc.), embedded into sleeve formed from a polymer matrix. The sleeve may be porous.

For example, this apparatuses and methods described herein relate to stent grafts ("stents") having radiused struts that may be embedded and/or enveloped in a polymer matrix. The stent graft may comprise rings that form radiused struts in sinusoidally ("s-shaped") shaped segments. The rings may be connected by omega-shaped crosslinks, e.g., crosslinks or crosslinks that may have an S-shape or an omega ($\Omega$) shape. The stent struts may be embedded and/or enveloped into a polymer matrix of a composite, such as a composite of PTFE that may enhance its mechanical properties. The improved properties may permit the stent to go through tortuous paths of injured peripheral arteries with the required flexibility and with the proper radial stability to open the vascular vessel and recover the blood flow.

For example, described herein are stent devices having a length extending in a distal to proximal direction, the device comprising: a plurality of adjacent rings arranged transverse to a length of the device, wherein each ring is a ring comprising length of material arranged radially around the length of the stent device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and a plurality of crosslink (e.g., omega-shaped and/or S-shaped) connecting each ring that is adjacent to a more distal ring, wherein in some variations each ring connector connects the second side of one of the first open trapezoidal portions of the plurality of biphasic cells in the ring that is adjacent to the more distal ring to the fifth side of one of the second open trapezoidal portions of the plurality of biphasic cells of the more distal ring; wherein the stent device has a first configuration in which the plurality of adjacent rings have a first diameter, and the stent device has a second configuration in which the plurality of adjacent rings have a second diameter that is greater than the first diameter, and wherein the second side and the fifth side remain parallel as the stent device is expanded from the first configuration to the second configuration. Each of the plurality of rings and a respective subset of the plurality of crosslinks connecting each ring to a more distal ring may be referred to as a connecting portion. The respective subset of the plurality of crosslink connectors of a first connecting portion may be aligned diagonally with a respective subset of the plurality of crosslink connectors in and adjacent connecting portion.

In some variations, each of the crosslink connectors (e.g., S-shaped crosslink connectors) may connect between a second and third sides of one of a first open trapezoidal portions of a plurality of biphasic cells in a first ring that is proximally adjacent to a more distal ring and may connect between a fourth and a fifth side of one of the second open trapezoidal portions of the plurality of biphasic cells of the more distal ring.

Each of a first subset of crosslink connectors of a first connecting portion may be radially offset from a respective one of a second subset of crosslink connectors of a second connecting portion that is adjacent to the first connecting portion. The subset of crosslink of a connecting portion, connected to the flattened tops of the ring of the connecting portion, may not be connected to adjacent flattened tops of the ring.

In general, as described herein, an S-shape may refer to a double-curved shape, having an inflection point at about (e.g., near) the midpoint of the curve with curved regions extending in opposite directions of curvature on either side of the inflection point. The curved regions on either side may be symmetric (e.g., may have radiuses of curvature that are the same or nearly the same) or they may be different (e.g., the first curved region may have a radius of curvature that is larger than the second radius of curvature, including larger by between 0.1%-50%, between 0.1%-40%, 0.1% to 30%, 0.1% to 25%, 0.1% to 20%, etc.). This may apply to the unit cell and crosslinks connector design separately.

A stent device having a length extending in a distal to proximal direction may include: a plurality of adjacent rings arranged transverse to a length of the device, wherein each ring is a ring comprising length of material arranged radially around the length of the stent device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the first open trapezoidal portion is radially offset from the second open trapezoidal portion and the third side of the first open trapezoidal portion is connected to the fourth side of the second open trapezoidal portion by a first connector region extending at a first angle relative to the third side, and wherein the first side of the first open trapezoidal portion connects to a sixth side of an adjacent biphasic cell in the ring by a second connector extending at a second angle relative to the first side; and between one and three crosslinks connecting each ring omega-shaped connector connects the second side of one of the first open trapezoidal portions of the plurality of biphasic cells in the ring that is adjacent to the more distal ring to the fifth side of one of the second open trapezoidal portions of the plurality of biphasic cells of the more distal ring, further wherein an omega-shape of each of the omega-shaped connectors connecting the plurality of adjacent rings is oriented in the same distal to proximal direction; wherein the stent device has a first configuration in which a first diameter of the plurality of adjacent rings is between 0.5 mm and 4 mm and a second configuration in which a second diameter of the plurality of adjacent rings is between 2 mm and 12 mm, and wherein the second side and the fifth side remain parallel but the first and second angles change as the stent device expands from the first configuration to the second configuration. Each ring that is adjacent to a more distal ring and the between 1 to 6 crosslinks connected to the flattened tops of the ring is a connecting portion. The respective crosslinks of a first connecting portion are aligned diagonally with respective crosslink connectors in an adjacent more proximal connecting portion.

The between 1 and 6 crosslinks connected to the flattened top of each ring may not be connected to adjacent flattened tops of the ring. The between 1 to 6 crosslinks of a first connecting portion may be radially offset from between 1 to 6 crosslinks of a second connecting portion.

The plurality of crosslink connectors may comprise between 1 and 10 crosslink connectors (e.g., between 1 and 7, between 1 and 6, between 1 and 5 between 1 and 4, between 1 and 3, etc.). In some variations, the plurality of omega-shaped or/and S-Shape connectors has a maximum of 2 crosslink connectors.

Typically, the first open trapezoidal portion (or at least the flattened top of the open trapezoidal portion) is radially offset from the second open trapezoidal portion (e.g., the flattened top of the open trapezoidal portion). This offset may increase as the device transitions from the first (un-expanded configuration) into the second (expanded) configuration, while the flattened top remains essentially the same shape and size. Thus, the radial offset between the first open trapezoidal portion and the second open trapezoidal portion may increase as the stent device transitions from the first configuration to the second configuration.

In general, the length of any of the devices described herein may be between about 10 mm and about 80 mm (e.g., between about 12 mm to about 80 mm, between about 18 mm and about 79 mm, between about 16 mm and 78 mm, e.g., 80 mm or less, 79 mm or less, 78 or less, etc.). The first diameter (e.g., the outer diameter of each ring in the un-expanded configuration) may be between about 0.5 mm and about 4 mm and the second diameter (e.g., the outer diameter of the rings in the expanded configuration) may be between about 2 mm and about 12 mm (e.g., between about 3 mm and about 7 mm, etc.).

The frame (e.g., the length of material) may comprises one or more of: an alloy of chromium cobalt, a nickel titanium alloy (e.g., Nitinol), a stainless steel and a magnesium alloy.

Any of these devices may include a sleeve bonded to and/or encapsulating the frame (e.g., the plurality of connected rings). The sleeve may be a polymeric matrix in which the plurality of rings is encapsulated. For example, the sleeve may be PTFE. The sleeve material may be electrospun onto the frame. The sleeve may comprise a porous material. In some variations, the sleeve may have a thickness of between about 0.05 and 0.5 mm.

In any of the stent devices described herein the crosslink connectors may be oriented so that an —S-shape or an omega-shape (the approximately "Ω" shape) of each of the crosslink connectors connecting the plurality of adjacent rings are all in the same distal to proximal direction, e.g., so that they all face distally or proximally. In some variations, the crosslinks may all be S-shaped crosslink connectors. In some other variations, the crosslink connectors may all be omega-shaped crosslinks. In other variation the crosslink connectors can be a combination of both omega-shaped and S-shaped connectors.

As mentioned above, the first open trapezoidal portion may be an open rectangle, open isosceles trapezoid, etc. The open trapezoidal portions (first and second) may generally include a flattened end with square or rounded corners extending into a pair of legs. The legs forming the open end may be straight or curved (including sinusoidal). The legs may bend as the device expands from the first (un-expanded) to the second (expanded) configuration. In some variations the second open trapezoidal portion may be the same shape as the first open trapezoidal shape, or different. For example, the first and third sides may be parallel and in some variations the fourth and sixth sides are not parallel. The first and second open trapezoidal shapes have opposite open ends that face different each other (e.g., one faces distally while the other faces proximally). Either or both the first open trapezoidal portion and the second open trapezoidal portion may have rounded edges. In general, the trapezoidal shapes may have different sizes and shapes (e.g., the angles between the walls of the shapes may be different (see, e.g., FIGS. 20D and 20E, etc.).

The width of the length of material forming the repeating biphasic cells (the rings) may be constant or it may vary. For example, the width may be between about 0.05 and about 0.5 mm (e.g., between about 0.1 and about 0.3, between about 0.1 and about 0.2, etc.).

The plurality of adjacent rings are typically separated from each other by a ring offset. The crosslink connector (e.g., the S-shaped crosslink connector or omega-shaped crosslink connector) may sit within this ring offset. The ring offset may be a distance of between 0.1 and 1.5 mm (e.g., between about 0.1 mm and about 1.4 mm, between about 0.1 mm and 1.2 mm, etc.) along the distal to proximal length of the stent device. In general, the distal to proximal height of each ring may be between about 0.5 mm and about 4 mm (e.g., between about 0.5 mm and about 3.5 mm, between about 1 mm and about 3 mm, etc.).

The stent devices described herein, because of the dimensions and arrangement of the frame (e.g., the repeating biphasic cell configuration) and the crosslink connectors (e.g., the S-shaped crosslink connectors or the omega-shaped crosslink connectors) may permit the device to have particularly advantageous properties, including resistance to kinking. For example, the stent device may bend at least 90 degrees along its length in the first configuration without kinking. The device may foreshortens less than 8.5% (e.g., less than 8.4%, less than 8.0%, less than 7.5%, less than 6%, less than 5.5%, etc.) when expanding from the first configuration to the second configuration. For example, the device may foreshorten less than 7% (e.g., less than 6%, less than 5.5%, etc.) when the second diameter of the plurality of adjacent rings is greater than 2.9 times the first diameter of the plurality of adjacent rings.

The first open trapezoidal portions of the repeating biphasic cells in each of the rings may be aligned with the first open trapezoidal portions in the other rings along the proximal to distal length of the device. Similarly the second open trapezoidal portion of the repeating biphasic cells may be aligned with each other along the length (proximal to distal) of the device.

The patterns forming the rings may alternatively be described herein as a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoid-shaped connectors so that each flattened top forms part of a proximal facing U-shape and each flattened bottom forms part of a distal facing U-shape. Each flattened top and a portion each of two sigmoid-shaped connectors to which it is attached may form a first open trapezoidal portion having a proximal-facing opening and each flattened bottom and a portion each of two sigmoid-shaped connectors to which it is attached forms a second open trapezoidal portion having a distal-facing opening.

Thus, described herein are stent devices comprising: a plurality of adjacent rings arranged transverse to a length of the device in a proximal to distal direction, wherein each ring comprises a length of material arranged radially around the length of the stent device in a repeating pattern of alternating flattened tops and flattened bottoms, wherein the flattened tops extend transverse to the length of the device and wherein the flattened bottoms extend transverse to the length of the device and further wherein the flattened tops and flattened bottoms are connected by sigmoid-shaped connectors so that each flattened top forms part of a proximal facing U-shape and each flattened bottom forms part of a distal facing U-shape; a plurality of crosslinks connecting each ring that is adjacent to a more distal ring to the more distal ring, wherein each ring connector connects one of the flattened tops the ring that is adjacent to the more distal ring to a flattened bottom of the more distal ring; wherein the stent device has a first configuration in which the plurality of adjacent rings have a first diameter, and the stent device has a second configuration in which the plurality of adjacent rings have a second diameter that is greater than the first diameter, and wherein the flattened tops and the flattened bottoms remain parallel to each other as the stent device is expanded from the first configuration to the second configuration. Each of the plurality of rings and a respective subset of the plurality of crosslink connectors connecting each ring may be in a connecting portion. The respective subset of the plurality of crosslink connectors of a first connecting portion may be aligned diagonally with a respective subset of the plurality of crosslink connectors in an adjacent more proximal connecting portion. In some variations the pattern is an ABAB repeat pattern; an ABCBA repeat pattern, or an ABCABC repeat pattern, etc.

The plurality of crosslink connectors may comprise, for example, between 1 and 10 crosslink connectors in each connecting portion (e.g., between 1 and 3, between 1 and 4, between 1 and 5, between 1 and 6, between 1 and 7, between 1 and 8, between 1 and 9, etc.). The plurality of crosslink connectors may have a maximum of 2 crosslink connectors in each connecting portion. The flattened tops of each ring may be radially offset from the flattened bottoms. The radial offset may increase as the stent device transitions from the first configuration to the second configuration. As mentioned above, a shape of each of the crosslink connectors connecting the plurality of adjacent rings may be oriented in the same proximal to distal direction. Each of the first subsets of crosslink connectors of a first connecting portion may be radially offset from a respective one of the second subset of crosslink connectors of a second connecting portion that is adjacent to the first connecting portion. The respective subset of the plurality of crosslink connectors of a first connecting portion connected to the flattened tops of each ring may not be connected to adjacent flattened tops of the ring. In some examples, all or a subset of the plurality of crosslink connectors of a first connecting portion may connect to the lateral portion of the inferior U-shape in the biphasic unit cell with the opposite lateral of superior U-shape in the biphasic unit cell.

For example, a stent device may include: a plurality of adjacent rings arranged transverse to a length of the device in a proximal to distal direction, wherein each ring comprises a length of material arranged radially around the length of the stent device in a repeating pattern of alternating flattened tops and flattened bottoms, wherein the flattened tops extend transverse to the length of the device and wherein the flattened bottoms extend transverse to the length of the device and further wherein the flattened tops and flattened bottoms may be connected by sigmoid-shaped connectors so that each flattened top forms part of a distal-facing U-shape and each flattened bottom forms part of a proximal-facing U-shape; between one and three crosslinks connecting each ring that is adjacent to a more distal ring to the more distal ring, wherein each ring connector connects one of the flattened tops of the ring that is adjacent to the more distal ring to a flattened bottom of the more distal ring, further wherein a shape of each of the crosslinks is oriented in the same proximal to distal direction; wherein the stent device has a first configuration in which the plurality of adjacent rings have a first diameter, and the stent device has a second configuration in which the plurality of adjacent rings have a second diameter that is greater than the first diameter, and wherein the flattened tops and the flattened bottoms remain parallel to each other and the shape of the sigmoid-shaped connectors extends radially as the stent device is expanded from the first configuration to the second configuration. Each ring that is adjacent to a more distal ring and the between 1 and 3 crosslinks connected to the flattened tops of the ring may comprise a connecting portion. The respective crosslinks of a first connecting portion may be aligned diagonally with respective crosslinks in an adjacent more proximal connecting portion. The respective crosslinks of a first connecting portion may be radially offset from respective crosslinks in an adjacent connecting portion.

As mentioned above, the first diameter may be between 0.5 mm and 4 mm and the second diameter may be between 2 mm and 12 mm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

In FIG. 1C, the dimensions are in mm.

FIG. 2B shows an end view of the stent device of FIG. 2A with exemplary dimensions (in mm) of the inner and outer un-expanded diameters. FIG. 2C is an "unrolled" configuration of the stent device of FIG. 2A, if the device of FIG. 2A were cut along the longitudinal (e.g. proximal to distal) axis and unrolled to be flat.

FIG. 3B is an end vie of the stent device of FIG. 3A. FIG. 3B is an "unrolled" configuration of the stent device of FIG. 3A, if the device of FIG. 3A were cut along the longitudinal (e.g. proximal to distal) axis and unrolled to be flat.

FIG. 9A shows the exemplary biphasic cell configuration in an un-expanded configuration, while FIGS. 9B and 9C show a progressively more expanded configurations.

FIG. 15A is an 8×58 mm stent, FIG. 15B is an 8×59 mm stent, and FIG. 15C is an 8×57 mm stent.

FIG. 16A is an 8×38 mm stent and FIG. 16B is a 10×58 mm stent.

FIGS. 18A-18D are tables illustrating properties of different examples of stents as described herein. FIG. 18A shows initial and final lengths and diameters of a 5×18 mm stent graft apparatus. FIG. 18B shows initial and final lengths and diameters of a 5×38 mm stent graft apparatus. FIG. 18C shows initial and final lengths and diameters of a 6×18 mm stent graft apparatus. FIG. 18D shows initial and final lengths and diameters of a 6×38 mm stent graft apparatus.

FIGS. 19A-19F show different variations of stent apparatuses having different distribution and ring connector shapes.

FIG. 20E shows a skeletonized version of the region, including a unit cell, of FIG. 20D.

FIG. 22A shows an omega-shaped connector while FIG. 22B shows a S-shaped connector.

FIGS. 25A-25C show exemplary dimensions of a stent apparatus according to some embodiments of the disclosure.

FIGS. 26A-26C show exemplary dimensions of a stent apparatus according to some embodiments of the disclosure.

FIGS. 29A-29C show exemplary dimensions of a stent apparatus according to some embodiments of the disclosure.

FIG. 32A shows the average crush resistance (between parallel plates) following ISO 25539 testing, showing an average of between about 3N and about 6.5 N. FIG. 32B is a graph showing a comparison of the radial compression strength (e.g., crush resistance) of the stents as descried herein (indicated by *), and prior art stents.

FIG. 33A shows the average longitudinal stent resistance following ISO 25539 testing. FIG. 33B is a graph showing a comparison of the longitudinal stent resistance (e.g., the force needed to achieve 15% longitudinal compression) between prior art stents and examples of stents as descried herein (indicated by *) having different dimensions.

FIG. 34A is a table showing the results of crimp testing on three different sizes of the stents described herein, e.g., stents having a plurality of adjacent rings formed of alternating flattened tops and flattened bottoms that are transverse to the length of the device and are connected by sigmoid-shaped connectors aligned in a helically winding arrangement around the length of the device. FIG. 34B graphically illustrates a comparison between the results of crimp testing for the stent devices as described herein (e.g., in FIGS. 20A-20E, 21, 22B, 23B, 25A-31C, indicated by an "*" in FIG. 34B) and prior art stent devices.

FIG. 35A is a table showing the results of recoil testing on two different sizes of the stents as described herein, e.g., stents having a plurality of adjacent rings formed of alternating flattened tops and flattened bottoms that are transverse to the length of the device and are connected by sigmoid-shaped connectors aligned in a helically winding arrangement around the length of the device (similar to that shown in FIGS. 20A-20E, 21, 22B, 23B, 25A-31C). FIG. 35B graphically illustrates a comparison between the results of recoil testing for the stent devices as described herein (e.g., in FIGS. 20A-20E, 21, 22B, 23B, 25A-31C, indicated by an "*" in FIG. 35B) and prior art stent devices.

In FIG. 36, the stents examined are similar to those shown in FIGS. 20A-20E, 21, 22B, 23B, 25A-31C (with or without a graft material included). Foreshortening was typically less than about 8.5%.

FIG. 37A shows the stent arranged on a balloon that has been inflated to expand the stent into the second, expanded, configuration. FIG. 37B shows the expanded stent removed from the balloon. FIG. 37C shows the distal end opening of the stent.

DETAILED DESCRIPTION

Described herein are stent apparatuses with improved flexibility for greater expansion without fracture. This allows the stents to be expanded to greater diameter sizes when in use, which provides an exemplary benefit of being able to use a single stent for a greater variety of uses (e.g., different vessel sizes) without having to use a differently sized stent. The stents described herein are also adapted such that foreshortening of the stent during expansion is reduced, preventing a variety of complications.

The stents herein generally have a collapsed delivery configuration, and are adapted to be expanded. The "collapsed" configurations may be referred to herein as delivery, collapsed, initial, or other similar term. The delivery configuration can be the configuration the stent has after being manufactured, such as by laser cutting a tubular element or 3-D printing the stent. The stents herein are described as being expanded by balloon expansion, but the stents could be adapted to be able to at least partially self-expand.

Any of the stents herein can include one or more coverings over any portion of the stent.

The stents include a plurality of supports, optionally annular, wherein each of the plurality of supports are connected to at least one adjacent support by one or more connecting portions, which can include one or more connectors.

There are several factors that influence the flexibility of the stents herein and provide the stents with the ability to expand to larger outer dimensions without fracturing. The following are examples of factors that can influence the flexibility of the stents: the configuration of the annular supports and connectors; the dimensions of the annular supports and connectors; and the materials of the annular supports and connectors.

Figure 1A:
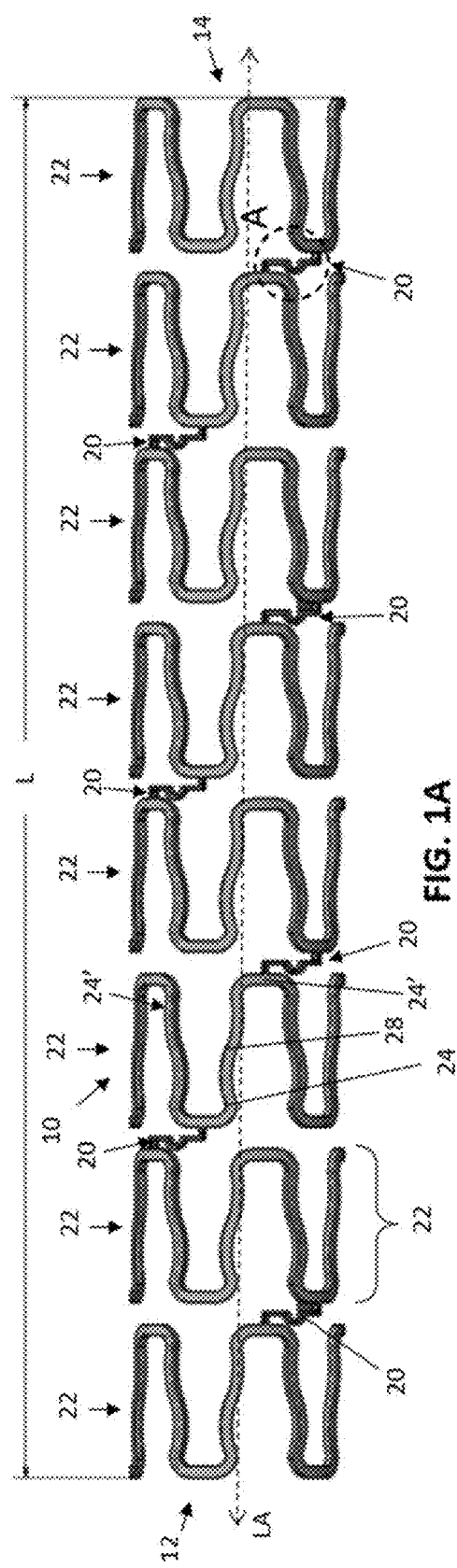
FIG. 1A is a side view illustrating a delivery configuration of an exemplary stent that comprises a plurality of supports coupled together by connecting regions.

FIG. 1A illustrates a side view of exemplary stent 10 in an un-expanded (e.g., delivery) configuration, stent 10 having a first end 12 (e.g., proximal end) and a second end 14 (e.g., distal end) and a length, L; thus stent 10 has a longitudinal axis L extending through a lumen defined by the stent. Stent 10 includes a plurality of annular supports 22 ("rings") transverse to the long axis and generally axially spaced from at each other; the individual regions are connected by at least one crosslink connector 20 (in this example, an omega crosslink connector). In this example, an annular support is "adjacent" to another annular support if it is the next annular support when moving towards either the first end 12 or the second end 14. In this example, the annular supports 22 (which may also be referred to herein as "rings") are connected to at least one adjacent support 22 by a ring connector 20 (i.e., omega connector). The rings 22 may be described herein as being "connected" to adjacent rings; it is understood that this may include one or more (e.g., two) ring connectors 20 that may be integrally formed with the rings, such as if the entire stent may be manufactured from a single piece of starting material, e.g., by laser cutting a cylindrical piece. Each of the rings 22 in this embodiment has a wave configuration, with a plurality of peaks and valleys, repeating in a pattern (only some peaks and valleys are labeled for clarity). In this embodiment, peaks of the supports may extend to the same location along the length of the stent. Valleys of supports (rings) also extend to the same location along the length of the stent. Thus, the peaks (e.g., the flattened top regions 24) may be aligned along the length of the stent device, shown, and the valleys (e.g., the flattened bottom regions 24') may also be aligned along the length of the stent. Peaks and valleys of the waves may define flattened, or squared, ends. Between the peaks and valley are intermediate sections 28 (connecting regions), and in this embodiment the intermediate sections have S-shapes (or may have sigmoid shapes), as can be seen in the side view of FIG. 1A. This embodiment is an example of at least one annular support with a repeating wave pattern having flattened ends connected by curvilinear intermediate sections, such as S-shape intermediate regions. For simplicity of discussion, a repeating unit of a ring and the plurality of crosslinks attached to the flattened tops of the ring can be referred to as a connecting portion. The apparatus thus includes a plurality of connecting portions forming the stent.

In this embodiment, the annular supports all have the same configuration along the length of the stent. Peaks 24 (which are described in additional detail below, and may be referred to herein as a first open trapezoidal portion having a first side, a second side and a third side forming a proximal-facing opening) of adjacent rings may therefore be circumferentially aligned, and valleys (which are described in additional detail below and may be referred to herein as a second open trapezoidal portion having a fourth side, a fifth side and a sixth side) of adjacent rings may be circumferentially aligned.

In alternative embodiments, not every annular support has the same configuration as every other annular support.

Figure 1C:
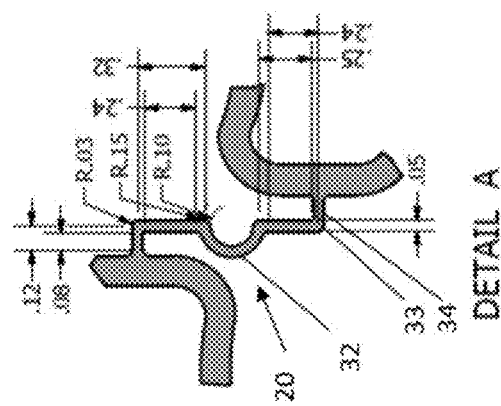
FIG. 1C illustrates a highlighted view of detail of region A shown in FIGS. 1A and 1D. In any of the images and examples provided herein, the dimensions shown are exemplary only, and are intended to provide illustrations of a range of dimensions that may work (e.g., +/− about 50%, 40%, 35%, 30%, 25%, 20%, 15%, 10%, 5%, etc.).
Figure 1B:
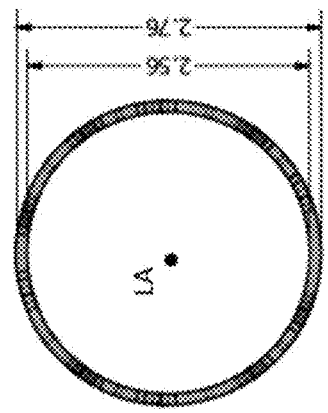
FIG. 1B illustrates an end view of the stent from FIG. 1A.
Figure 1D:
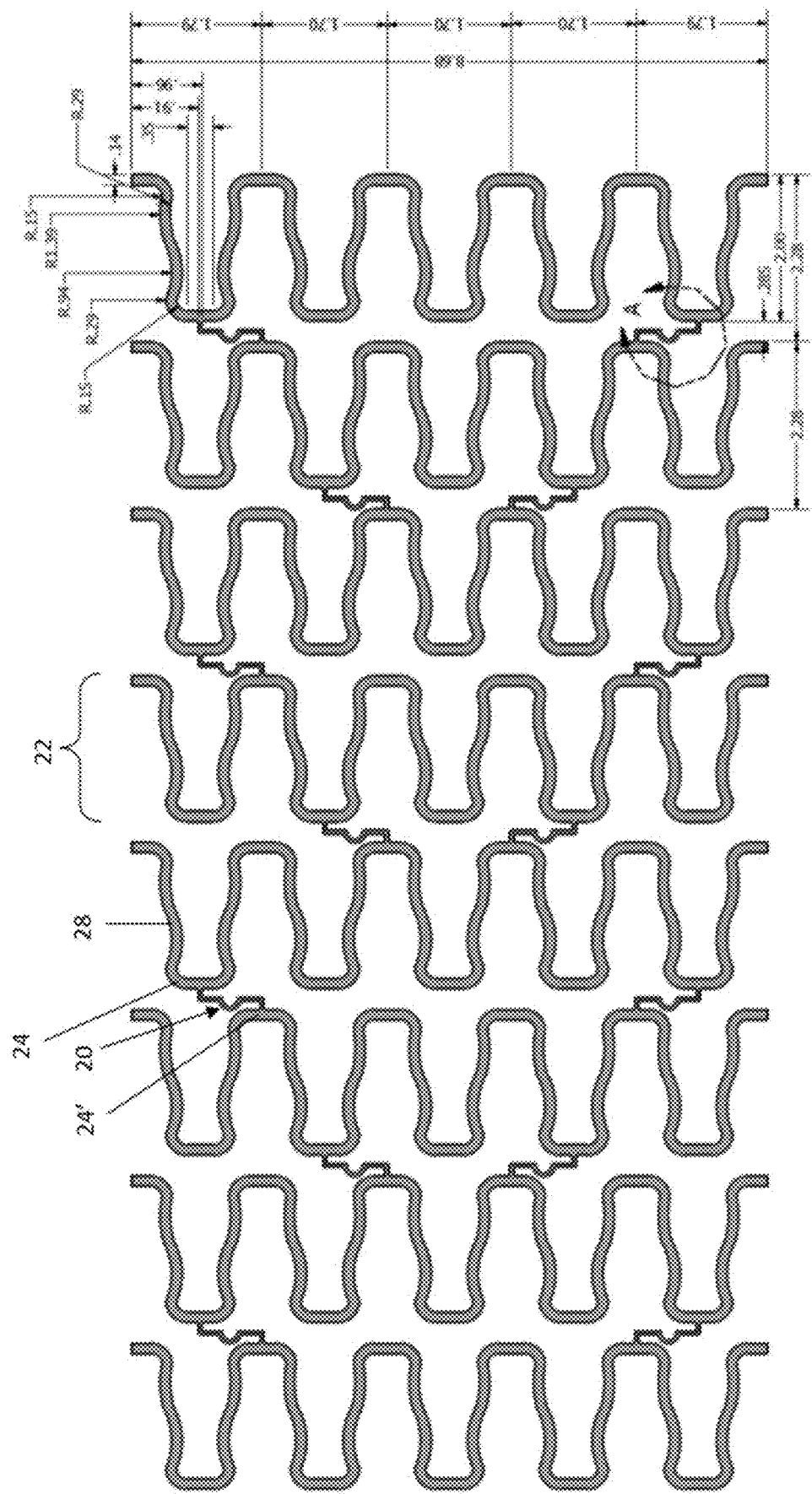
FIG. 1D illustrates the stent from FIG. 1A in a flattened, planar, configuration. Exemplary dimensions (in mm) are shown; as mentioned, the dimensions may be +/− about 50%, 40%, 35%, 30%, 25%, 20%, 15%, 10%, 5%, etc.

Adjacent annular supports 22 are connected together by ring connector 20. FIG. 1D illustrates a flattened/planar view of an example of a stent device 10, which illustrates the connections between adjacent rings. In this embodiment, the crosslink 20 (e.g., omega crosslink between adjacent rings 22 include at least two crosslinks, shown in FIG. 1C as Detail A shown in FIGS. 1A and 1D. FIG. 1C illustrates a ring connector that connects adjacent rings 22 (only a portion of rings are shown). The ring connector has a configuration, at least a portion of which may have a general "omega" configuration. In this embodiment, the general "omega" configuration is defined by arc region (e.g., dome region) 32 and radial regions 33 generally extending radially outward from arc or domed region 32. In this embodiment, radial regions have linear configurations and may be L-shaped, but in other embodiments they could include some curvature. The ring connector (i.e., an omega ring connector) may also include axial regions 34 which may extend generally axially from radial regions 33 and may be parallel to the longitudinal axis LA of the device (e.g., forming the L-shaped ends, mentioned above). Axial regions 33 of the ring connector are linear but could, in some embodiments, have some curvature to them. One of the axial regions 34 extends further toward first end 12 than the other axial region 34. Radial regions of a ring connector may generally be aligned when they have linear configurations (and are also aligned with other radial regions of the other ring connector that connects the two adjacent supports), and axial regions 34 are parallel to each other, and to the longitudinal axis LA.

The "omega" shape is generally defined by an arc or domed region 32 and radial regions 33. While domed region 32 and radial regions 33 do not form an exact, traditional, "omega" Greek letter, it is understood that they form a general "omega" shape of the ring connector. Domed regions 32 and radial sections 33 can have slightly varying configurations and that portion of the ring connector can still have a general "omega" configuration as that term is used herein.

The crosslink extends from a flattened top region (e.g., of the open trapezoidal 'peak' region 24) of a first ring 22 to a flattened top (e.g., of the next open trapezoidal 'valley' region 24') of an adjacent ring 22, as can be seen in FIGS. 1A and 1D. The first open trapezoidal portion (e.g., peak) and second open trapezoidal portion (valley) from which the ring connector extends are not circumferential aligned. For example, a ring connector extends from a first open trapezoidal portion 24 on a first ring 22 to a second open trapezoidal portion 24' on an adjacent ring, as shown in FIGS. 1A, 1C and 1D.

As can be seen in FIG. 1D, the arc regions of all of the omega-shaped crosslink have similar configurations, and are all oriented in the same direction. In this embodiment, each pair of adjacent supports is coupled together by two omega-shaped crosslinks, each of which has the configuration shown in FIG. 1C. As can be seen in FIG. 1D, the omega-shaped crosslink in any given connecting portion are not circumferentially aligned with the crosslink in the adjacent connecting portion, but they are circumferentially aligned with the crosslink in the next adjacent connecting portion. In this embodiment, the position of the omega crosslink are in an A-B-A-B pattern, with every-other ring having crosslink that are circumferentially aligned.

The first and second open trapezoidal potions of the repeating biphasic shapes forming each ring are connected by an intermediate section (e.g., connecting the peak and a valley regions) as described above. In FIG. 1D, the connecting intermediate section is a length that extends in an angle between the open trapezoidal portions; this may be straight or curved (e.g., sinusoidal, including s-shaped). As will be described in greater detail below, this intermediate section, and in some variations the 'legs' of the open trapezoidal portions (forming the openings) may change their angle relative to the flattened top region when the stent devices expand (e.g., when driven by a balloon to expand).

In FIG. 1D, the two omega-shaped crosslink 20 extend from adjacent peaks 24' and 20, on adjacent rings, connecting the two rings. In this embodiment, the two crosslinks extend from adjacent flattened top (or bottom) regions. In the example shown in FIGS. 1A-1D, there are three flattened top regions (peaks) between some of the omega-shaped crosslink (from which no crosslink extends), and one flattened top region (peak) on the other side (radially) between the two omega-shaped connectors. Thus, in the space between each set of rings, two omega-shaped crosslinks connect the adjacent rings, and the connecting pattern is offset and alternating with every other ring, as shown in FIGS. 1A-1D.

In some variations, only three or fewer (e.g., two) crosslink are used to connect adjacent rings. For example, by having only two crosslinks in each space between each set of rings, there is less area of material than in some other stent designs. This smaller area may allow the stent to have more flexibility and can expand to a greater extent when forces are applied on the stent such as by an expansion balloon. In alternative embodiments, however, there could be more than two crosslinks in a connecting portion, and the desired flexibility could still be maintained by modifying one or more other aspects, such as, for example without limitation, one or more dimensions (e.g., thickness, radius), configuration, or material.

In general, each ring may be formed of a length of material, such as a metal (e.g., a nickel titanium alloy, a chromium alloy, a stainless-steel alloy, etc.). The length of material may be a strip of material formed into a rectangular or square cross-section (e.g., which may be formed by laser cutting from a tube of the material), or in some variation it may be formed of a wire.

The dimensions of the rings are one factor that may influence the flexibility and may provide for greater expansion of the stents herein. Less area of the stent material generally increases the flexibility and allows the stent to expand to greater outer dimensions without fracture. FIG. 1D shows exemplary dimensions and radii for portions of at least one of the rings. In some embodiments the thickness of the support material is from 0.05 mm to 2 mm, such as from 0.05 to 1 mm, such as from 0.1 mm to 0.8 mm, such as from 0.06 mm to 0.09 mm (e.g., 0.1 mm, 0.2 mm, 0.3 mm, 0.4 mm, 0.5 mm, 0.6 mm 0.7 mm, 0.8 mm, 0.9 mm, 1 mm).

The configuration of the ring, including the arrangement of the repeating biphasic cells (e.g., the first and second open trapezoidal portions) of the rings is another factor that influences the flexibility and provides for greater expansion of the stents herein. The plurality of adjacent rings (e.g., annular supports) 22 generally have a wave-like configuration, with squared (flattened) end and S-shaped intermediate sections in between these flattened ends (forming peaks and valleys). As shown in the exemplary FIG. 1D, the connecting regions 28 between the open trapezoidal portions (or more specifically, between the flattened tops) are not aligned with the longitudinal axis of the stent. That is, they are at an angle relative to the longitudinal axis. This angle can increase the flexibility of the stent and allow for greater expansion.

As mentioned above, the dimensions of the omega-shaped crosslink connectors are an additional factor influences the flexibility and provides for greater expansion of the stents herein. FIG. 1C shows exemplary dimensions (e.g., thicknesses and radii) that can be used for any of the omega-shaped crosslink connectors described herein. In some embodiments, one or more omega-shaped crosslink connectors has a thickness from about 0.02 mm to about 1 mm, such as about 0.02 mm to about 0.8 mm (e.g., about 0.02 mm about 0.03 mm, about 0.04 mm, about 0.05 mm, about 0.06 mm, about 0.07 mm, about 0.08 mm, etc.).

The configuration and number of the omega-shaped crosslink connectors are other factors that influence the flexibility and provides for greater expansion of the stents herein. As set forth herein, at least a portion of the omega-shaped crosslink connectors may have a general omega configuration, including an arc (e.g., domed) section. The omega configuration provides for added flexibility in the connecting portions. Additionally, in some embodiments the connecting portions only include two omega-shaped crosslinks connectors, which reduces the area of the connecting portions and increases the flexibility.

Figure 1E:
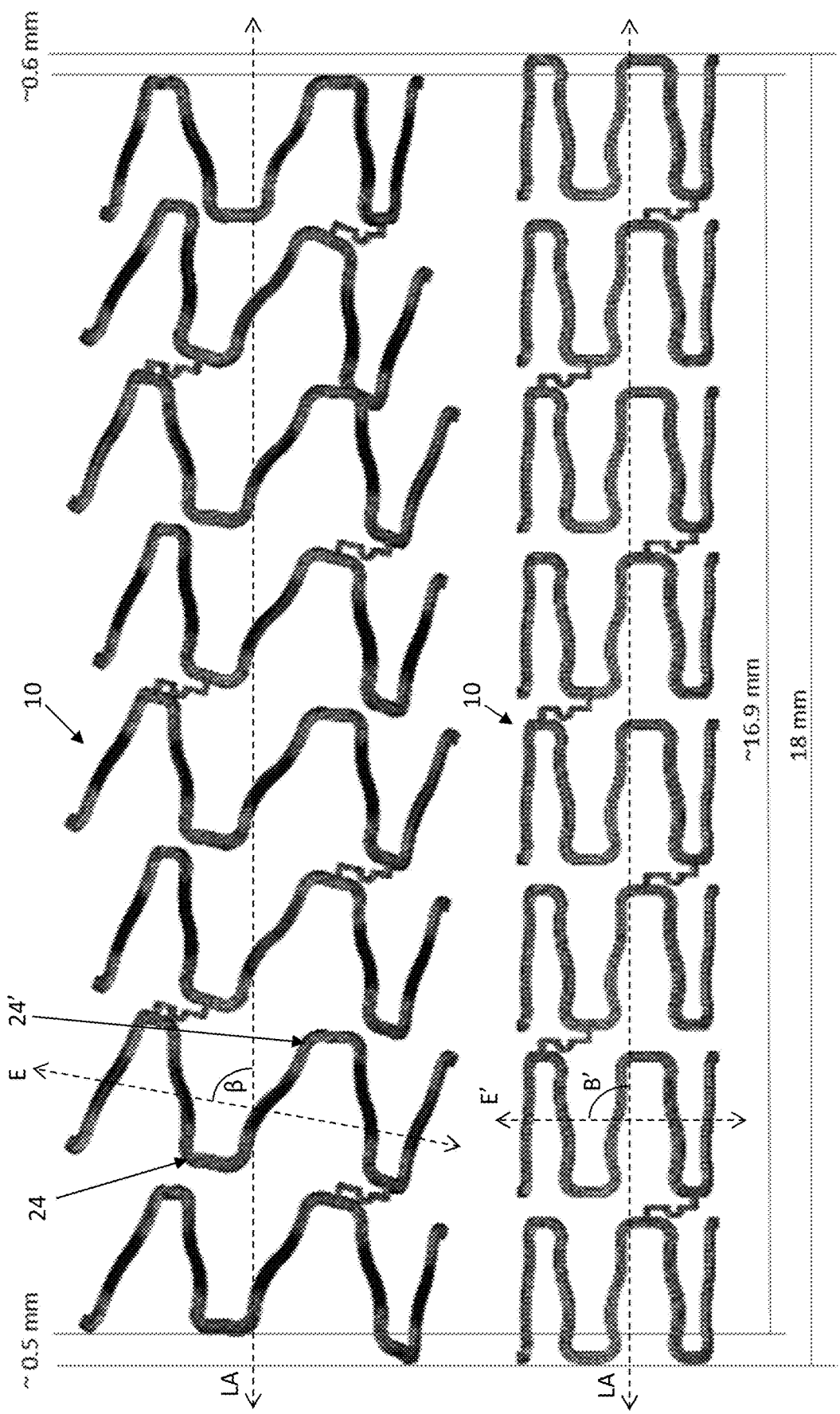
FIG. 1E illustrates the stent from FIG. 1A in an initial (unexpanded, bottom) configuration and an expanded (top) configuration. Shading indicates relative strain on the frame of the stent shown.

FIG. 1E illustrates an expanded configuration (top) of the stent 10 from FIGS. 1A-1D. The bottom configuration in FIG. 1E is the same stent device 10 as shown in FIG. 1A. The top in FIG. 1E illustrates the stent 10 (which has an initial, unexpanded outer diameter of approximately 2.76 mm—see FIG. 1B) expanded to an outer diameter of about 8 mm, about 2.9 times the initial outer dimension. FIG. 1E also illustrates the foreshortening that the stent undergoes as it is expanded. The initial length is 18 mm, and the length when expanded is about 16.9 mm, shortening by about 1.1 mm. In this embodiment the stent foreshortened by not more than about 6.2% when expanded to about 2.9 times an initial outer diameter. The ability to expand this much with so little foreshortening is due in part to the configuration of the rings and omega-shaped crosslink connectors, the dimensions of the rings and omega-shaped crosslink connectors, and the material(s) forming the stent.

As can also be seen in the top view of FIG. 1E, when the stent is expanded, the flattened top of the first open trapezoidal portion (peak) 24 is rotated along the radius of the stent, e.g., away from the longitudinal axis of the stent, with the flattened tops (or bottoms) of the next open trapezoidal portion (valley) 24' also rotated, but still parallel with the first flattened top 24. The plane of each ring is shown rotated by angle ($\beta$) relative to the long axis (LA) compared to the initial configuration shown in the bottom of FIG. 1E, showing the unexpanded configuration. The flattened tops of peaks 24 and may be individually flared radially outward relative to the flattened tops of the valleys 24' when the device is expanded. The angle of rotation can be anywhere from 5 degrees to 60 degrees, such as from 10 to 45 degrees.

As is also shown in the bottom of FIG. 1E, each ring may have an axis or plane E' that is orthogonal to the longitudinal axis (LA). When the stent is expanded, in this example the annular supports (rings) expand in such a manner than the axis rotates with respect to the longitudinal axis, and as shown in the expanded top configuration, the plane of the rings has rotated relative to the longitudinal axis. The angle $\beta$ is less than 90 degrees (compared with the original angle of $\beta'$ which is approximately 90 degrees in this example).

Figure 1F:
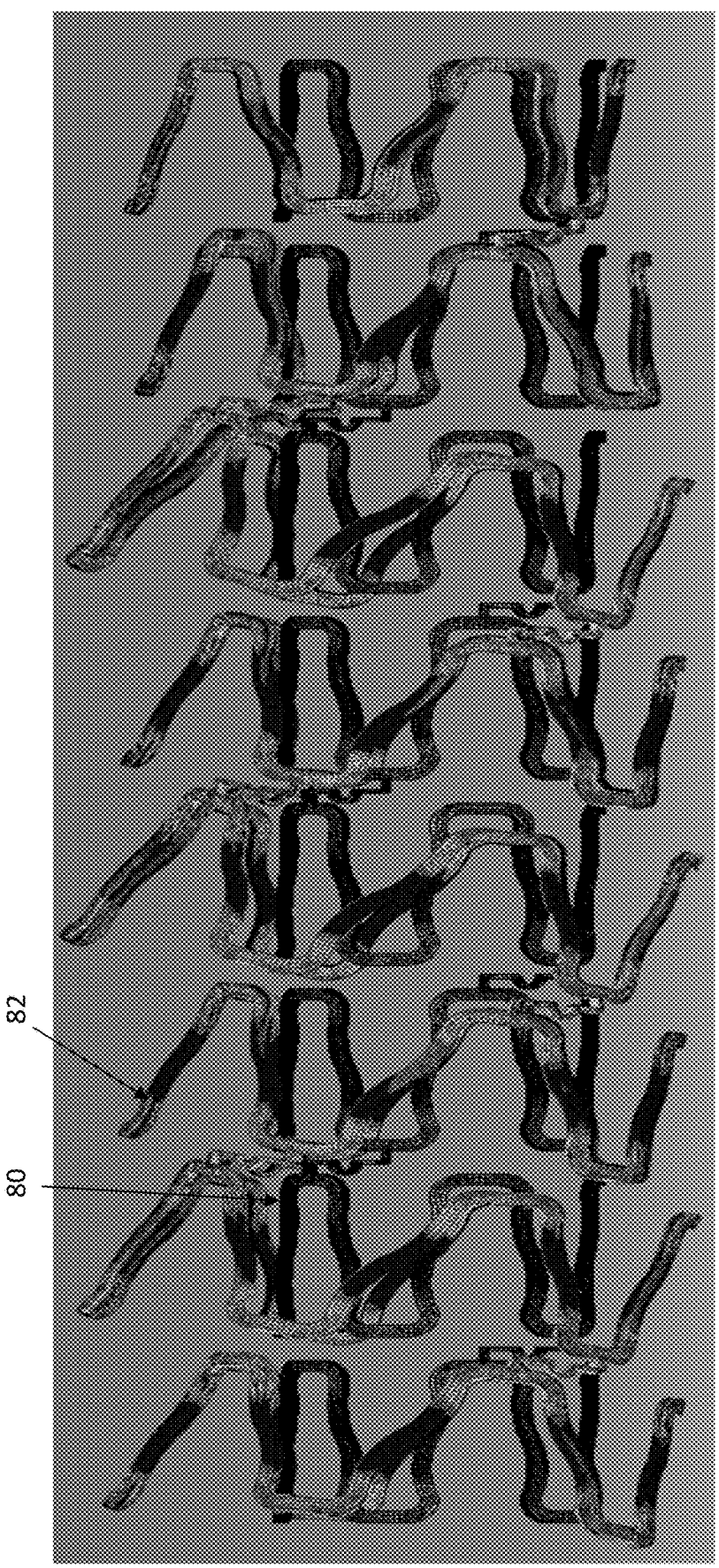
FIG. 1F overlays the two configurations shown side-by-side in FIG. 1E.

FIG. 1F illustrates the initial 80 and expanded 82 configurations from FIG. 1E overlaid on top of each other, which can further highlight the disclosure described with respect to FIG. 1E.

It is understood that not every features show in the embodiments herein is necessary to increase the flexibility of the stents herein. For example, in alternative embodiments, some connecting portions can have three crosslink connectors, and the stent may still be able to expand to desired outer dimensions for some applications.

As set forth above, one of the exemplary advantages of stents herein is that they can be mounted on different diameter expansion balloons and can be expanded to a greater variety of outer dimensions. This can reduce the number of stents that must be available for use for a particular medical application.

Figure 2B:
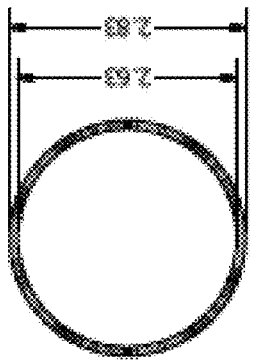
FIGS. 2A-2C illustrate view of an exemplary stent similar to the exemplary stent shown in FIGS. 1A-1F. A side view of the stent is shown in FIG. 2A.
Figure 2A:
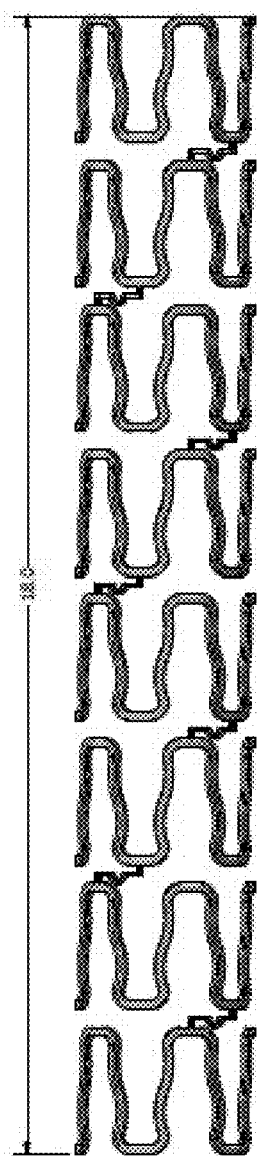
Figure 2C:
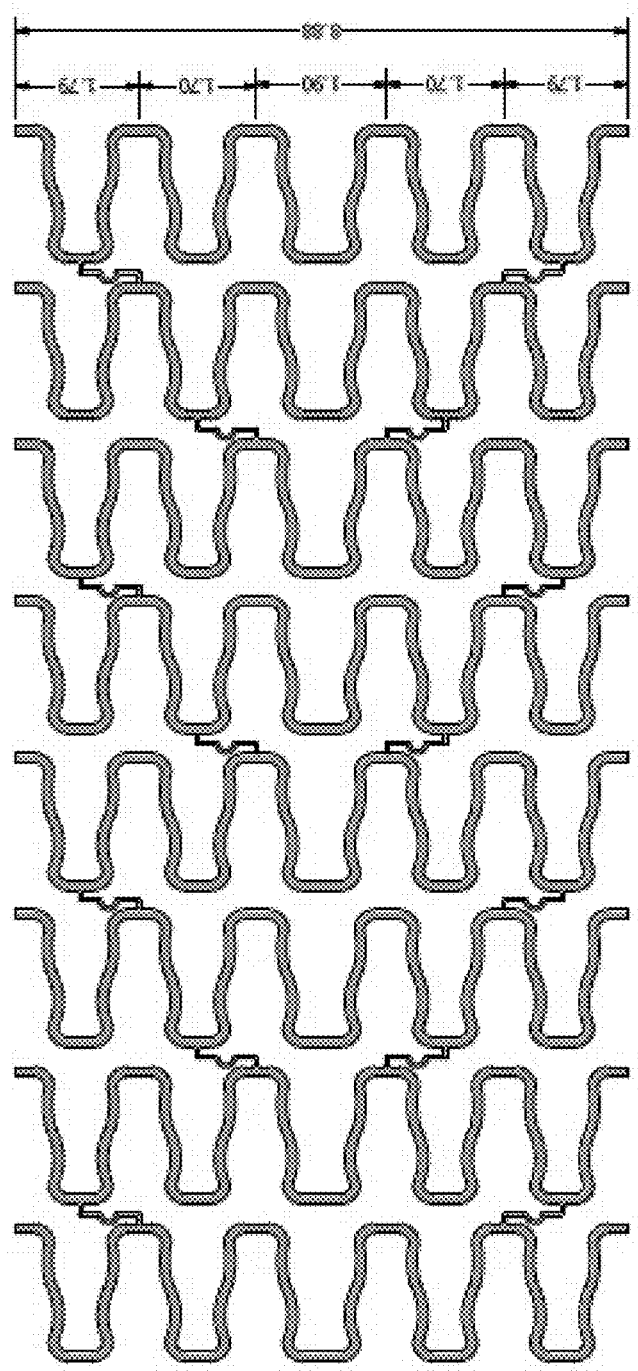

FIGS. 2A-2C illustrate an exemplary stent that is similar in many ways to the exemplary stent in FIGS. 1A-1E. The general configurations of the annular supports and crosslink connectors is the same to those in FIGS. 1A-1E. One difference is that the initial outer dimension of the stent is shown as 2.83 mm (see, e.g., FIG. 2B), as opposed to 2.76 mm in the embodiment in FIG. 1A-1E. The initial larger outer dimension allows the stent in this embodiment to be expanded to larger outer dimensions without fracturing. Another difference is the distance between peaks in one circumferential region of the stent. As shown in FIG. 2C, one distance between the peaks in the center of the stent is 1.90 mm, whereas in FIG. 1A-1E it was 1.70 mm (see FIG. 1D). Any of the other features described with respect to the embodiment in FIGS. 1A-1E can be incorporated in this embodiment as well.

Figure 3A:
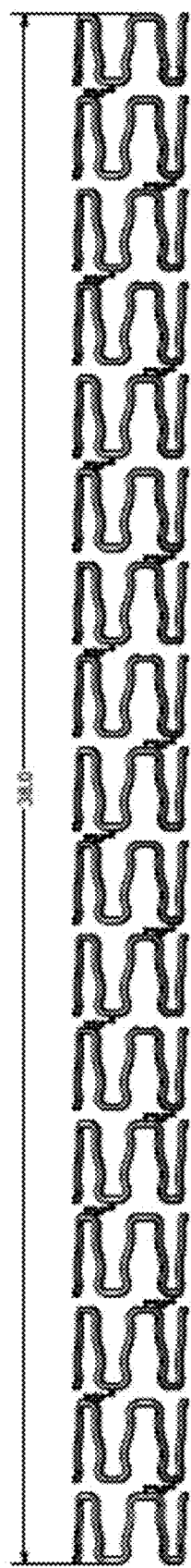
FIGS. 3A-3C illustrate view of an exemplary stent similar to the exemplary stent shown in FIGS. 1A-1F and 2A-2C. A side view of the stent device is shown in FIG. 3A.
Figure 3B:
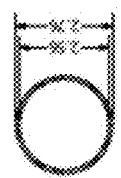
Figure 3C:
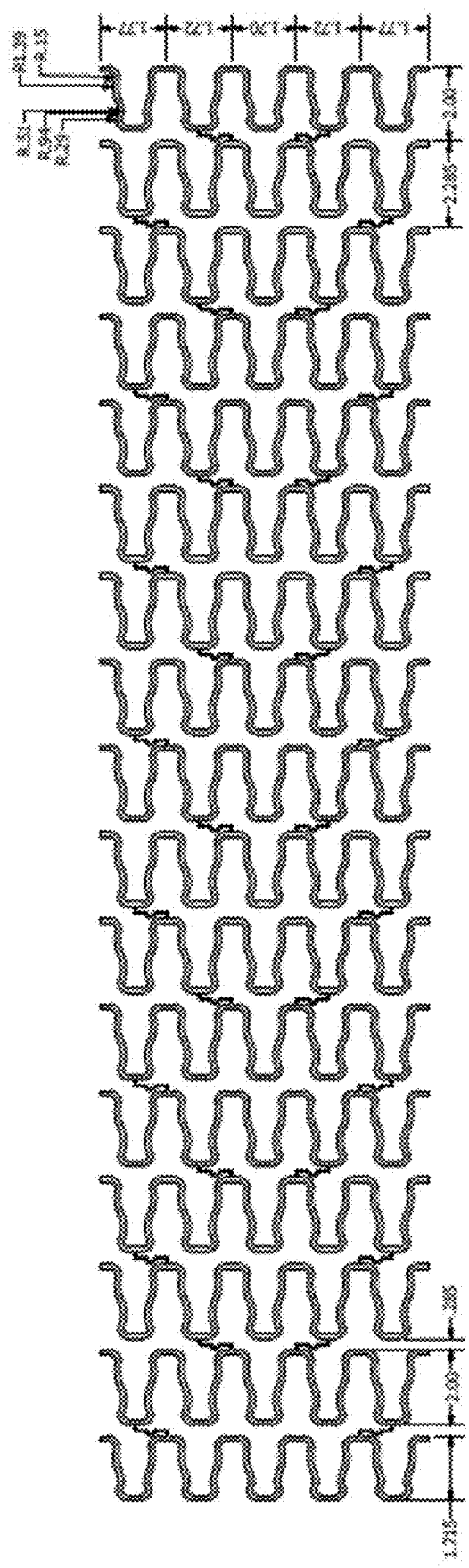

FIGS. 3A-3C illustrate an exemplary stent that is similar in many ways to the exemplary stent in FIGS. 1A-1E and 2A-2C, and any feature therein can be incorporated into this embodiment as well. This embodiment is longer than the embodiments in FIGS. 1A-1E and 2A-2C, with the exemplary length of 38 mm. The outer dimension of 2.76 mm shown in FIG. 3D is the same as in the embodiment in FIG. 1A-1E. The distance between adjacent peaks is slightly different than the embodiments in FIGS. 1A-1E and 2A-C, as shown in FIG. 3C. The crosslink connectors can have any of the dimensions of any of the crosslink connectors herein. Other exemplar dimensions are also provided in FIG. 3C.

The stents can generally be any appropriate length and have any appropriate initial outer dimension.

Exemplary materials for any of the stents herein include cobalt-chrome alloys (e.g., L605) y 316 L stainless steel. Expandable polytetrafluorethylene (ePTFE) and polyester (PET, dracon) are examples of materials that can be used for one or more sleeves, coatings or coverings on the stent, if included.

Figure 4A:
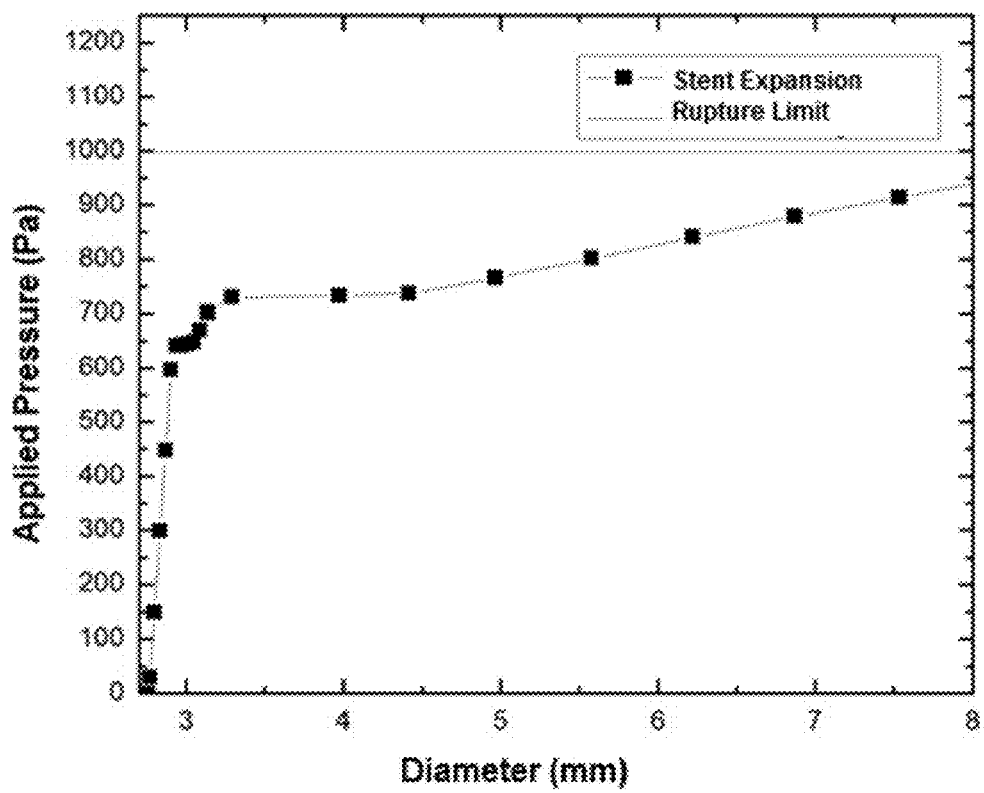
FIG. 4A is a graph illustrating an example of an applied pressure vs. diameter profile of one example of a stent apparatus as described herein.
Figure 4B:
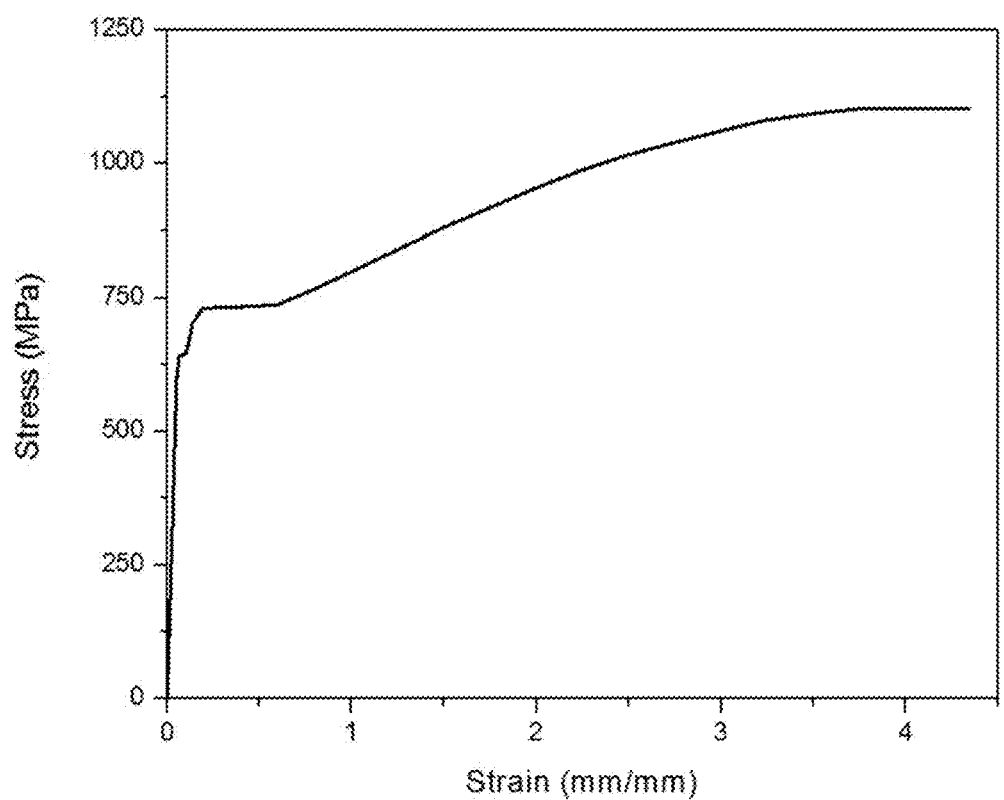
FIG. 4B is a graph illustrating an example of a stress-strain profile of one example of a stent apparatus as described herein.

FIG. 4A illustrates a pressure versus diameter graph for the stent shown in FIGS. 1A-1E, illustrating a pressure applied by an internal expansion balloon. When plotting applied pressure vs corresponding outer diameter values, stent expansion progresses gradually until reaching approximately 7.5 bar pressure. From this pressure, more accelerated expansion starts, being more susceptible to expansion as pressure increases, until reaching about 8 mm, a maximum expansion value. It is noted that this exemplary stent is configured to be able increase its diameter in approximately 2.9 times without showing fracture hazard. When removing applied pressure, a slight stent recovery occurs due to initial elastic deforming. Similarly, FIG. 4B shows an example of a stress vs. strain curve for a stent device such as those shown in FIGS. 1A-1F, 2A-2C and 3A-3C. In this example, the stress (in MPa) vs. strain (mm/mm) follows a similar profile to that shown in FIG. 4A for applied pressure vs. diameter over the ranges examined.

Figure 5:
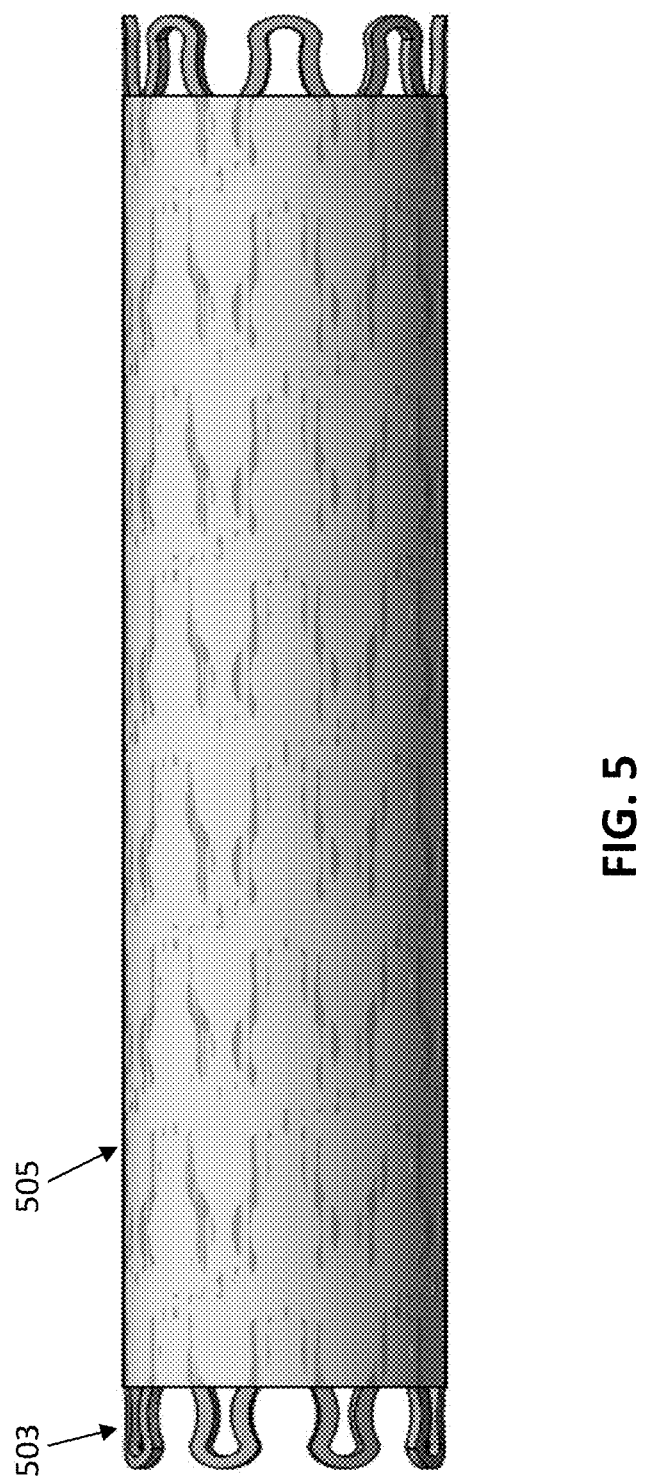
FIG. 5 illustrates an exemplary stent device including an optional sleeve (covering).

As mentioned, any of the stent devices descried herein may include a sleeve, cover, coating or the like. For example, FIG. 5 illustrates an exemplary stent device (which can be any of the stents described herein), at least a portion of which is covered by a sleeve 505. In this example, the ends of the stent frame 503 are uncovered by the sleeve. Examples of sleeves that may be used are described in greater detail below. The sleeve may be referred to herein as a graft material.

Figure 6:
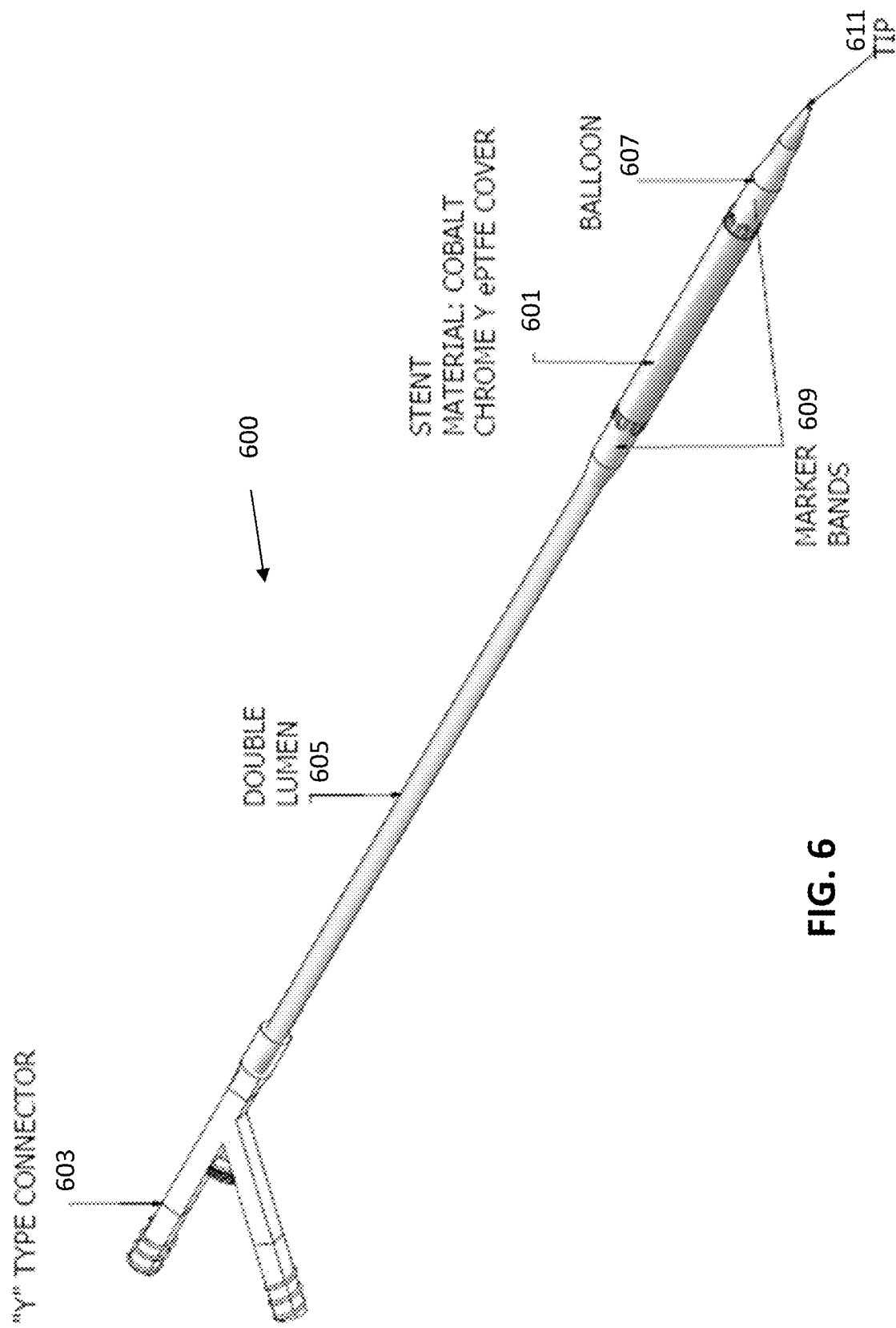
FIG. 6 illustrates an exemplary catheter system for delivering any of the stents devices herein. Any of these stent devices may be included with all or some of the delivery components shown in FIG. 6.

FIG. 6 is a perspective view illustrating an exemplary catheter system 600 for delivering any of the stents 601 described herein. This system may include a connector 603 connected to an elongate lumen 605 for inserting the stent device 601 over an expandable balloon 607. The balloon may be inflated by applying fluid through the catheter (e.g., one of the lumen of the catheter 605). One or more imaging markers 609 may be included to aid in visualizing the stent when in the body, e.g., using fluoroscopy. The tip 611 of the device may be open and a lumen through the device may be used for advancement over a guidewire (not shown).

The devices described herein may be used anywhere appropriate in the body, including, but not limited to, the peripheral vasculature. For example, a merely exemplary location for placement of the stents herein can be in tibial arteries, such as for injury to such arteries. The primitive iliac artery has a diameter between about 5 and 8 mm, and may be well suited for stents herein.

Although many of the stents described herein are shown having a plurality of parallel rings that are arranged transverse to the length of the stent, any of these devices may be configured as one or more helically arranged spirals of the unit cells that are coupled via crosslink connectors. In this case each "ring" refers to a ring per unit axil length. For example, a stent may include a single helically arranged (e.g., spiral) row of unit cells forming a plurality of coils (one ring per x units, e.g., mm, of axial length) that are connected by crosslink connectors, including s-shaped or omega-shaped crosslink connectors.

Examples

Figure 7:
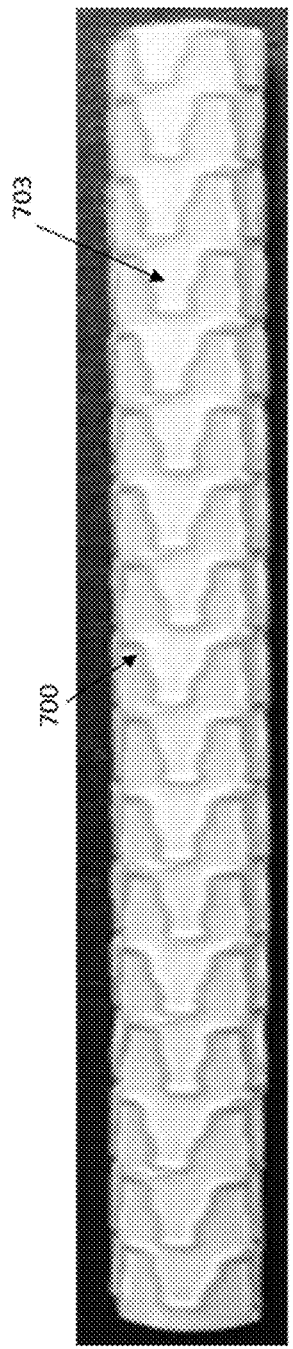
FIG. 7 shows an example of an apparatus as described herein, configured as a balloon-expandable chrome cobalt stent, including plurality of adjacent crosslink connected together by 3 or fewer omega-shaped connectors (e.g., two connectors) between adjacent rings. The stent device in FIG. 7 shows a lateral view.

FIG. 7 shows another example of a stent 700 as described herein. The stent may include a sheath or cover 703. For example the stent device frame, formed of a plurality of interconnected rings, as described above, may be embedded in a polymeric matrix 703, such as Bioweb® (Zeus Industrial Products Inc). The layers of this polymeric matrix may be applied, e.g., by electrospinning to the entire structure of the stent frame, providing a great deal of flexibility and structural stability. This may also improve its radial proprieties and allow the vascular vessel to open and recover the blood flow.

Figure 13:
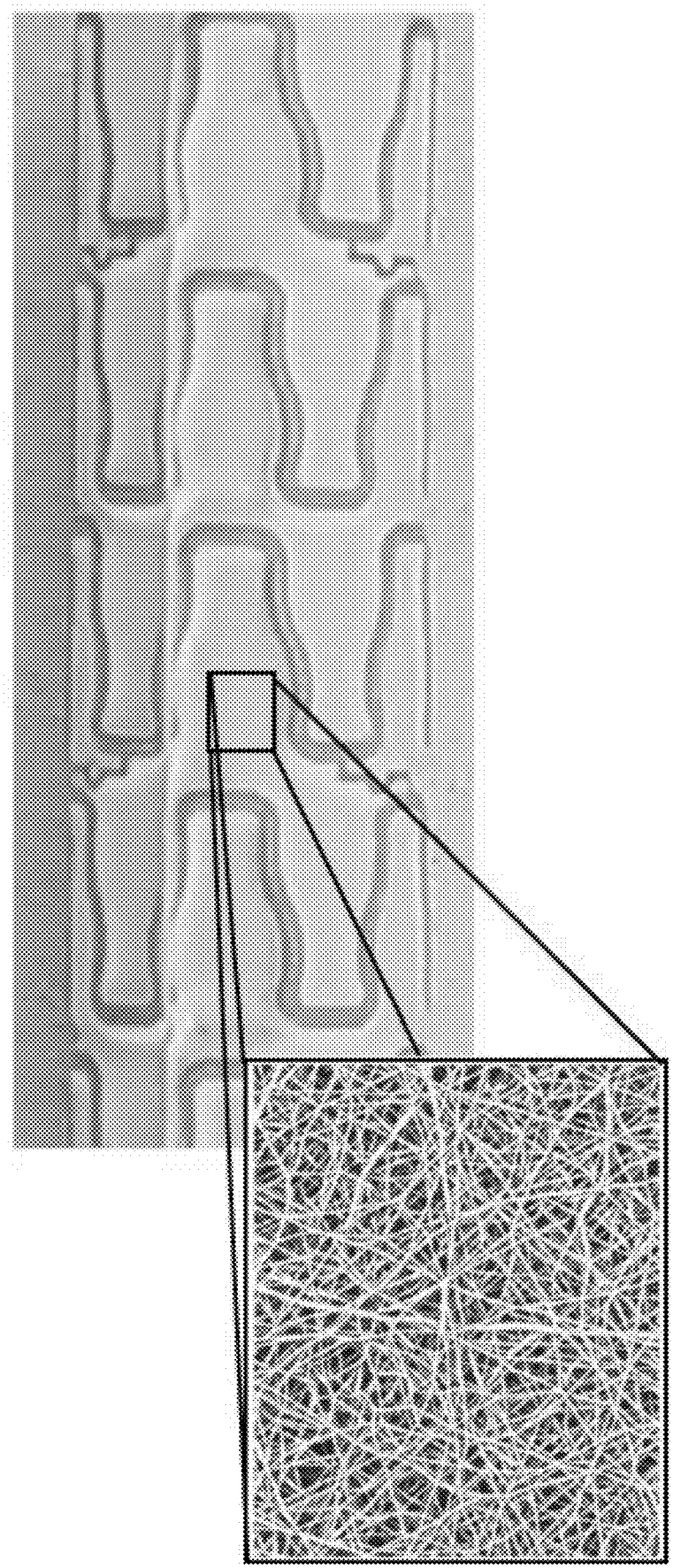
FIG. 13 is an example of a stent apparatus as described herein including a cover having a pores encapsulating the metallic frame of the stent as described herein.

FIG. 13 illustrates one example of a sleeve encapsulating a stent frame. In this example, the sleeve is formed of a porous material (such as PTFE) that is applied to the frame in an average thickness of between, e.g., about 0.02 mm to about 5 mm (e.g., between about 0.05 mm to about 1 mm, between about 0.05 mm to about 0.25 mm, between about 50 micrometers to about 500 micrometers, between about 60 to about 80 micrometers, between about 50 to about 70 micrometers, etc.). The pores may be a variety of different sizes, depending upon the needs. In some variations the sleeve may be formed by electrospinning the material onto the stent frame, using polymer fibers with thicknesses ranging from nanoscale to microscale. Fabrics with complex shapes can be electrospun from solutions, producing a broad range of fiber and fabric properties. This technique has the ability to create encapsulation technology, spin membrane/sheet, and develop 3-D structures for coating substrates of varying shapes and sizes.

Figure 8C:
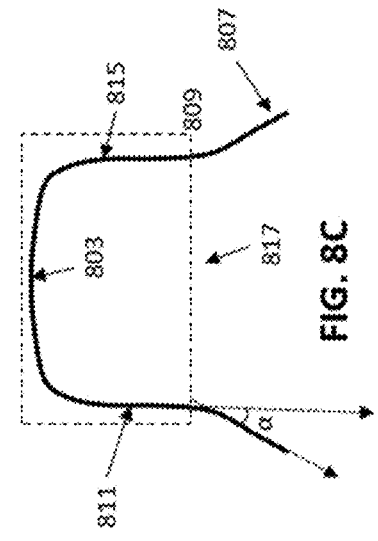
FIG. 8C shows a schematic of an example of a portion of the first open trapezoidal shape having the flattened top, two sides forming the proximal-facing opening, showing the angle formed between a connector region (connecting the first open trapezoidal shape to the second open trapezoidal shape) and the first open trapezoidal shape.
Figure 8B:
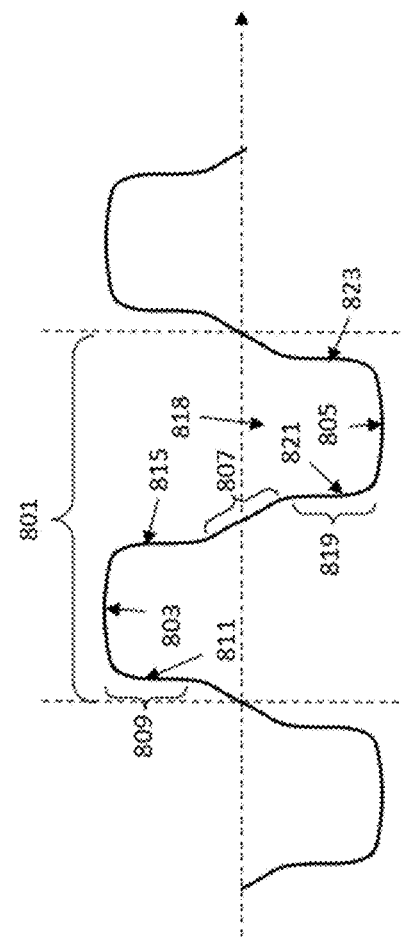
FIG. 8B shows a schematic of a plurality of repeated biphasic shapes (unit cell) including a first open trapezoidal portion having a flattened top side (e.g., a second side) and a proximal-facing opening, and a second open trapezoidal portion having a flattened top side (e.g., a fifth side) forming a distal-facing opening.

Returning to FIGS. 8A-8C, in general, the rings are formed of a length of material (e.g., metallic and or polymeric material) that forms, around the radius of the stent, a pattern of repeating biphasic cells, as shown in FIG. 8B. The repeating biphasic cells 801 typically include a pair of flattened top regions 803, 805 that are connected by an intermediate region 807. In some variations the flattened top region forms a pair of open trapezoidal portions, such as shown in FIG. 8C. In FIG. 8C, the open trapezoidal portion (dashed box 809) includes a first side or leg 811, a second side (corresponding to the flattened top 803), and a third side or leg 815. This open trapezoidal portion has a distal-facing opening 817. Similarly, a second open trapezoidal portion 819, oriented 180 degrees off of the first open trapezoidal portion 809, includes a fourth side 821, a fifth side (corresponding to the flattened top 805), and a sixth side or leg 823. The second open trapezoidal portion has a proximal-facing opening 818. The first and second open trapezoidal portions may be connected by intermediate regions 807. For example, the third side 815 of the first open trapezoidal portion may be connected to the fourth side of the second open trapezoid portion by a connector region 807, as shown, and the first side of the first open trapezoidal portion is connected to the sixth side of a second open trapezoidal portion of the next biphasic cell.

Figure 9A:
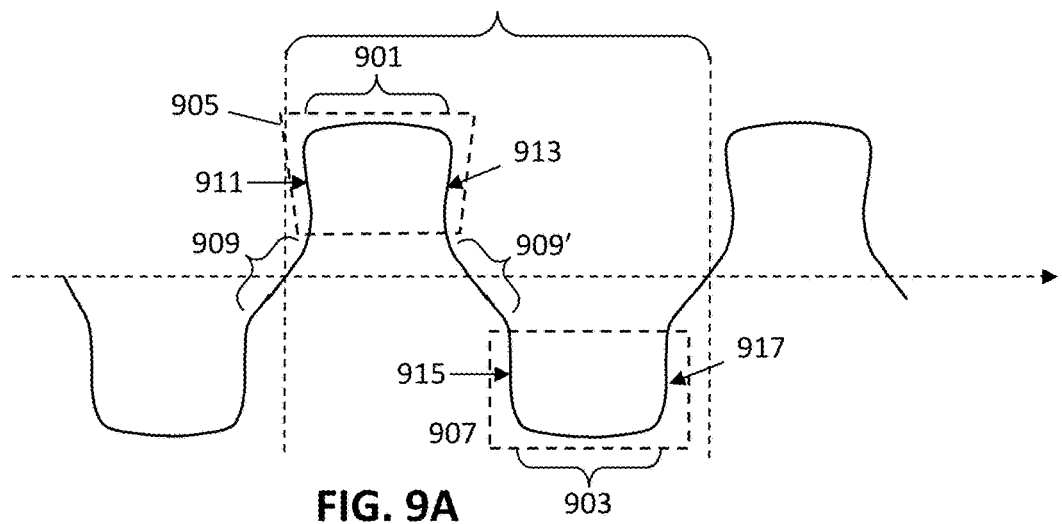
FIG. 9A-9C illustrate expansion of another example of a portion of a ring of a stent device including a repeating pattern of biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, in which the first open trapezoidal portion is connected to the second open trapezoidal portion.
Figure 9B:
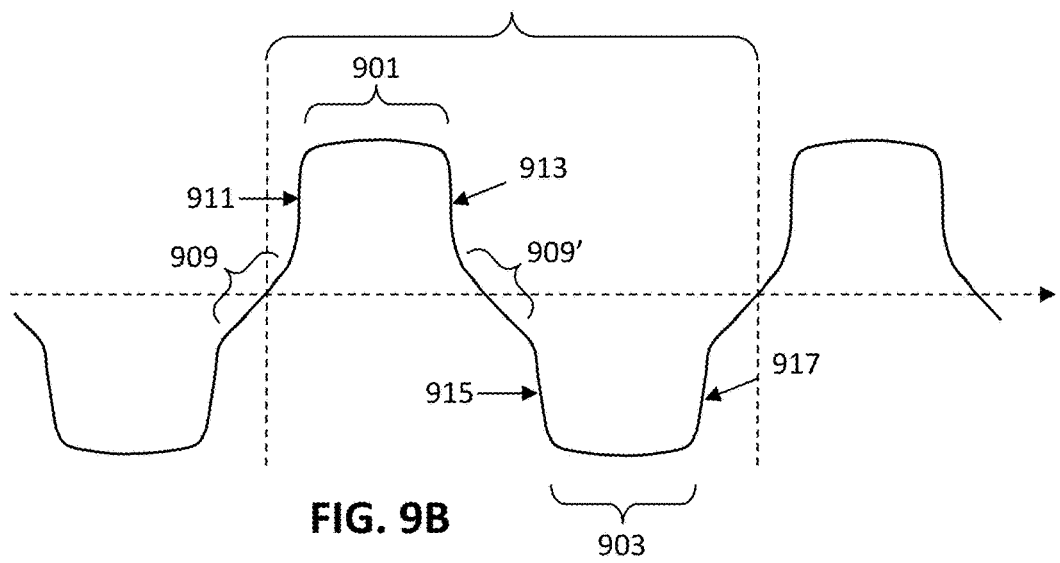
Figure 9C:
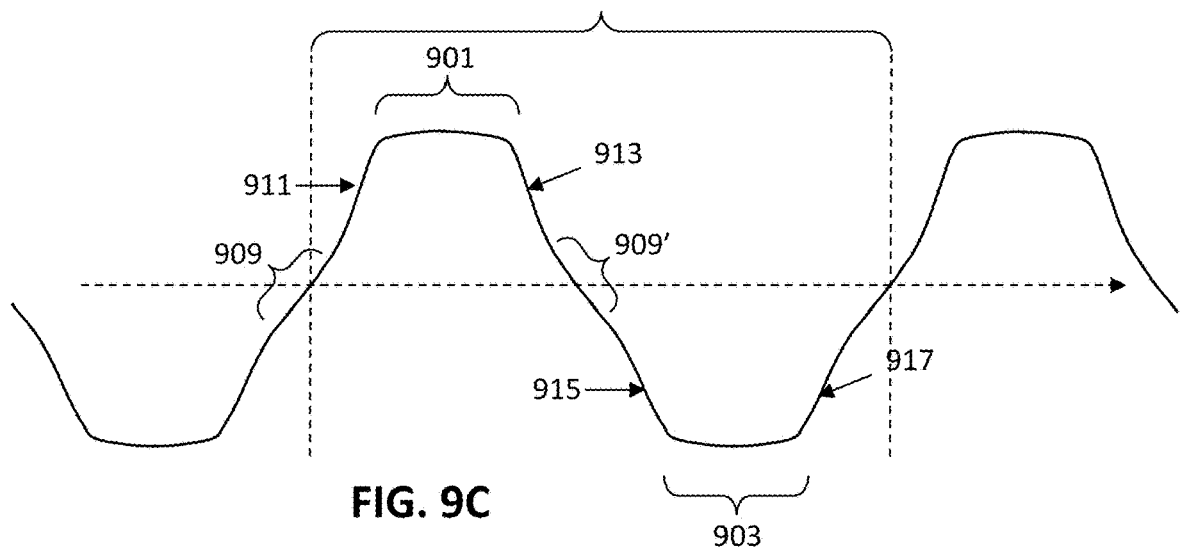

The first open trapezoidal portion and the second open trapezoidal portion may have different 'trapezoidal' shapes. For example, in FIG. 8B, the first and second open trapezoidal shape is approximately rectangular 809, and open on one side, as shown in FIG. 8C. Both the first and second open trapezoidal portions in the exemplary biphasic cell shown in FIG. 8C are the same general shape. FIGS. 9A-9C illustrate another example of a repeating biphasic cell forming a ring of a stent device as described herein, in which the first biphasic cell is an open trapezoidal portion having an isosceles (or keystone) shape 905, while the second open trapezoidal portion 907 has a more rectangular shape, at least in the un-expanded shape (shown in FIG. 9A). The dimensions of the open trapezoidal portions (e.g., the lengths of the flattened top regions 901, 903) are approximately the same.

Figure 10A:
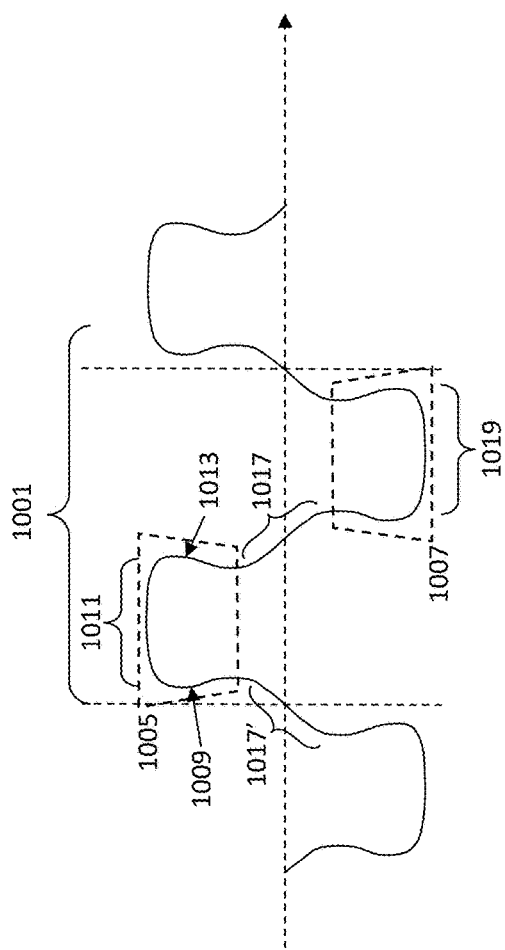
FIG. 10A is an example of another variation of a plurality of repeated biphasic shapes (unit cell) including a first open trapezoidal portion having a flattened top side (e.g., a second side) and a proximal-facing opening, and a second open trapezoidal portion having a flattened top side (e.g., a fifth side) forming a distal-facing opening. In this example, the first and second open trapezoidal portions have the same shape (e.g. rounded isosceles trapezoids in which the sides of the trapezoid forming the opening are angled in).
Figure 10B:
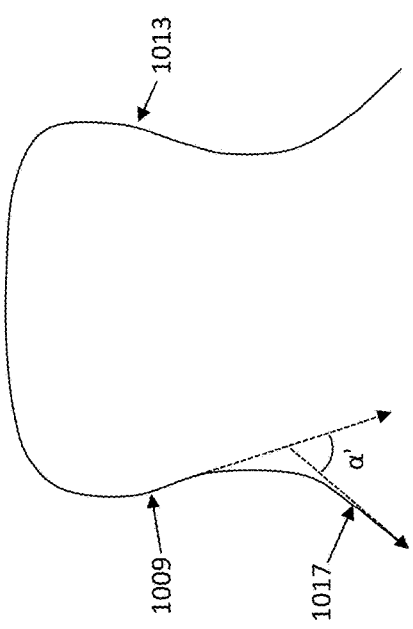
FIG. 10B shows a schematic of an example of a portion of the first open trapezoidal shape having the flattened top, two sides forming the proximal-facing opening, showing the angle ($\alpha'$) formed between a connector region (connecting the first open trapezoidal shape to the second open trapezoidal shape) and the first open trapezoidal shape.

FIGS. 10A-10B illustrate another example of a repeating biphasic cell 1001 in with the first and second open trapezoidal portions 1005, 1007 are approximately the same (e.g., isosceles) shape. As shown in FIG. 10B, the open trapezoidal portion 1005 in this example includes first 1009, second (flattened top 1011) and third 1013 sides. The first 1009 and third 1013 sides are angled inwards forming the open isosceles trapezoidal shape. The angle (a) shown provides and angle of the first or third sides relative to the intermediate connector 1017.

As shown in all of these examples the open trapezoidal shapes may have rounded (curved) edges. In some variations the open trapezoidal shapes may have straight edges (e.g., angled edges). In addition, the flattened tops (e.g., 803, 805, 901, 903) may be flat or approximately flat, as shown. Thus, they may be curved slightly (typically <15 degrees of curvature, e.g., <12 degrees, <10 degrees, <8 degrees, etc.). The flattened tops of the first and second open trapezoidal portions shown are parallel, where in the context of the flattened (e.g., slightly curved) tops, the term parallel means substantially, parallel, so that an average vector through the flattened top portion of the first open trapezoidal portion (see, e.g., 832, FIG. 8A) is parallel to an average vector through the flattened top portion of the second open trapezoidal portion.

Figure 8A:
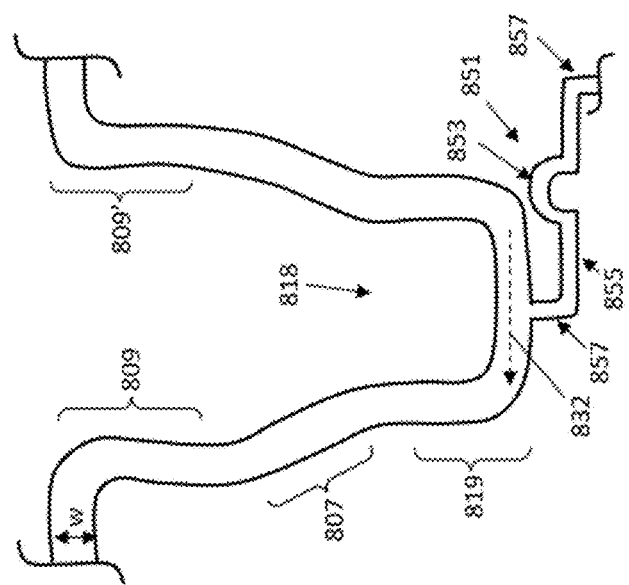
FIG. 8A is an example of a portion of a stent apparatus, showing an open trapezoidal region including a flattened surface to which an omega-shaped connector is attached.

FIGS. 8B-8C, 9A-9C and 10A-10B schematically illustrate the repeating biphasic cells; in practice the cells may be formed of a length of material having a width, w, as shown in FIG. 8A. In this example, the width is constant; in some variations the width may be narrower, e.g., in the intermediate region connecting the open trapezoidal regions. In FIG. 8A, the exemplary portion of the repeating biphasic cell shows an open trapezoidal portion 819 having a proximal-facing opening 818 and half of the adjacent open trapezoidal portions 809 having distal-facing openings. FIG. 8A also shows an example of an omega-shaped ring connector 851 that is connecting to the flattened top of the open trapezoidal portion 819 at a middle region. The omega ring connector includes an arc ("domed") region 853 and two laterally extending arms extending from the arc 855. The ends of the omega-shaped crosslink connectors may be L-shaped 857, 857' so as to connect perpendicularly to the flattened top(s).

In general, the repeating biphasic cells forming the rings may have a generally interconnected "U" shape, with the U-shapes alternating as distal-facing and proximal facing radially around the circumference of the stent in each ring. As shown and described above, the generally U-shaped geometry may also be described an open trapezoidal portion. Thus, the U-shapes may have an inwards curved part in the beginning of the figure and afterwards an outwards curve. The tops of the U's may be connected to each other by an intermediate region, which may be angled or curved, as shown. Thus, the repeating biphasic cell may be formed of a pair of connected U-shapes.

The repeating biphasic cell shapes allow the stent to expand adequately and give the stent enough stability to expand and maintain the peripheral vascular vessel open. The radial stability and homogeneity of the stent may be improved by including a sheath, e.g., embedding it in a membrane, as described above.

FIGS. 9A-9C illustrate the effect of expansion of the stent on a portion of a ring, showing the movement of the intermediate region 909 and/or the legs of the open trapezoidal region(s) as the device transitions from an unexpanded configuration (shown in FIG. 9A) to an expanded configuration (shown in FIG. 9C). For example, in FIG. 9A the repeating biphasic cell pattern is shown in the unexpanded configuration, and the first and second open trapezoidal portions 905, 907 are shown with the first 911 and third 913 sides and fourth 915 and sixth 917 sides angled slightly inwards and the first and second open trapezoidal portions 905, 907 are connected to each other by an intermediate region 909 (adjacent repeating biphasic cells are also connected by intermediate regions 909'). FIG. 9B shows a schematic of the repeating biphasic cell of FIG. 9A after the ring formed by the repeating biphasic cell has begun to expand, e.g., by applying an expansion force from a balloon. In FIG. 9B, the first and third sides of the proximal-facing open trapezoidal portion 901 have opened slightly (e.g., expanding the open trapezoidal shape) and the angle of the intermediate regions 909, 909' has changed as well. Similarly, the fourth 915 and sixth 917 sides have also opened slightly. As expansion continues, in FIG. 9C the first 911 and third 913 sides and the fourth 915 and sixth 917 sides have opened relative to the flattened tops 901, 903 even more, resulting in the expansion (without substantial foreshortening) of the repeating biphasic cells.

Figure 12:
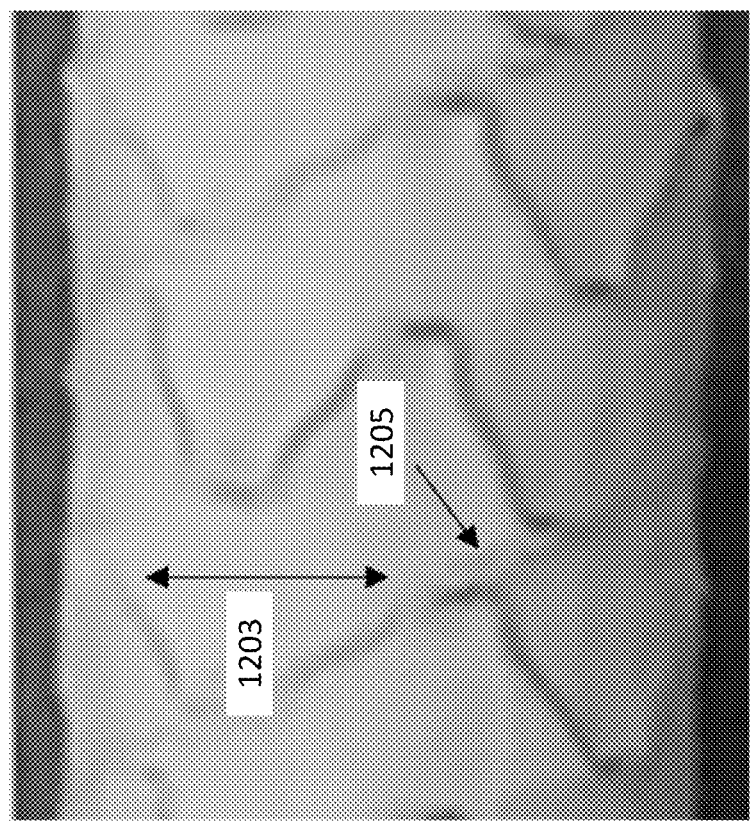
FIG. 12 shows an example of a stent device as described herein in an expanded configuration. In this example, the flat top regions remain flat, and although the unit shapes are foreshortened slightly, this is compensated at least in part by the expansion of the omega-shaped crosslinks.
Figure 11:
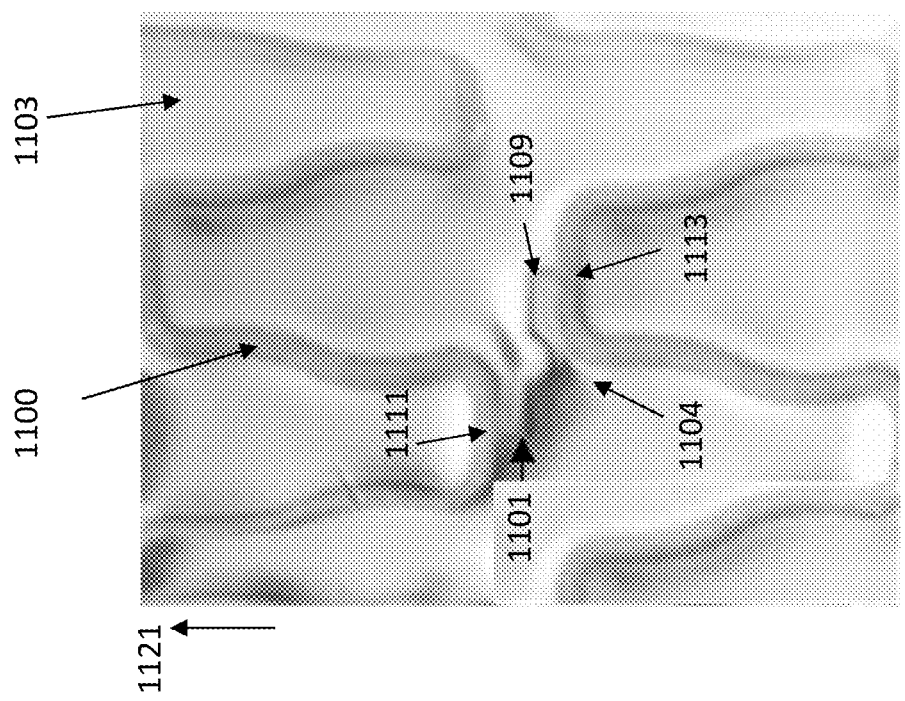
FIG. 11 illustrates one example of a portion of two rings of an exemplary stent apparatus including an omega-shaped crosslink that may be used to join the rings of repeated biphasic shapes (open trapezoidal shapes) forming the stent. Adjacent rings may be interconnected through two (or in some variations, more) crosslinks placed between peaks between adjacent rings.

FIGS. 11 and 12 illustrate an example of a stent device similar to those described above. In FIG. 11, a portion of a stent frame 1100 encapsulated in a sleeve 1103 is shown. The frame is in an un-expanded configuration. FIG. 11 shows an omega-shaped ring connector 1104 connected via an L-shaped connector 1101 to a flattened top of a first open trapezoidal portion 1111 having a distal-facing opening (the distal direction 1121 is 'up' in FIG. 11). The opposite end of the omega-shaped ring connector 1109 is a second L-shaped connector (e.g., a right-angled connector) that is connected to a flattened top of another open trapezoidal portion 1113 having a proximal-facing opening on an adjacent ring of the stent.

A stent such as the one shown in FIG. 11 is shown in an expanded view in FIG. 12. In this example, similar to that shown in FIG. 9C, above, the stent frame 1200 is expanded so that the sides of the open trapezoidal portions forming the distal- and proximal-facing openings are spread further apart and the angle between the interconnecting intermediate regions and the flattened top regions is larger, while the flattened top regions remain parallel, and essentially unchanged from the un-expanded configuration. In FIG. 12, the distance between the flattened ends 1203 is much larger than in the un-expanded configuration. The omega-shaped crosslink(s) 1205 continue to connect the adjacent rings together, while bending to minimize foreshortening of the stent, even when the diameter of the stent increases more than twice its un-expanded diameter.

As described above, the rings forming the stent are interconnected through the omega-shaped crosslink connectors that build up the stent. Every cylindrical ring, other than the most proximal and the most distal rings, may be connected to adjacent cylindrical rings through two sets of crosslink connectors, one set of crosslink connectors connecting from a more proximal to the cylindrical ring, and the second set of crosslink connectors connecting from the cylindrical ring to a more distal ring. The crosslink connectors may be placed at spaced locations, as shown in FIG. 1A-1F, above. The crosslink connectors are not typically placed on the same connection point as the adjacent rings, but (as shown) may repeat the pattern every other ring. The omega shape or S-shape may give the stent flexibility when it has to expand. For example, the crosslinks design may allow them to be embedded in a material (e.g., ePTFE or PTFE) as well as to be crimped and uniformly expanded without ruptures. This type of crosslinks may allow the stent to crimp in the catheter without overlapping each other. As will be described below in FIGS. 16A-16B, the rings may not overlap when the stent is compressed and/or bent in the catheter. The crosslink connectors may be identical and may have the same organization (orientation) along the stent's length. The stent can be compressed to a diameter that is smaller than the one it was designed in, in order to be placed correctly on the balloon, to obtain a thin profile when placed on the catheter and/or to avoid the stent migration when introduced in the tortuous paths of the vascular vessels.

Thus, in some variations, the membrane, together with the repeating biphasic cell pattern that forms the stent, may make the stent flexible, and the position of the crosslink connectors may improve the stent's flexibility, giving a uniform flexibility in the whole structure when the stent graft is bent or kinked. The uniform flexibility may be assisted by the sleeve (e.g., membrane) and the link between the rings through the omega-shaped crosslink connectors.

Figure 14A:
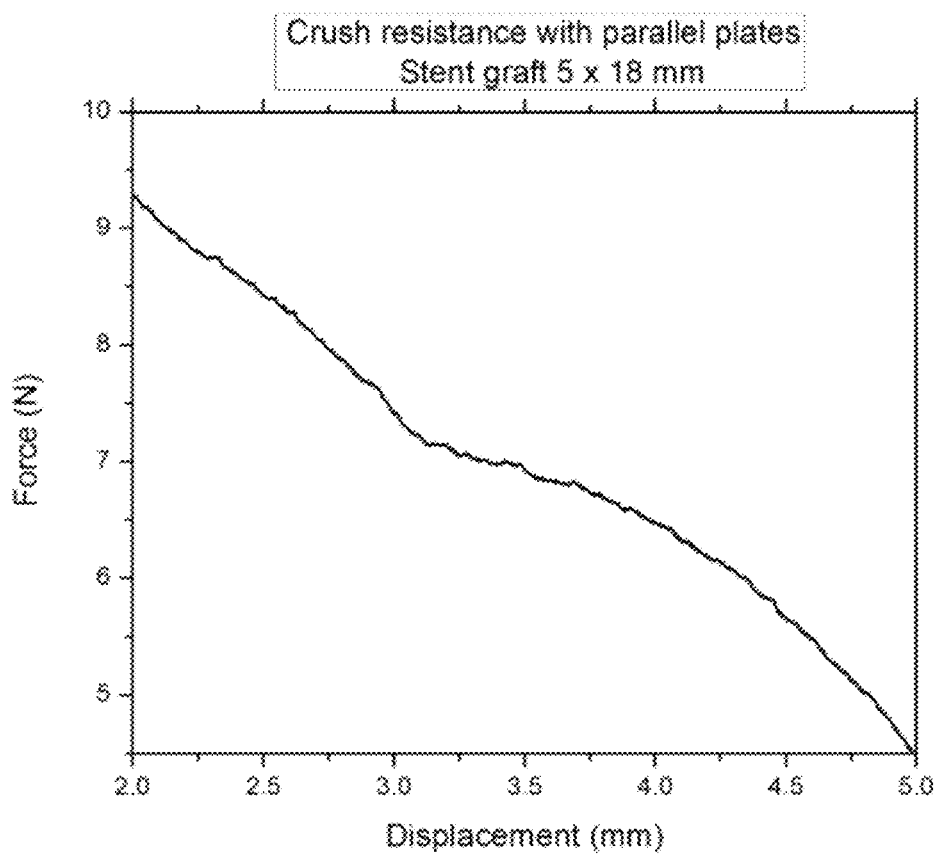
FIG. 14A is a graph showing an example of crush with parallel plates (radial compression) for an example of a stent apparatus as described herein (force×displacement), showing the compression at 50% of the diameter of the stent of about 7.5 N.
Figure 14B:
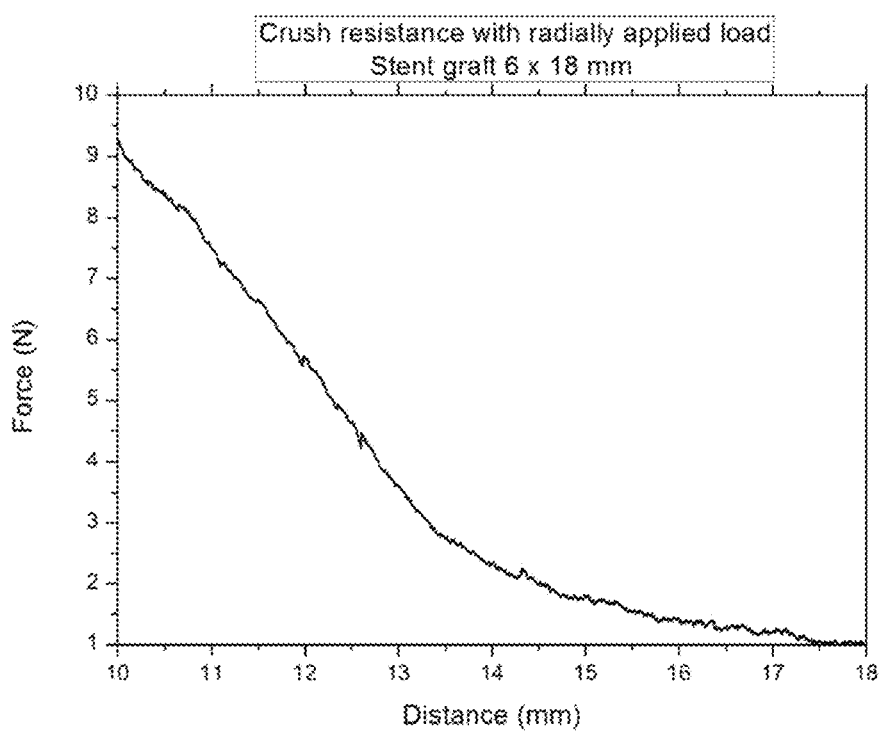
FIG. 14B is a graph showing an example of crush resistance for an example of a stent apparatus with radially applied loads for an example of a stent apparatus as described herein (force×distance).

The stent devices described herein are highly flexible, and may be bent over a tight radius of bending without kinking. For example, FIGS. 14A and 14B illustrate the resistance to crushing of these stents. In FIG. 14A, the graph illustrates compression at 50% of the dimeter of the stent, which occurs when a force of about 7.5 N is applied. The test shown in FIG. 14A was performed until the stent was compressed approximately 50% of its length. As shown in FIG. 14B, the maximum force reached was about 9.5 N.

Figure 15C:
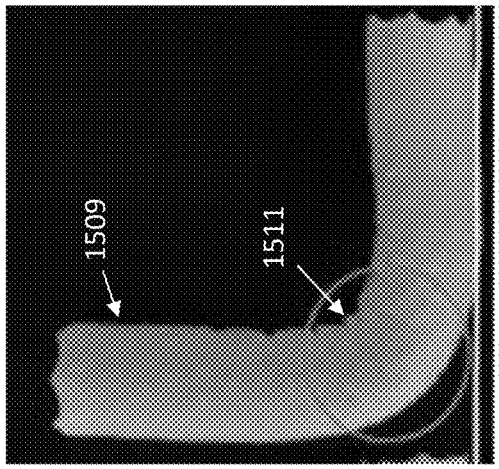
FIGS. 15A-15C illustrate examples of prior art stents showing kinking during bending at 90 degrees.
Figure 15B:
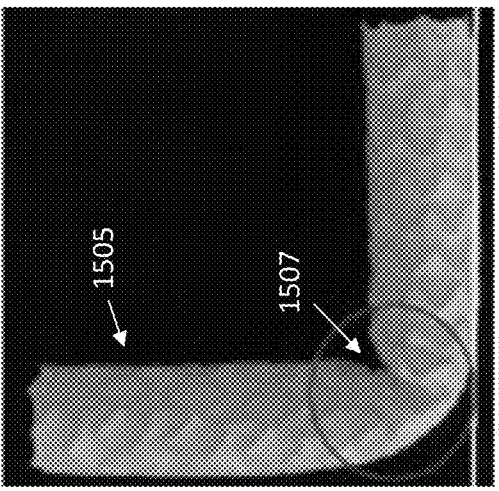
Figure 15A:
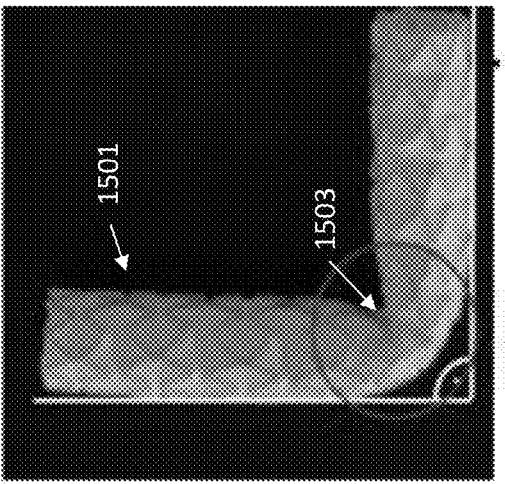

The mechanical properties, including the flexibility and resistance to kinking, was apparent when compared to other prior art stents having similar dimensions. For example, FIG. 15A-15C illustrate various prior art stents in which the flexibility was examined when bending the stents 90 degrees with a very short radius of bending (bending at almost a right angle). For example, FIG. 15A shows bending of a first prior art stent 1501, showing an 8×58 mm stent ("LifeStream" covered stent by CR Bard, having a sinusoidal stent pattern with an offset connector between adjacent rows of sinusoids). This stent kinked 1503 at tight bend radius, as shown. Similarly, FIG. 15, showing an 8×59 mm prior art stent 1505 ("Advanta V12" covered stent by Getinge is a PTFE covered stent having an open cell pattern of adjacent zig-zags interconnected by longitudinal links); this stent also kinked 1507. The prior art stent 1509 in FIG. 15C ("BeGraft" covered stent by Bentley, having a repeating pattern of curly bracket-shapes) also kinked 1511, though less than the devices in FIGS. 15A and 15B.

Figure 16B:
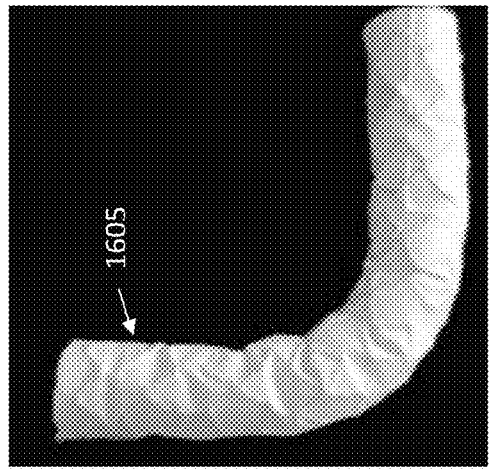
FIGS. 16A and 16B illustrate examples of the stent apparatuses described herein in 90 degree bending, showing smooth (unkinked) bending over the same experimental parameters as the prior art stents shown in FIGS. 15A-15C, but with substantially less kinking or reduction in diameter.
Figure 16A:
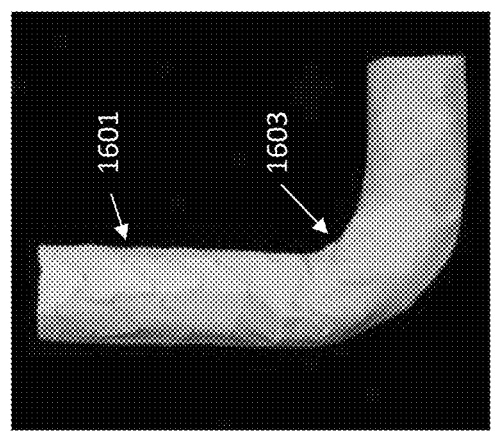

In contrast the stent devices described herein do not appreciably kink. For example a covered stent device having a plurality of adjacent rings arranged transverse to a length of the device, wherein each ring is a ring comprising length of material arranged radially around the length of the stent device as a plurality of repeating biphasic cells, as described above, when bent 90 degrees over the same bend radius did not kink, as shown in FIGS. 16A and 16B. In FIG. 16A, the 5×38 mm stent 1601 did not kink at the bend 1603, in contrast to the prior art devices. Similar result were seen with a 10×58 mm stent 1605, as shown in FIG. 16B and with 5×38 mm and 8×38 mm stents (not shown). The stent devices described herein flexed without kinking or exhibiting a diameter reduction of greater than 50% when bent up to at least 90 degrees over a short length, as shown, in contrast to prior art devices.

Figure 17A:
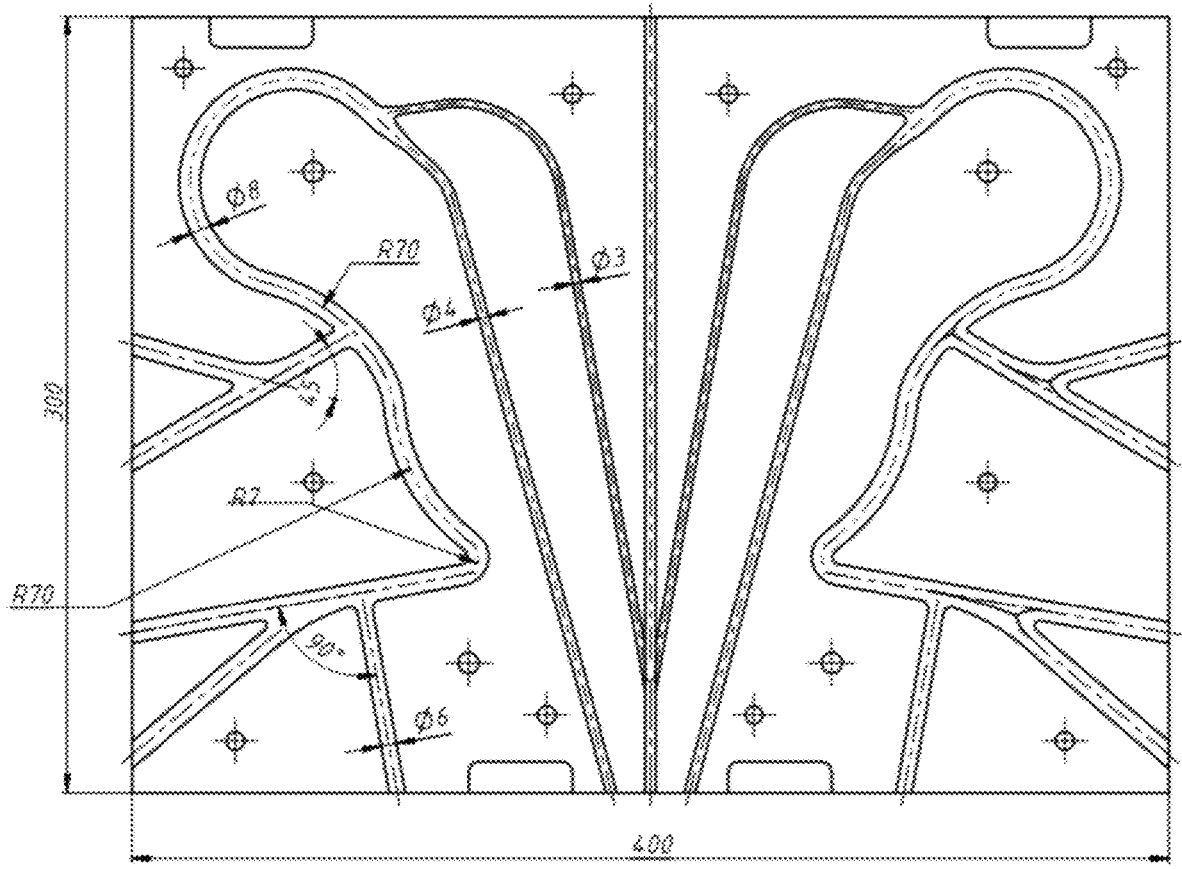
FIG. 17A illustrates an example of a navigability test jig that may be used to characterize a stent apparatus as described herein, having regions ("arteries") of 3, 4, 6 and 8 mm diameters, at angles of between 30-90 degrees and various radius of curvatures.
Figure 17B:
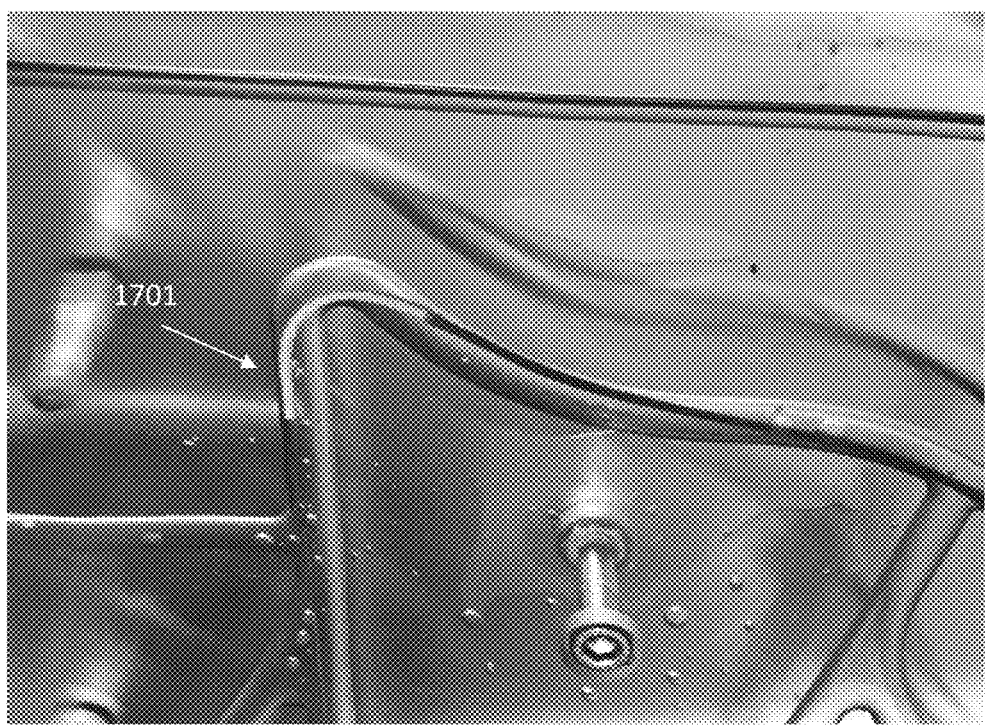
FIG. 17B is an example of one variation of a stent apparatus as described herein shown navigating a test jig such as the one shown in FIG. 17A.

Because the stents described herein also have both a high flexibility, high resilience and a high resistance to kinking, these stents are highly navigable, able to navigate even the most tortious vessels. Navigability testing was performed on the exemplary stent devices described herein. The navigability test consists of introducing a catheter with the stent covered with PTFE in a device that simulates the peripheral arterial vasculature, such as the device ("jig") shown schematically in FIG. 17A. The test was performed by a physician specialized in stenting technique. The result of the tests is qualitative, but showed extremely high degrees of navigability and flexibility. The devices described herein were successfully deployed in vessels having diameters of between 3-8 mm (e.g., 3, 4, 6 and 8 mm respectively). For example, FIG. 17B shows an example of a navigability test in which a catheter including a stent 1701 was navigated through a tortious model of a vessel relatively easily. The model used has more complex trajectories than typical peripheral human anatomy. A catheter with a stent graft was navigated smoothly through the device, including through regions of high tortuosity without damage and remained positioned in the catheter. The stent graft has adequate flexibility to traverse complex trajectories, including 30 degree, 45 degree, 60 degree and 90 degree bends.

In general, the stents described herein may be any appropriate size (e.g., unexpanded diameter, expanded diameter, and length). The configuration of repeating biphasic cells and crosslink connectors, including both S-shaped and omega shaped, described herein may be particularly well suited for smaller diameter (e.g., 7 m or less) and/or smaller length (e.g., 40 mm or shorter) devices. FIGS. 18A-18D each provide example parameters for four different examples of stents as described herein. All of these exemplary stents were made as covered stents, with an ePTFE sheath (in this case the sheath encapsulated the stent frame as described above). For example, FIG. 18A describes a 5×18 mm stent graft having an initial (unexpanded) diameter of 2.1 mm and final (30 seconds after removal of the balloon) diameter of 5.0 mm. FIG. 18B describes a similar 5×38 mm device, having a starting diameter of about 2.2 mm and a final (30 seconds after removal of the balloon) of about 4.9 mm. FIG. 18C shows an example of a 6×18 mm stent, and FIG. 18D shows an example of a 6×38 mm stent device. In general, all of these devices went from an unexpanded configuration to an expanded configuration of greater than 2× the unexpanded configuration yet had less than 7% foreshortening (e.g., less than 6.5%, less than 6%, less than 5.5%, etc.).

Figures 19D, 19E, 19F:
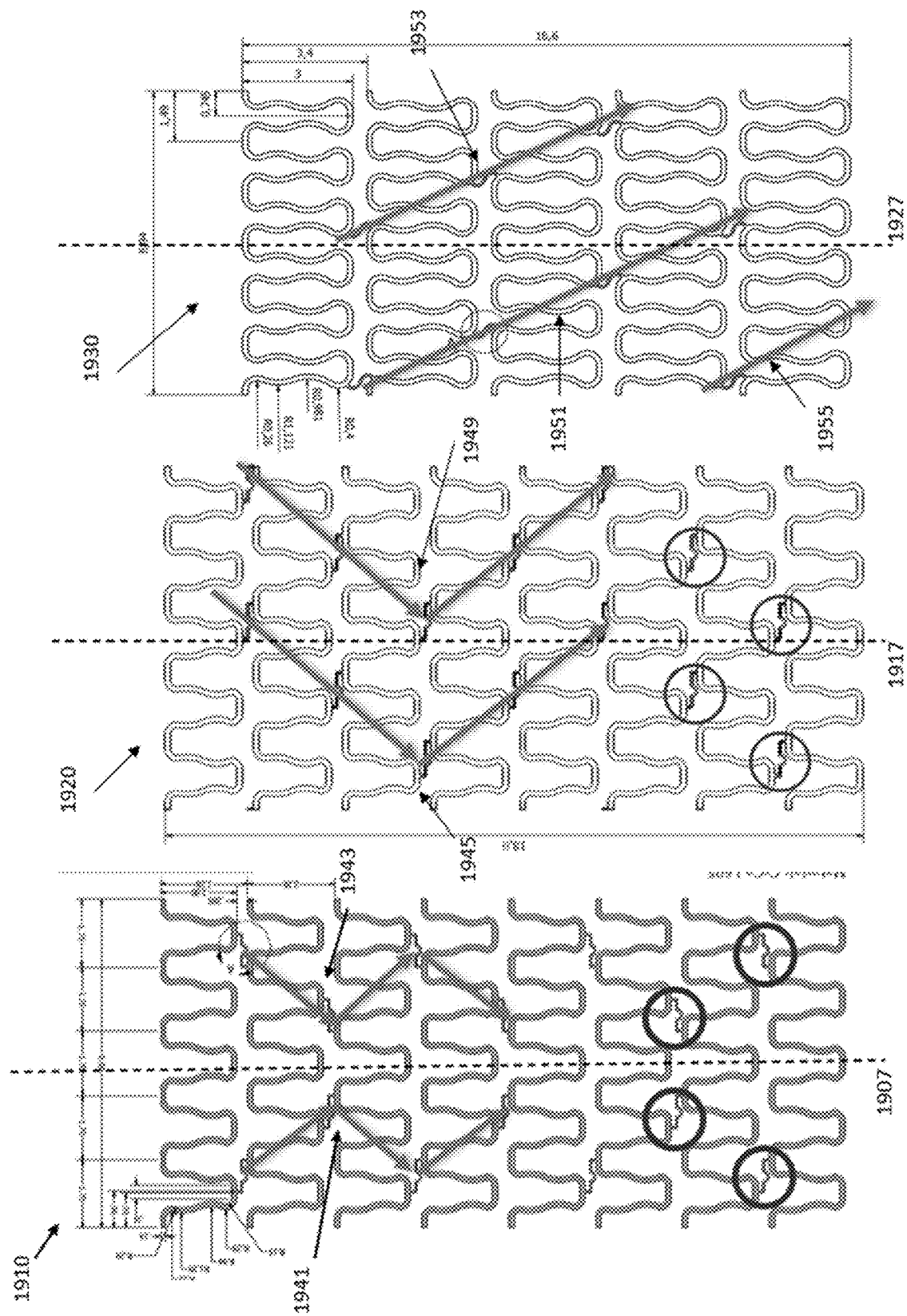

FIGS. 19A-19C compares the relative positions of crosslink connectors and differing types of crosslink connectors in different exemplary stent devices, where each stent is oriented with the distal end of the device at the top of the figure, and the proximal end of the device at the bottom of the figure, shown vertically here. In FIG. 19A, the exemplary stent device 1910, similar to that of FIG. 1D, is shown. The repeating biphasic cells (unit cell) are as described above in FIG. 1D, and may have similar dimensions. The crosslink connectors in this embodiment are omega shaped crosslink connectors, which further include L-segments, permitting the connection with each flattened top/bottom to be perpendicular. The distribution of the crosslink connectors for each connecting portion, which comprises a ring and the crosslink connectors connected thereto, varies in an A-B-A-B pattern, and also is distributed around the center point radially. That is, viewing down a vertical center line 1907 of the stent, the crosslink connectors are distributed in a symmetrical or mirrored arrangement about the center line 1907. In FIG. 19A, the ring connector arrangement for the most proximal ring 1905 and the more distal adjacent ring 1903 is specifically pointed out. For this exemplary device, each ring has 5 repeating units with alternating open trapezoids facing distally and proximally. For ring 1905, ring connector 1902 is connected from a center point of a flattened top of ring 1905 to a center point of a flattened bottom of ring 1903, where the flattened top is of ring 1905 is the second flattened top from the center line. The other ring connector 1904 of this connecting portion similarly connects from the center of a second flattened top to the right of the center line 1907, to a center point on a flattened bottom of ring 1903, which is offset further away from the center line 1907 than the site of connection on the flattened top on ring 1905. Looking at the crosslink connectors between ring 1901 and 1903, the connection points of ring connector 1906 are shifted one flattened top/flattened bottom unit closer to the right towards the center line 1907. The corresponding ring connector 1908 is symmetrically shifted to connect between the rings 1901 and 1903 one flattened top/flattened bottom unit closer to the left towards the center line 1907. As shown in FIG. 19D, the patterns 1941, 1943 repeat each alternating row throughout the length of the stent in the A-B-A-B pattern about the center line 1907 and are symmetrical with respect to a centerline of stent 1930.

FIG. 19B shows a different exemplary stent 1920, which has the same dimensions and has the same crosslink connectors, e.g., omega shaped crosslink connectors. However, in this device, the distribution of the crosslink connectors is configured differently. Ring connector 1912 connects from a center point of a flattened top of ring 1915 to a center point on a flattened bottom of ring 1913 offset away from the center line 1917 relative to the point of connection of ring connector 1912 onto ring 1915, which itself is the second flattened top of ring 1915 to the left of the center line 1917. Ring connector 1914, also connecting from ring 1915 and connecting to ring 1913, is now designed to connect from a center point of a flattened top of ring 1915 just to the right of the centerline 1917, and connects to a center point on a flattened bottom of ring 1915, which is offset, and is located right along the centerline 1917. The connector 1916 connects from ring 1913 to ring 1911, and connects from a center point on a flattened top of ring 1913 just to the left of the center line to a center point on a flattened bottom of ring 1911 offset and further to the left away from the centerline, relative to the connection point on ring 1913. The connector 1918 connects from a center point on the second flattened top to the right of the center line of ring 1913, to a center point on a flattened bottom of ring 1911, which is offset to the left of the connection point on ring 1913. The pattern of ring connector connection points between ring 1913 and ring 1911 is shifted diagonally compared to the connection points of crosslink connectors between ring 1915 and ring 1913, as shown in FIG. 19E. In this example, the diagonal shift is one unit cell shift to the right, proceeding from distal to proximal, for patterns 1945, 1947. The distribution can also be described as shifting radially (e.g., circumferentially) by one unit cell. As shown in the additional rings, the patterns 1945, 1947 shifts to the right, then reverses to the left, yielding an ABCBA pattern, looking from distal to proximal.

FIG. 19C shows yet another exemplary stent device 1930. This device includes unit cells having a different shape from that of device 1910, 1920. Each flattened top and bottom are connected via intermediate or connecting regions having a more pronounced curve such as a pair of sigmoid curves, and the unit cell is more symmetrically shaped from flattened top to flattened bottom. The length of the unit cell, from the top of the flattened top to the base of the flattened bottom is longer, e.g., 3 mm compared to 2 mm for the same dimension in device 1910, 1920. The width, radially or circumferentially, of the unit cell of device 1930 is smaller (1.49 mm) compared to that of devices 1910, 1920 (1.70 mm). In this exemplary stent, the length, proximally to distally, is 16.6 mm. The crosslink connectors of this device are S-shape crosslink connectors and attach to a point offset from the center point of a flattened top or flattened bottom. The offset point may be at the curved region defining one end of the flattened top or flattened bottom. The space between successive rings for device 1930 is larger (0.4 mm) compared to the space between successive rings for device 1910, 1920 (0.28 mm). Further, the S-shape crosslink connectors connect to the adjacent ring in a direction aligned parallel to the center line of the device, and are not connected in an offset direction, ring to ring. In this exemplary device, two S shape crosslink connectors also are used to connect a ring to an adjacent ring. The S-shape crosslink connectors 1922, 1924, which connect from ring 1929 to ring 1925, are connected to flattened bottoms along the ring 1925, separated by two other flattened bottoms. S-shape crosslink connectors 1922, 1924 are non-symmetrically disposed relative to the centerline 1927. The S shape crosslink connectors 1926, 1928 which connect from ring 1925 to ring 1923, are connected to two flattened bottoms shifted by one-unit cell to the left, relative to crosslink connectors 1922, 1924, and are symmetrically disposed relative to the centerline and are separated from each other by the same distance of two flattened bottoms separation. The same shift to by one unit cell to the left, distal to proximal is seen in the positions of the S shape connectors 1932, 1934, which connect ring 1923 to ring 1921, and shown in FIG. 19F, marked as patterns 1951, 1953, 1955. The pattern for this stent device is an ABC repeat, and is directed in a leftward direction, from distal to proximal. Without wishing to be bound by theory, this design affords a less rigid stent, due at least to the non-offset nature of the connections made by the crosslink connectors, ring to ring, and to the increased length of the unit cells, e.g. a given length of stent will have fewer crosslink connectors connecting adjacent rings.

Figure 20A:
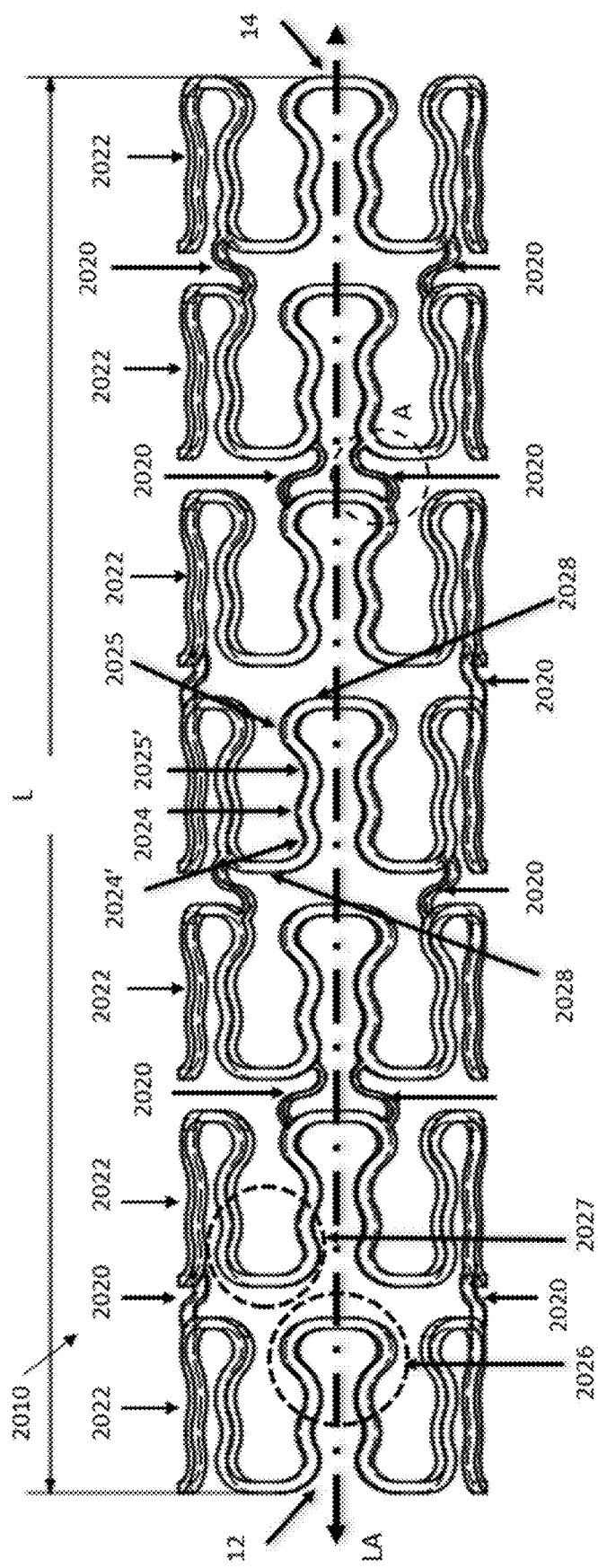
FIGS. 20A-20C show exemplary dimensions of one variation of a stent apparatus according to some embodiments of the disclosure.
Figure 20C:
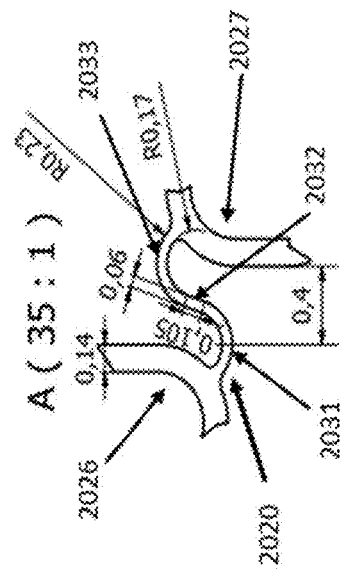
Figure 20B:
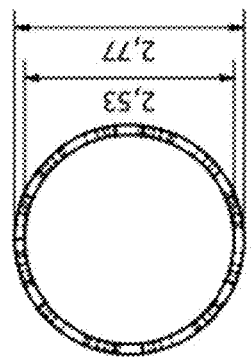

FIGS. 20A-C show another exemplary stent 2010. FIG. 20A illustrates a side view of exemplary stent 2010 in an un-expanded (e.g., delivery) configuration, stent 2010 having a first end 12 (e.g., proximal end) and a second end 14 (e.g., distal end) and a length, L; thus stent 2010 has a longitudinal axis LA extending through a lumen defined by the stent. Stent 2010 includes a plurality of annular supports 2022 ("rings") transverse to the long axis and generally axially spaced from at each other; the individual regions are connected by at least one ring connector 2020 (e.g., S-shape ring connector). In this example, an annular support is "adjacent" to another annular support if it is the next annular support when moving towards either the first end 12 (proximal) or the second end 14 (distal). In this example, the annular supports 2022 (which may also be referred to herein as "rings") are connected to at least one adjacent support 2022 by a ring connector 2020 (S-shape ring connector). The rings 2022 may be described herein as being "connected" to adjacent rings; for ease of discussion a ring and a plurality of crosslink connectors, e.g., one or more S-shape crosslink connectors, which connect the ring to an adjacent ring may be referred to as a connecting portion. In this example, there are two S-shape crosslink connectors connecting each ring to the ring adjacent to it. The rings and the crosslink connectors are understood to be integrally formed with the rings, such as where the entire stent may be manufactured from a single piece of starting material, e.g., by laser cutting a cylindrical piece.

Each of the rings 2022 in this embodiment has a wave configuration, with a plurality of two peaks and two valleys, repeating in a pattern (only some peaks and valleys are labeled for clarity). In this embodiment, peaks of the supports 2022 may extend to the same location along the length of the stent. Valleys of supports (rings) also extend to the same location along the length of the stent. Thus, the peaks (e.g., 2024 and 2025) may be aligned along the length of the stent device, shown, and the valleys (e.g., 2024' and 2025') may also be aligned along the length of the stent. Peaks and valleys of the waves may define flattened, or squared, ends 2028. This embodiment is an example of at least one annular support with a repeating wave pattern having flattened ends connected by curvilinear intermediate sections.

In this embodiment, the annular supports all have the same configuration along the length of the stent. Two peaks 2025 produce a closed head (top) 2026, enclosing a shape with a proximal-facing opening, and two valleys 24' define the interior of a closed head (bottom) 2027, having a distal-facing opening. In some variations, not every annular support has the same configuration as every other annular support. FIG. 20B shows the inner diameter of stent 2010 is 2.53 mm and the outer diameter is 2.77 mm.

FIG. 20C illustrates an expanded, flattened/planar view of the region A of a stent device 2010 of FIG. 20A, which illustrates the connections between adjacent rings. In this embodiment, the region between two adjacent rings 2022 are connected by at least two crosslink connectors, e.g., S-connectors), and only a portion of the rings 2022 are shown. The ring connector 2020 has a "S" configuration. In this embodiment, the general "S" configuration is defined by two arcs 2031 and 2033 connected by a linear region 32. The S-shape ring connector 2020 and adjacent annular supports 2022 are connected along a lateral radius of heads (flattened tops) 2026 and 2027. The proximal part of the S-shaped ring connector 2020 connects with a downward-directed radius of the closed head 2026 however the distal part of the S-shape ring connector 2020 connects with a upward-directed radius of the bottom closed head 2027.

The "S" shape may include two arcs 2031 and 2033 connected by a midpoint (which may include a linear region and/or a point of inflexion 2032 between the two curving regions. Curves 2031 and 2033 can have slightly varying configurations and the S-shape ring connector can still have a general "S" configuration as used herein.

As can be seen in FIG. 20A, the S-shaped connectors may all have similar configurations, and may all be oriented in the same direction. Alternatively in some variations the S-shaped connectors may have different configurations (shapes, radius of curvatures for the first and second arcs, etc.), including different thicknesses. In this embodiment, each pair of adjacent supports 2022 is coupled together by two S-shaped crosslink connectors 2020, each of which has the configuration shown in FIG. 20C.

Figure 20E:
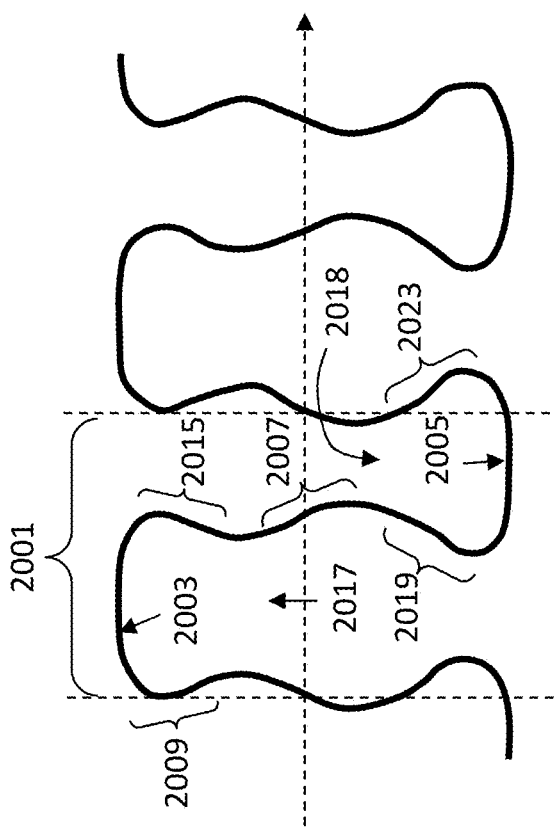
FIGS. 20D and 20E show an enlarged view of a unit cell of an exemplary apparatus such as the one shown in FIG. 20A.
Figure 20D:
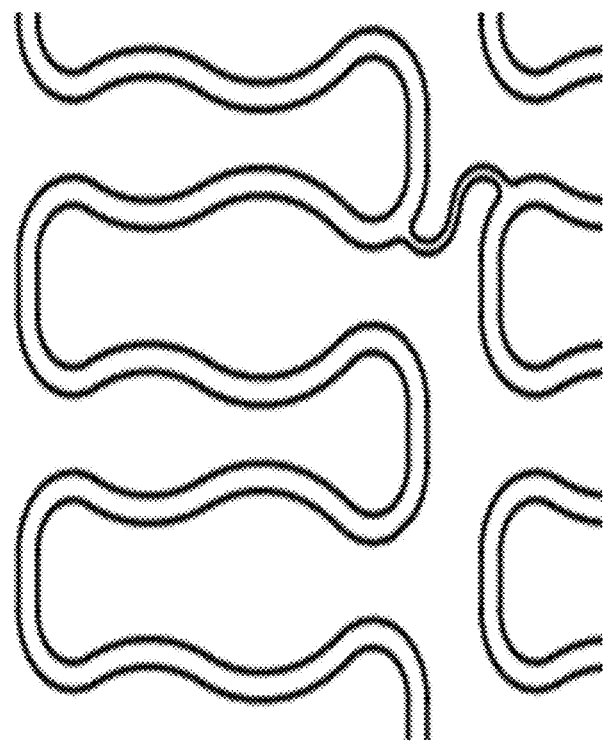

FIGS. 20D and 20E illustrate an enlarged view of a unit cell that may be repeated to form the rings of a stent such as the stent example shown in FIGS. 19C, 19F, 20A, 21, 25A, 26A, 27A, 28A, 30 and 31A. In FIG. 20E, the rings of FIG. 20A may be formed of a length of material (e.g., metallic and or polymeric material) that forms, around the radius of the stent, a pattern of repeating biphasic cells, as shown in FIG. 20E. The repeating biphasic cells 2001 typically include a pair of flattened top regions 2003, 2005 that are connected by an intermediate region 2007. In some variations the flattened top regions each form an open trapezoidal portion. In FIG. 20E, the first open trapezoidal portion includes a first side or leg 2009, a second side (corresponding to the flattened top 2003), and a third side or leg 2015. This open trapezoidal portion has a distal-facing opening 2017. Similarly, a second open trapezoidal portion, oriented 180 degrees off of the first open trapezoidal portion, includes a fourth side 2019, a fifth side (corresponding to the flattened top 2005), and a sixth side or leg 2023. The second open trapezoidal portion has a proximal-facing opening 2018. The first and second open trapezoidal portions may be connected by intermediate regions 2007. For example, the third side 2015 of the first open trapezoidal portion may be connected to the fourth side 2019 of the second open trapezoid portion by a connector region 2007, as shown, and the first side of the first open trapezoidal portion 2009 is connected to the sixth side of a second open trapezoidal portion of the next biphasic cell. The connector regions may be generally straight, and/or may be curved including s-shaped, so as to connect to the side of two trapezoidal regions.

As mentioned above, the trapezoidal regions may be referred to as trapezoidal as they have a flattened top, two generally straight sides, and an open bottom. The connections between the top and bottom may be rounded, as shown in FIG. 20E.

The first open trapezoidal portion and the second open trapezoidal portion may have different 'trapezoidal' shapes, as mentioned above. For example, in FIG. 20E, the first and second open trapezoidal shape is approximately isosceles trapezoidal, and open on one side. Both the first and second open trapezoidal portions in the exemplary biphasic cell shown in FIGS. 20D and 20E are the same general shape, although the trapezoidal portion having a proximal-facing opening has walls that are more angled relative to the flat top(s).

Figure 21:
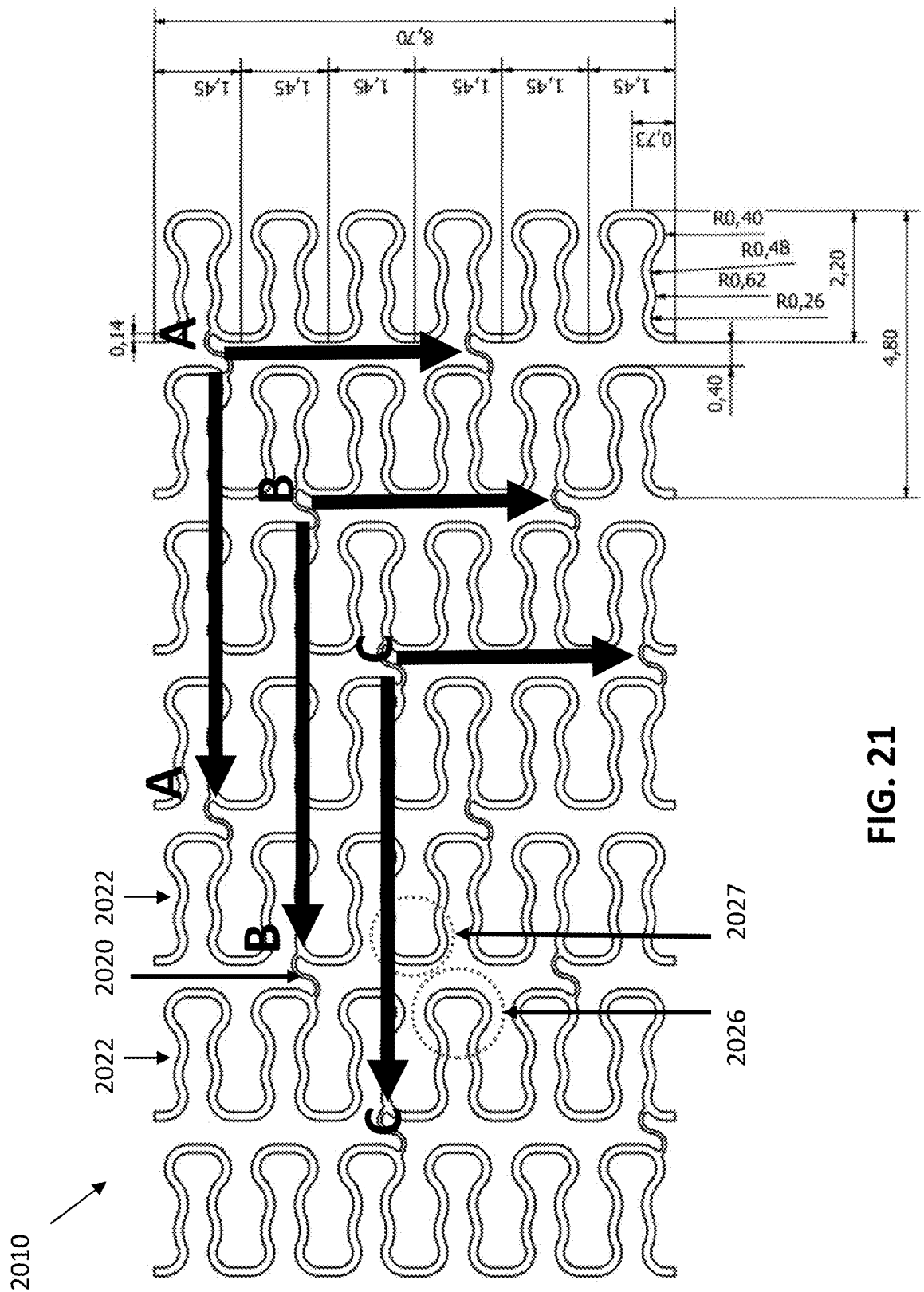
FIG. 21 shows exemplary dimensions and features of a stent apparatus according to some embodiments of the disclosure.

As can be seen in FIG. 21, the S-shaped crosslink connectors 2020 in any given connecting portion of stent 2010 are not circumferentially aligned with the connectors in the adjacent connecting portion, but they are circumferentially aligned with the connectors in the third adjacent connecting portion. In this embodiment, the position of the S-shape crosslink connectors 2020 are in an A-B-C-A-B-C pattern, with every third ring 2022 where the respective crosslink connectors are circumferentially aligned. Additionally, for stent 2010 of FIGS. 20A-20C, and FIG. 21, the unit cell high is 2.2 mm and the width are 1.45 mm.

In some variations, only three or fewer (e.g., two) connectors are used to connect adjacent rings. For example, by having only two connectors in each connecting region, there may be less area of material than in some other stent designs. This smaller area may allow the stent to have more flexibility and can expand to a greater extent when forces are applied on the stent such as by an expansion balloon. In alternative embodiments, however, there could be more than two connectors in a connecting portion, and the desired flexibility could still be maintained by modifying one or more other aspects, such as, for example without limitation, one or more dimensions (e.g., thickness, radius), configuration, or material.

The stent apparatuses described herein, an in particular, the stent apparatuses having an s-shaped connector (and in some variation the longer unit cells such as those shown in FIGS. 20A-20E) may expand to a radial diameter that is slightly larger than others. For example, in some variations, the radial expansion may be up to 12 mm or more (e.g., up to 11 mm, up to 10 mm, etc.).

Figures 22A, 22B:
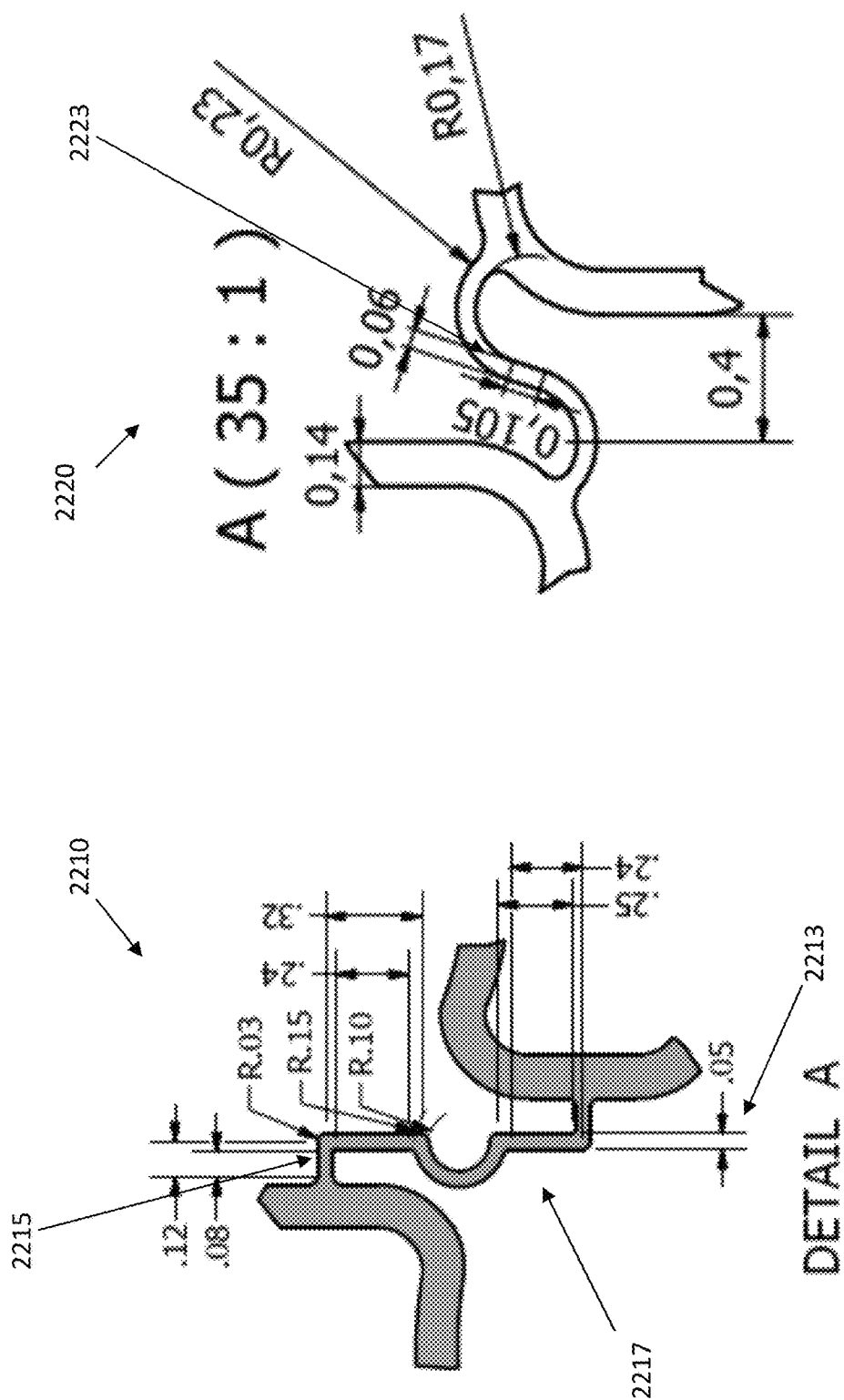
FIGS. 22A-22B show details of two examples of ring connector shapes.

FIGS. 22A and 22B compare dimensions for the respective detail region A for the device of FIGS. 19A-19B and FIG. 19C, FIGS. 20A-C, FIG. 21 respectively. In FIG. 22A, detail region 2210 shows the width 2213 of omega shaped crosslink connectors is 0.05 mm, and the length of perpendicular portion 2215 of the L-segment of the omega shape ring connector permitting perpendicular connection to the flattened bottom or flattened top is 0.12 mm. The other cross-wise portion 2217 of the L-segment is 0.32 mm. In FIG. 22B, the S-shape ring connector of the stent device of FIGS. 20A-C, FIG. 21 has a much simpler design, and the detail region 2220 shows that the S shape ring connector has a width 2223 that is 0.06 mm. The additional dimensions are described as above. For all of devices of FIG. 19A-19C. FIGS. 20A-C, FIG. 21, the width of the materials forming the unit cells is the same for all of these stent devices at 0.14 mm.

Figure 23B:
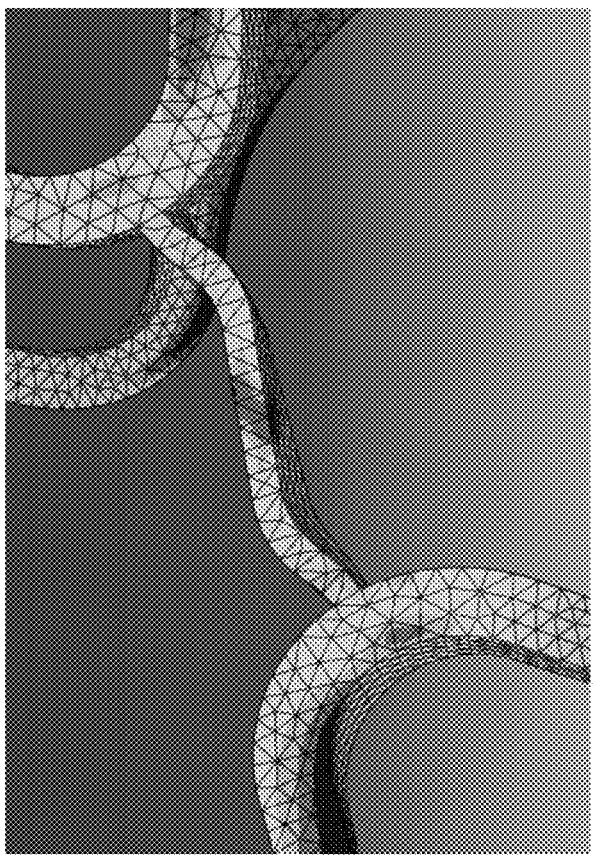
FIGS. 23A-23B show stress distributions compared between different stent apparatus having different ring connector shapes.
Figure 23A:
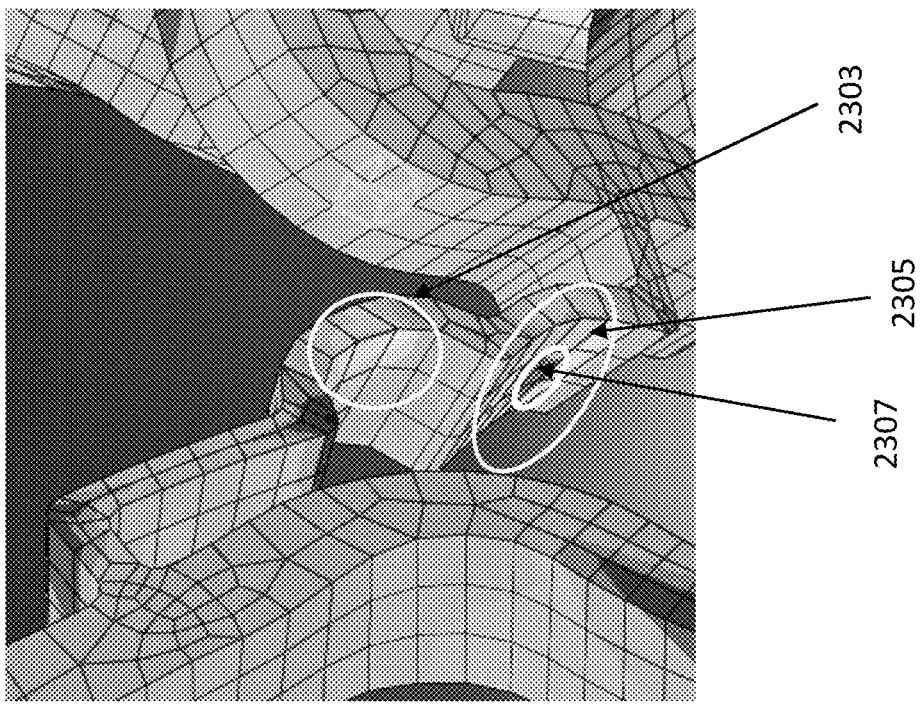

FIGS. 23A and 23B show stress distribution models for the omega-shape ring connector and the S shape ring connector respectively. In FIG. 23A, region 2303 shows a lighter colored region which indicates increased stress at the inside curve of the "omega" portion of the omega shape ring connector. A larger region 2305 on the underside of L-shaped portion of the omega curve, shows stress from torque exerted by its connection to the two rings. A central region 2307 has a more intense region of stress. In contrast, FIG. 23 B shows the S-shape ring connector. There are no regions of stress at all, and the darker colors represent lower stress than the medium coloration.

Figure 24B:
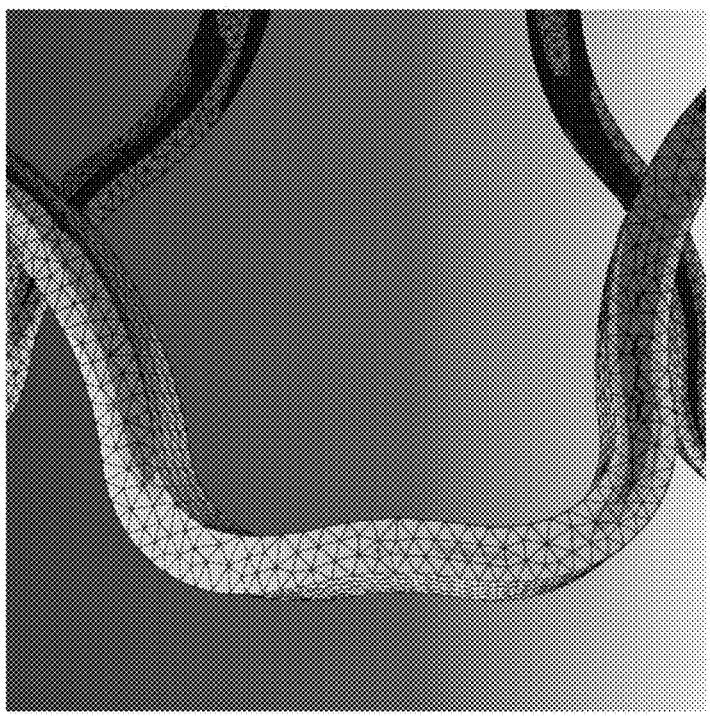
FIGS. 24A-24B show stress distributions compare between different unit cell configurations.
Figure 24A:
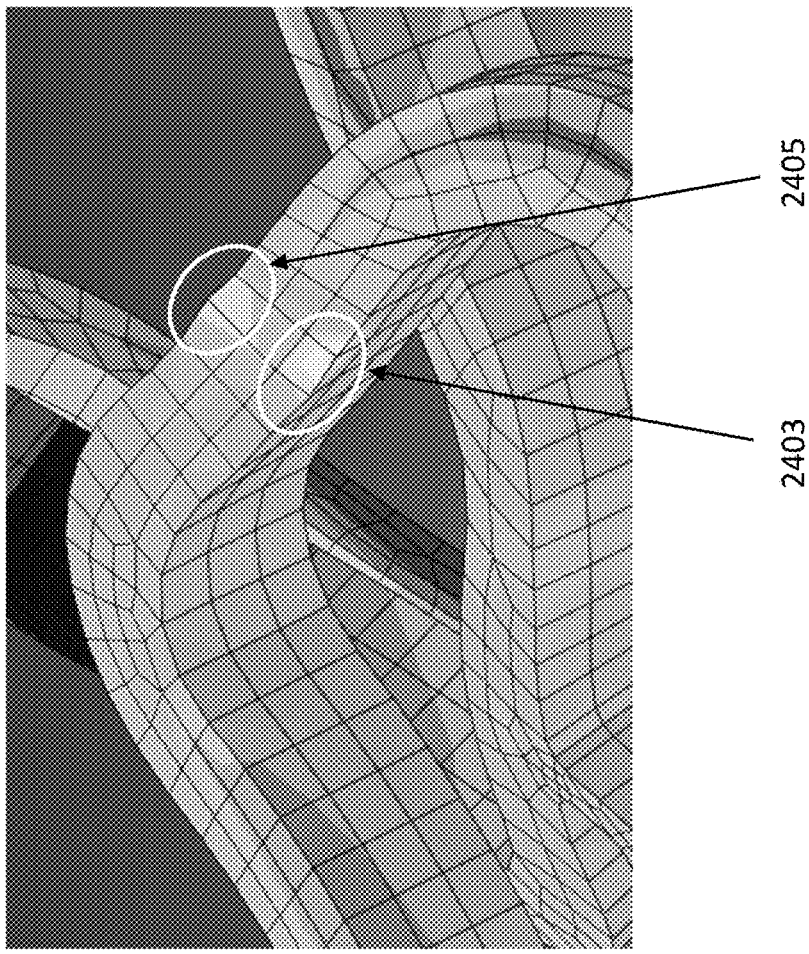

FIGS. 24A and 24B show stress distribution models for the unit cell shown of devices of FIG. 19A, 19B and FIGS. 19C, 20A-C, 21 respectively. FIG. 24A shows regions 2403 and 2405, located at the center of flattened bottoms/flattened tops of unit cells of FIG. 19A, 19B having increased stress both at the inside edge 2403 and outside edge 2405 of the feature. The area near the union between the unit cell and the omega shaped ring connector is an area where high stresses values can be observed. In the stent 1930 of FIG. 19C and other stents like it (FIGS. 20A-20C, 21, incorporating the change in the location of the connection, between the unit cell and the ring connector, eliminates stress in the unit cell.

In contrast, FIG. 23B shows a model of the flattened top/flattened bottom of the unit cell of FIG. 19C, FIGS. 20A-20C, where no stress at all develops.

FIG. 25A shows an exemplary stent device 2310 like the stent device of FIG. 19C, and has similar dimensions and features as described for device 1930, 2010. Two S-shape crosslink connectors are used to connect one ring to the ring adjacent, and span a distance of 0.4 mm. The pattern of crosslink connections is similar to device 1930, 2010, having an ABC repeat pattern, and non-offset connection between rings. The dimensions of the stent 2510 is 10 mm by 16.6 mm long. Region A of FIG. 25A is shown in greater detail in FIG. 25B and has the same dimensions of width of the material forming the unit cells (flattened top/flattened bottom) of 0.14 mm and the width of the S shape ring connector of 0.06 mm, as that of stent 1930. FIG. 25C shows the inner diameter 2513 (2.61 mm) and outer diameter 2515 (2.85 mm) of the unexpanded stent 2510.

The initial outer dimension 2515 of the stent is shown as 2.83 mm (see, e.g., FIG. 25C), as opposed to 2.76 mm in the embodiment in FIGS. 20A-B. The initial larger outer dimension allows the stent in this embodiment to be expanded to larger outer dimensions without fracturing. Another difference is the height and the width of the unit cell. As shown in FIGS. 20A-B, the unit cell high is 2.2 mm and the width are 1.45 mm however in the case of the FIGS. 25A-25C, the unit cell is 3 mm high and 1.49 mm wide.

FIGS. 26A-26C show another exemplary stent device 2610, having dimensions of 10 mm by 23.4 mm. The unit cells are similar to the unit cells of stent devices 1930, 2010 and 2510, having the same dimensions, same number of S shape crosslink connectors, distance connected across by the crosslink connectors, and pattern of ring connector location, and alignment (ABC repeat). The location of contact with the flattened bottom and flattened top is the mirror image of devices 1930, 2510, connecting from the left side of the flattened top to the right side of the flattened bottom of unit cells on each ring. FIG. 26B shows the detail region A from FIG. 26A, and shows the same dimensions for the length of material forming the unit cells and the S shape crosslink connectors as for device 1930, 2010, 2310. FIG. 26C shows the dimensions of the unexpanded stent 2610, having an inner diameter 2613 of 2.61 mm, and an outer diameter 2615 of 2.85 mm.

Figure 27A:
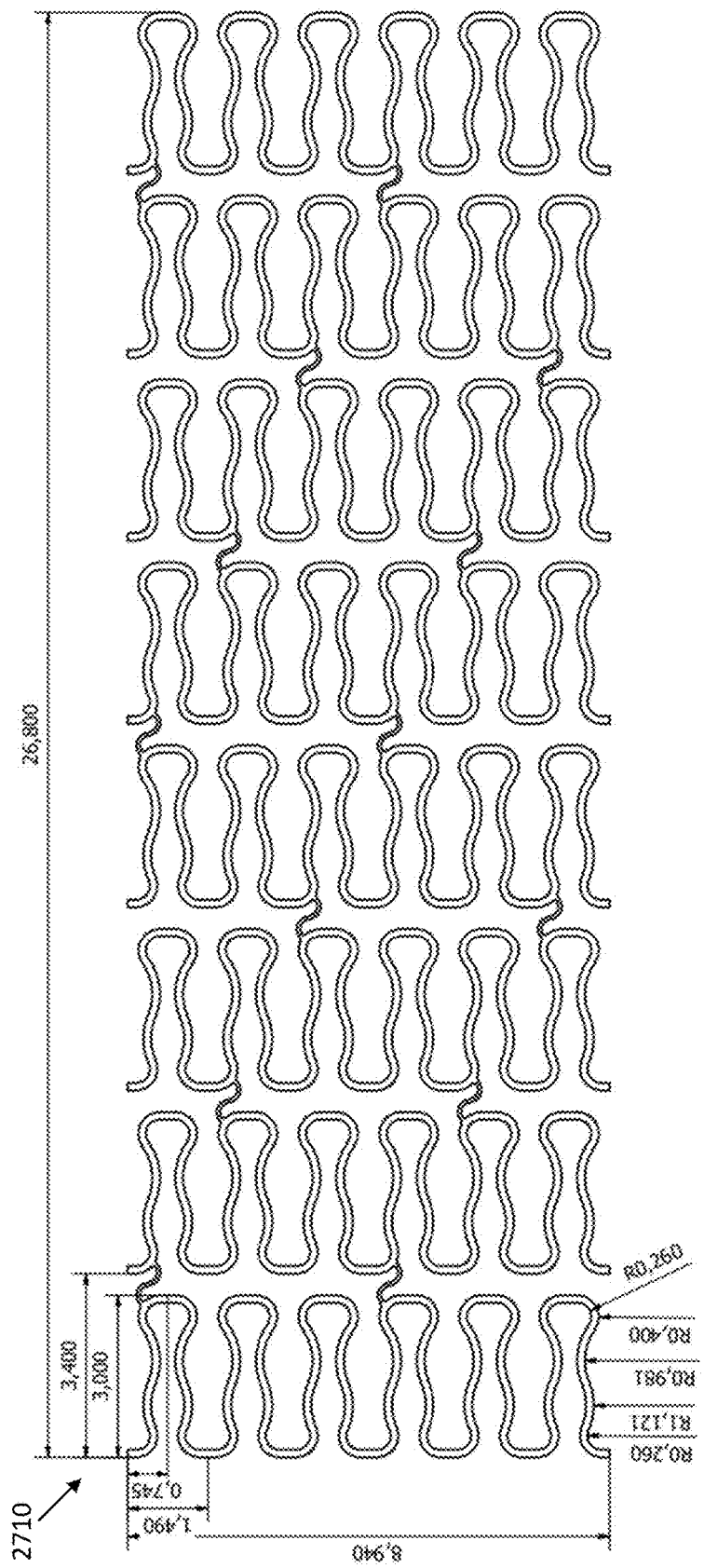
FIGS. 27A-27C show exemplary dimensions of a stent apparatus according to some embodiments of the disclosure.
Figure 27C:
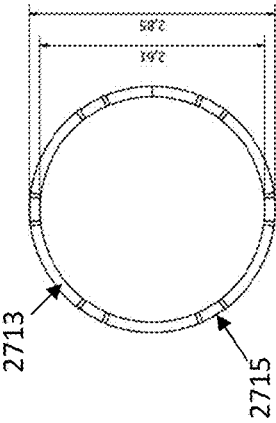
Figure 27B:
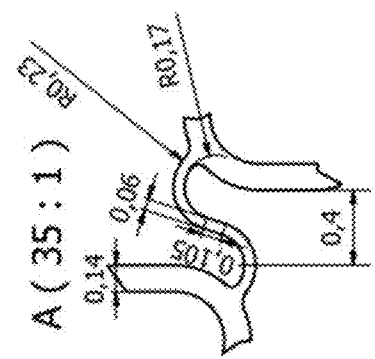

FIGS. 27A-27C show another exemplary stent device 2710, having dimensions of 10 mm by 26.8 mm long. The unit cells are similar to the unit cells of stent devices 1930, 2510, 2610, having the same dimensions, same number of S shape crosslink connectors, distance connected across by the crosslink connectors, and pattern of ring connector location, and alignment (ABC repeat). The location of contact with the flattened bottom and flattened top is the same as for stent device 2610. FIG. 27B shows the detail region A from FIG. 27A, and shows the same dimensions for the length of material forming the unit cells and the S shape crosslink connectors as for device 1930, 2510, 2610. FIG. 27C shows the dimensions of the unexpanded stent 2710, having an inner diameter 2713 of 2.61 mm, and an outer diameter 2715 of 2.85 mm.

Figure 28A:
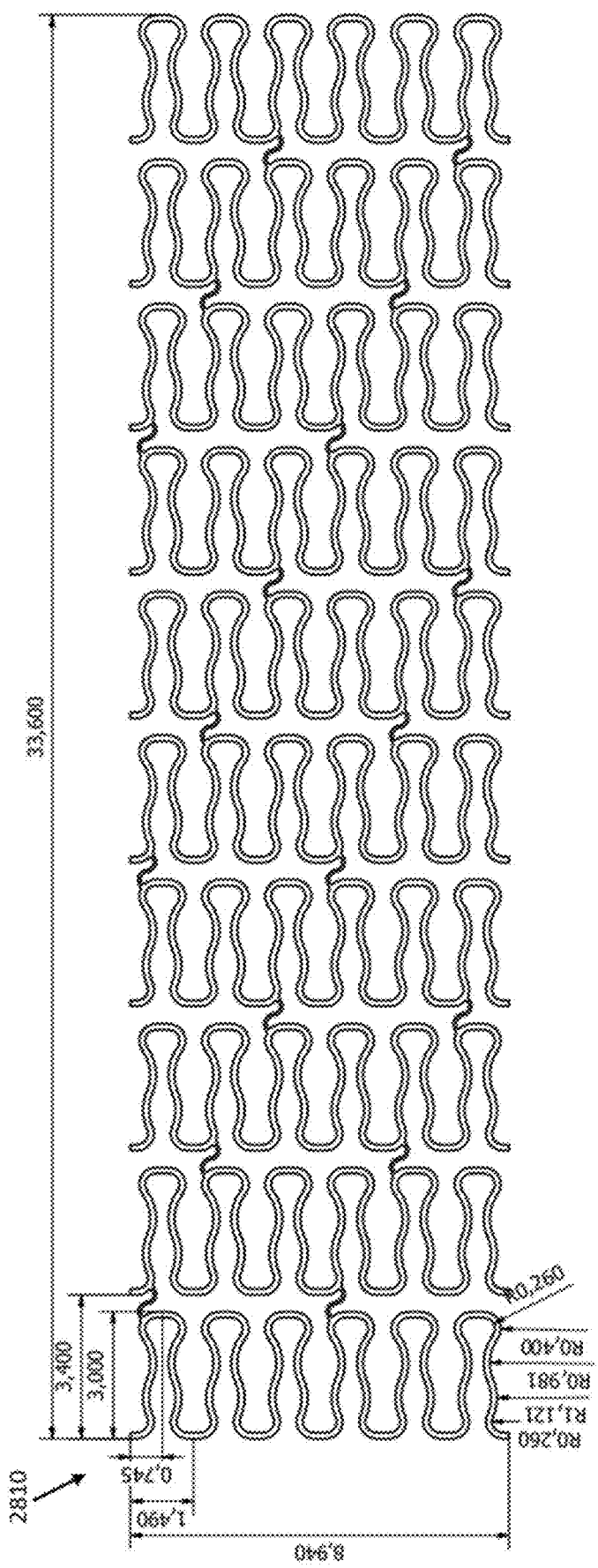
FIGS. 28A-28C show exemplary dimensions of a stent apparatus according to some embodiments of the disclosure.
Figure 28B:
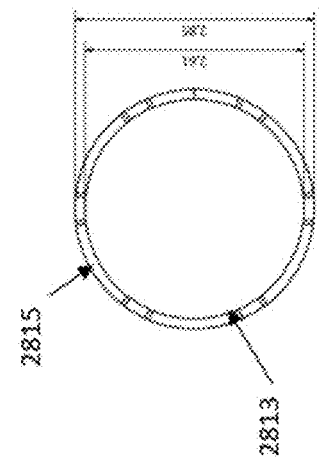
Figure 28C:
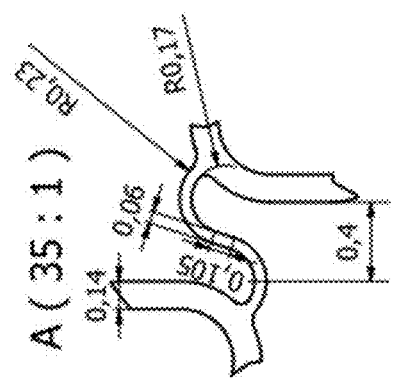

FIGS. 28A-28C show another exemplary stent device 2810, having dimensions of 10 mm by 33.6 mm long. The unit cells are similar to the unit cells of stent devices 1930, 2510, 2610, 2710 having the same dimensions, same number of S shape crosslink connectors, distance connected across by the crosslink connectors, and pattern of ring connector location, and alignment (ABC repeat). The location of contact with the flattened bottom and flattened top is the same as for stent device 2610, 2710. FIG. 28B shows the detail region A from FIG. 28A, and shows the same dimensions for the length of material forming the unit cells and the S shape crosslink connectors as for device 1930, 2510, 2610, 2710. FIG. 28C shows the dimensions of the unexpanded stent 2610, having an inner diameter 2813 of 2.61 mm, and an outer diameter 2815 of 2.85 mm.

FIGS. 29A-29C show another exemplary stent device 2910, having dimensions of 10 mm by 57.4 mm long. The unit cells are similar to the unit cells of stent devices 1930, 2510, 2610, 2710, 2810, having the same dimensions, same number of S shape crosslink connectors, distance connected across by the crosslink connectors, and pattern of ring connector location, and alignment (ABC repeat). The location of contact with the flattened bottom and flattened top is the same as for stent device 2610, 2710, 2810. FIG. 29B shows the detail region A from FIG. 29A, and shows the same dimensions for the length of material forming the unit cells and the S shape crosslink connectors as for device 1930, 2510, 2610, 2710, 2810. FIG. 29C shows the dimensions of the unexpanded stent 2910, having an inner diameter 2913 of 2.61 mm, and an outer diameter 2915 of 2.85 mm.

Figure 30:
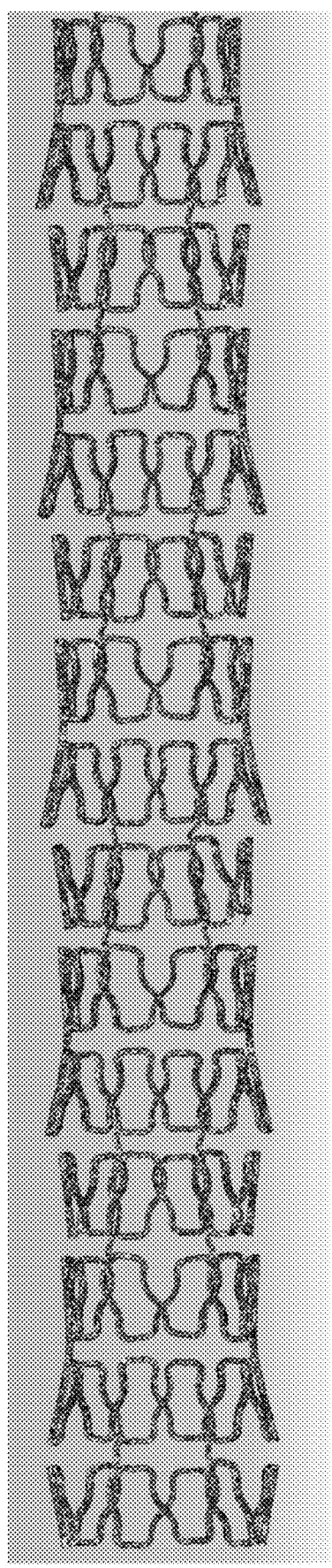
FIG. 30 shows a finite element model (FEM) simulation of a stent apparatus.

FIG. 30 shows a finite-element simulation of stent expansion for the stent 2910 of FIGS. 29A-29C, having expanded dimensions of 10 mm by 57.4 mm long.

Figure 31A:
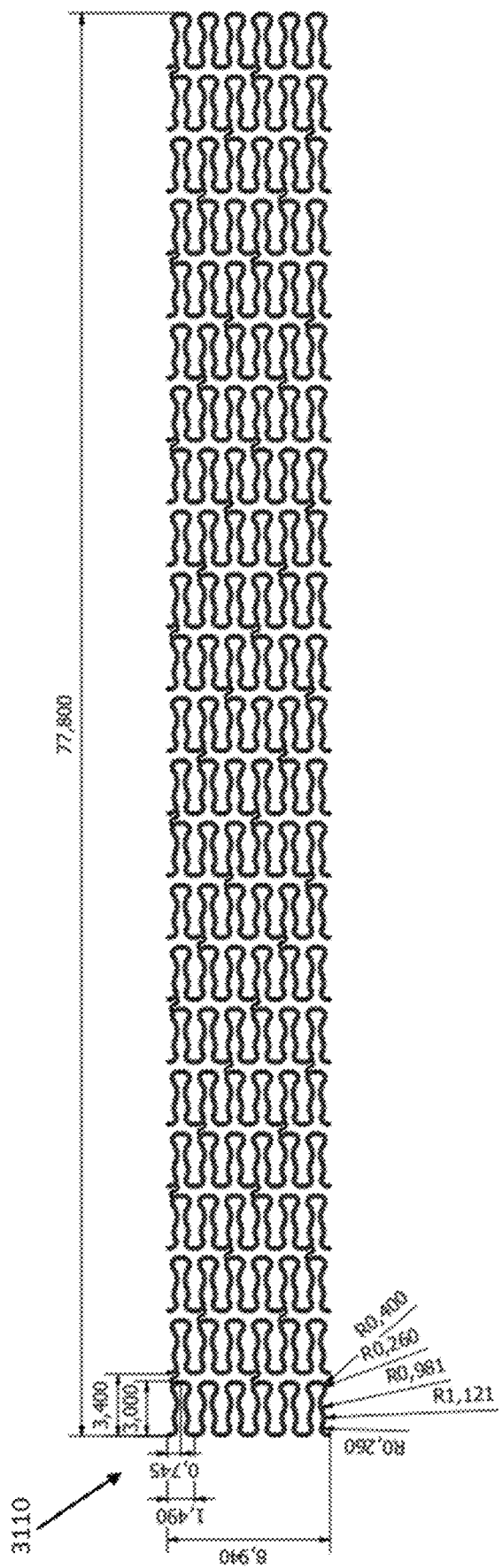
FIGS. 31A-31C show exemplary dimensions of a stent apparatus according to some embodiments of the disclosure.
Figure 31B:
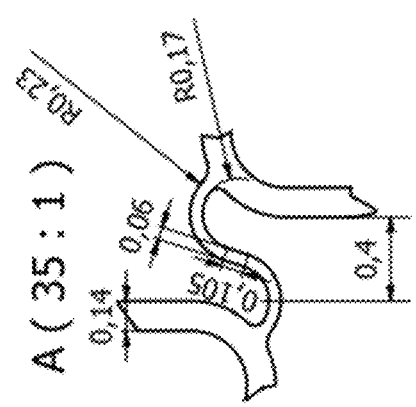
Figure 31C:
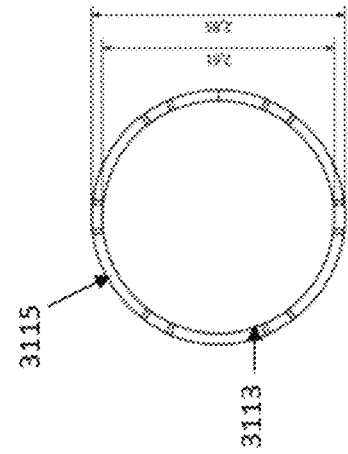

FIGS. 31A-31C show another exemplary stent device 3110, having dimensions of 10 mm by 77.8 mm long. The unit cells are similar to the unit cells of stent devices 1930, 2510, 2610, 2710, 2710. 2910, having the same dimensions, same number of S shape crosslink connectors, distance connected across by the crosslink connectors, and pattern of ring connector location, and alignment (ABC repeat). The location of contact with the flattened bottom and flattened top is the same as for stent device 2610, 2710, 2810, 2910. FIG. 31B shows the detail region A from FIG. 31A, and shows the same dimensions for the length of material forming the unit cells and the S shape crosslink connectors as for device 1930, 2510, 2610, 2710, 2610, 2810. FIG. 31C shows the dimensions of the unexpanded stent 3110, having an inner diameter 3113 of 2.61 mm, and an outer diameter 3115 of 2.85 mm.

Performance Testing

In general, the biphasic arrangement of trapezoidal unit cells forming each ring of the stent, as well as the configuration and arrangement of the s-shaped connectors connecting adjacent rings of the stent, may allow these devices to expand while maintaining their radial compression strength and longitudinal compression strength with a minimal recoil and stent foreshortening. FIGS. 32A-36 illustrate the result of performance testing of the stents described herein and comparisons with other (e.g., prior art) stents. The results show an improvement in performance for all sizes of the improved stents described herein as compared to prior art stents of comparable sizes. This testing was done to ISO standards, such as ISO 25539.

A variety of differently-sized stents having a plurality of rings formed of biphasic open trapezoidal shapes (alternating distal-facing and proximal-facing trapezoidal shapes), such as shown in FIGS. 20A-20E, 21, 22B, 23B, 25A-31C, in which the rings are connected by s-shaped connectors in a helical pattern were characterized and compared to each other as well as to known stents (such as the GORE TIGRIS vascular stent, BARD LIFESTENT Vascular stent, CORDIS S.M.A.R.T CONTROL stent, COVIDIEN PROTÉGÉ EVERFELX stent, Abbott ABSOLUTE PRO LL vascular stent, OptiMed SINUS-SUPERFLEX stent, COOK ZILVER PTX stent, and IDEV SUPERA stent).

Figure 37A:
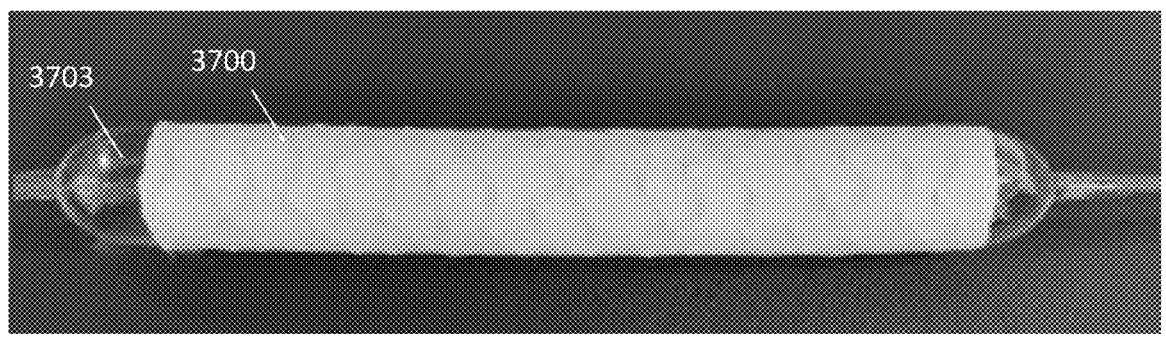
FIGS. 37A-37C illustrate one example of a stent as described herein, including a sleeve encapsulating the rings.
Figure 37B:
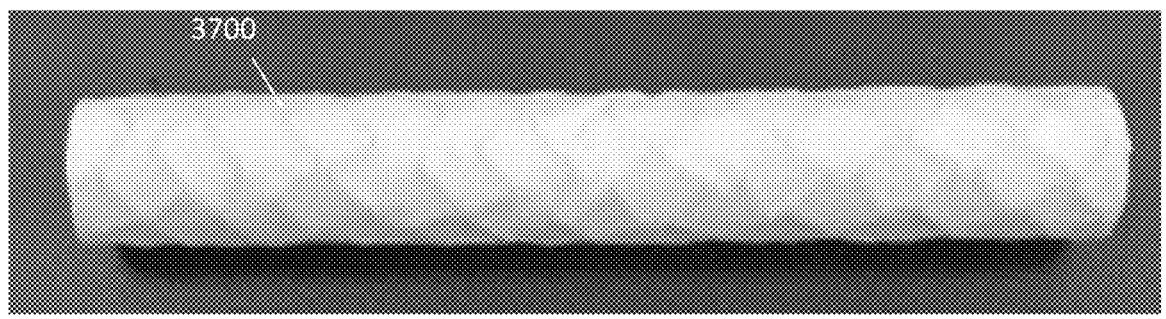
Figure 37C:
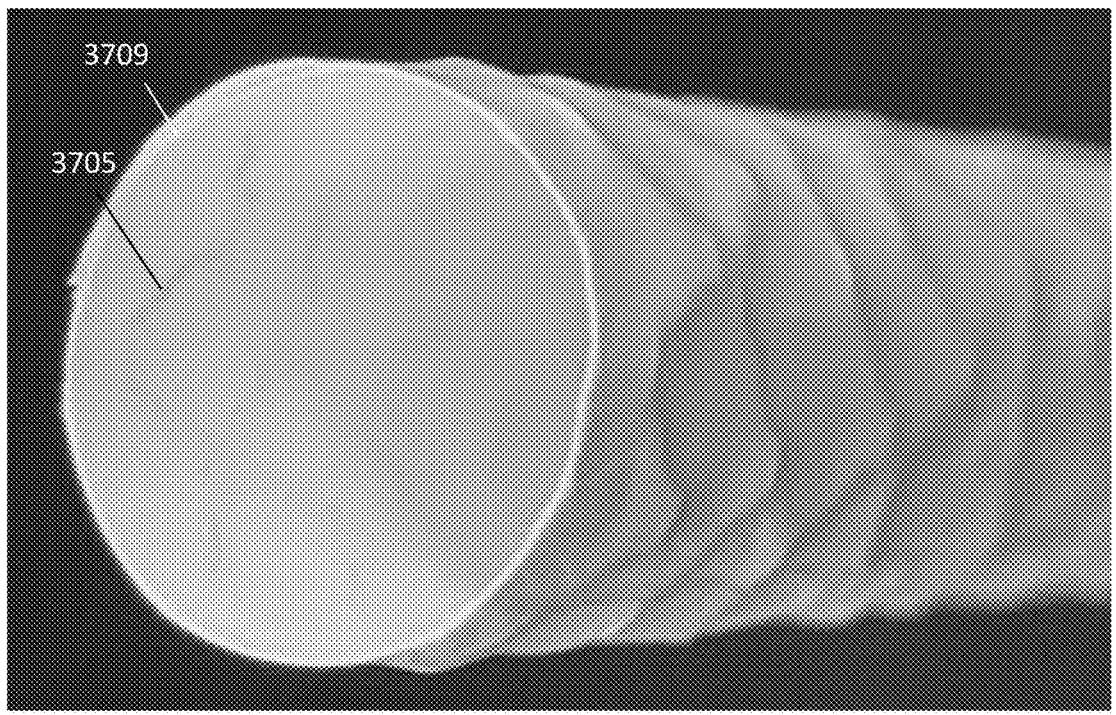

FIGS. 37A-37C illustrate an example of a stent 3700 similar to that shown in FIGS. 20A-20E, 21, 22B, 23B, 25A-31C, described above. In the example of a stent shown in FIG. 37A, the stent 3700 is expanded into the second configuration by the expansion of a balloon 3703. The stent includes a plurality of rings 3705 that are adjacent to each other and connected by s-shaped connectors; in FIGS. 37A-37C the stent is covered by a sleeve 3709 (e.g., graft) material. The rings are arranged transverse to the length (distal-to-proximal length) of the stent. The plane of each ring is transverse and perpendicular to the length. Each ring is formed of a repeating pattern of alternating flattened tops and flattened bottoms extending transverse to the length of the device, wherein the flattened tops are connected to the flattened bottoms by sigmoid-shaped region (connector) so that each flattened top forms part of a proximal-facing U-shape and each flattened bottom forms part of a distal-facing U-shape. The top, bottom and sigmoid-shaped regions are all continuous regions of the same length of material (e.g., wire, laser-cut tube, etc.). These shapes may also be described as a plurality of repeating biphasic cells, in which each biphasic cell includes a first open trapezoidal portion having a first side, a second side (e.g., top), and a third side forming a proximal-facing opening, and a second open trapezoidal portion having a fourth side, a fifth side (e.g., bottom) and a sixth side forming a distal-facing opening. The second side and the fifth side may be arranged in parallel (e.g., the top and bottom may be transverse to the length of the stent in the relaxed configuration). The first open trapezoidal portion is radially offset from the second open trapezoidal portion and the third side of the first open trapezoidal portion is connected to the fourth side of the second open trapezoidal portion by a first connector region. The first side, fourth side and connector region correspond to the sigmoidal connector. The first side of the first open trapezoidal portion connects to a sixth side of an adjacent biphasic cell in the ring by a second connector, so that the biphasic trapezoidal pattern repeats to form the ring.

The s-shaped connectors connecting adjacent rings, as described above, may connect a region between one of the flattened tops and one of the sigmoid-shaped connectors (e.g., between a first and second side) on one of the rings to a region between one of the fattened bottoms and one of the sigmoid-shaped connectors (e.g., between a fourth and fifth side) on an adjacent ring.

The stents described herein may be formed of a metallic and/or polymeric material. For example, in some variations the stent may be formed of a Co—Cr Alloy (e.g., L605) which may be coated/covered with a sleeve of graft material (e.g., PTFE, such as "BIOWEB") that may be electrospun coated, e.g., to an average weight of between about 10 g/m² and 15 g/m². The diameter (e.g., outer diameter, OD) may be between 5 mm and 10 mm (e.g., between about 6-7 F) and may have a length of between about 18 mm and 59 mm. The crimped profile may be small (e.g., approximately 2 mm), and the stent may have a high retention force and high flexibility, even when coated on both the inside and outside with the graft material (e.g., PTFE). Without the particular configuration of the rings and crosslink connectors (e.g., s-shaped connectors) described herein, these properties may be difficult or impossible to achieve.

Figure 32A:
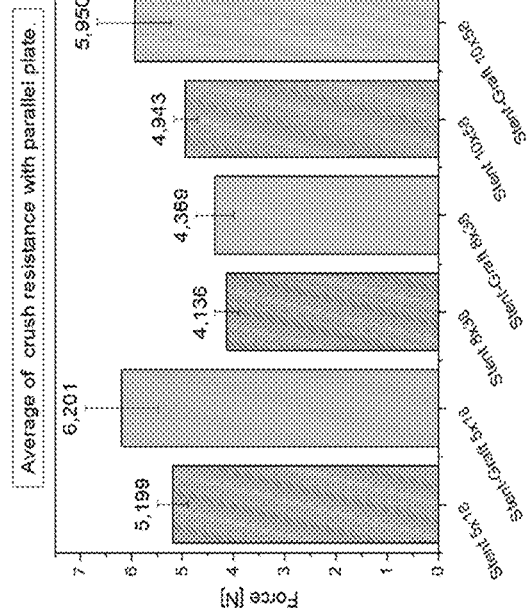
FIGS. 32A-32B illustrate the results of radial compression testing of three examples of stents (with or without graft material on the stent) having a plurality of adjacent rings formed of alternating flattened tops and flattened bottoms that are transverse to the length of the device and are connected by sigmoid-shaped connectors aligned in a helically winding arrangement around the length of the device as described herein (e.g., FIGS. 20A-20E, 21, 22B, 23B, 25A-31C).
Figure 32B:
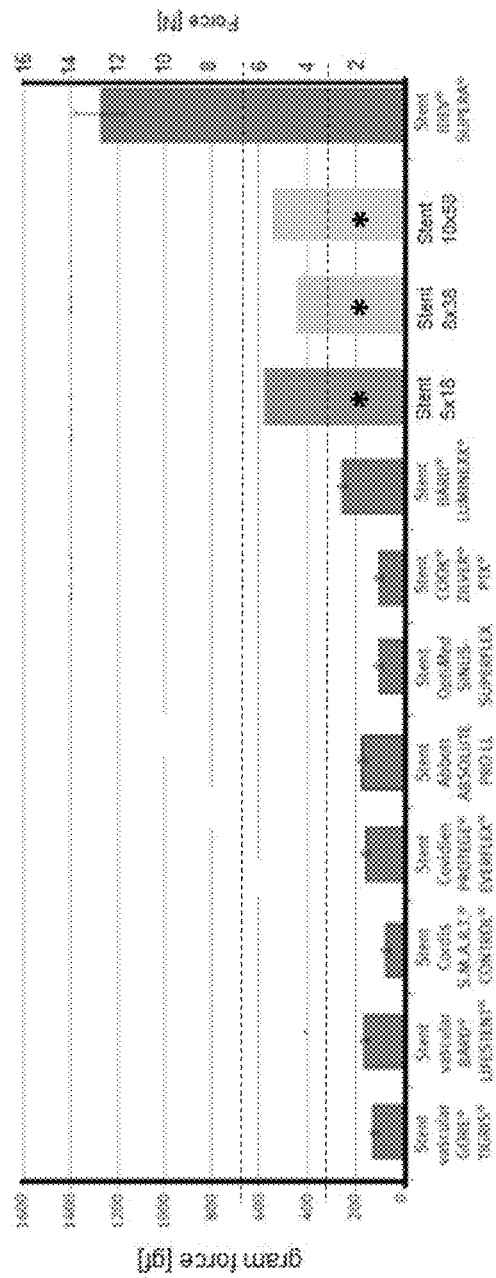

Thus, the arrangement of the stent components, and in particular the combination of shapes forming the rings and the s-shaped connectors, may provide a stent with advantageous properties as compared to other configurations, including more traditional prior art stents. For example, the radial compressive properties may be superior, providing a high crush strength. For example, FIG. 32A shows the results of radial compression testing on three different sizes (5×18 mm, 8×38 mm and 10×58 mm), with and without a graft (e.g., sleeve) of the improved stent described herein, and shown generally in FIGS. 20A-20E, 21, 22B, 23B, 25A-31C, above. The average crush resistance is estimated by the necessary force to provide some percentage (e.g., 25%, 50%, etc.) of radial compression. In these examples the radial compression testing (e.g., performed between parallel plates) showed an average of crush resistances (radial stiffness) that was between about 3N (e.g., about 3.1 N, about 3.5 N, etc.) or about 300 grams force (gf) (e.g., about 310 gf, about 350 gf, etc.) and about 6.5 N (e.g., about 6.2 N, about 6.0 N, about 5.9 N, etc.) or about 650 gf (e.g., about 620 gf, about 600 gf, about 590 gf, etc.) to cause 25% radial compression. This range may provide advantages in compressing without kinking (see, e.g., FIGS. 16A-16B, described above), or reducing the diameter less than 2 mm, while still remaining highly flexible and compliant. In comparison, prior art devices, as shown in FIG. 32B in the same radial compression testing had a necessary force to radial compression (e.g., necessary force to 25% radial compression, per ISO 25539 testing) that was substantially less than this range (e.g., less than about 3 N for the GORE TIGRIS vascular stent, BARD LIFESTENT Vascular stent, CORDIS S.M.A.R.T CONTROL stent, COVIDIEN PROTEGE EVERFELX stent, Abbott ABSOLUTE PRO LL vascular stent, OptiMed SINUS-SUPERFLEX stent, COOK ZILVER PTX stent and BARD LUMINEXX stent) or much higher than this range (e.g., greater than 10 N for the IDEV SUPERA stent). In FIG. 32B, the lower values typically represent lower radial stiffness, while the higher values represent higher radial stiffness.

Figure 33A:
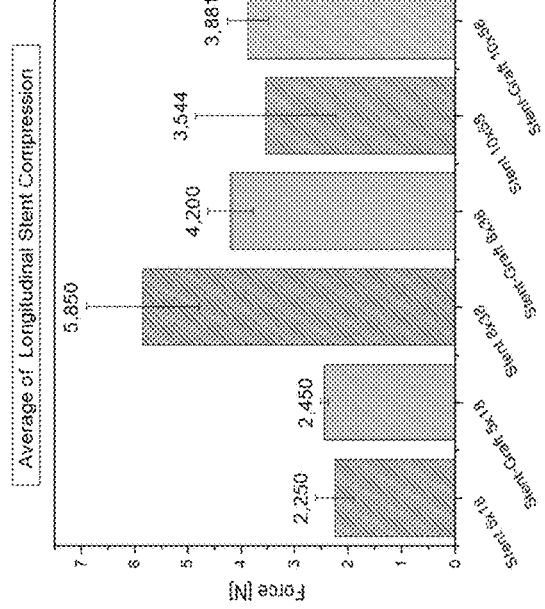
FIGS. 33A-33B shows the results of longitudinal compression testing of three examples of stents (with or without graft material on the stent) having a plurality of adjacent rings formed of alternating flattened tops and flattened bottoms that are transverse to the length of the device and are connected by sigmoid-shaped connectors aligned in a helically winding arrangement around the length of the device as described herein (e.g., FIGS. 20A-20E, 21, 22B, 23B, 25A-31C).
Figure 33B:
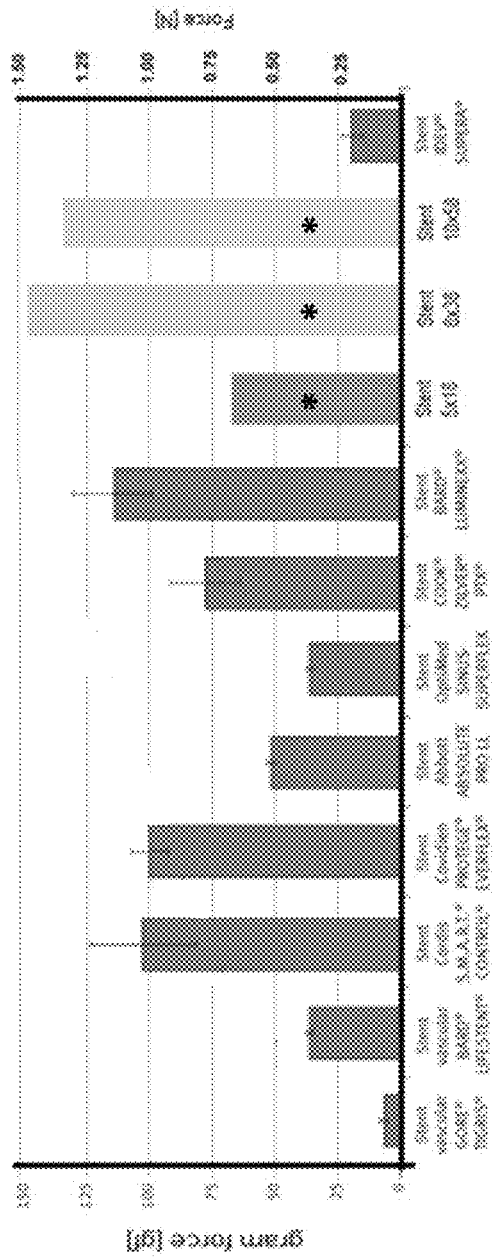

Similar testing for longitudinal compression is shown in FIGS. 33A and 33B. In this example, the same stent designs and sizes tested in FIG. 33A were examined to determine average longitudinal stent compression. The graph in FIG. 33A represents the necessary force to cause 15% longitudinal compression following standard (ISO 25539) testing. FIG. 33B shows a comparison to the same prior art stents described in FIG. 32B. The lower values represent a lower compression force while higher values show a higher compression force. The longitudinal compression forces for the stents described herein (shown by "*" for 5×18 mm, 8×38 mm and 10×58 mm stents in FIG. 33B) are comparable to those of the prior art stents tested (having similar ranges of lengths).

Figures 34A, 34B:
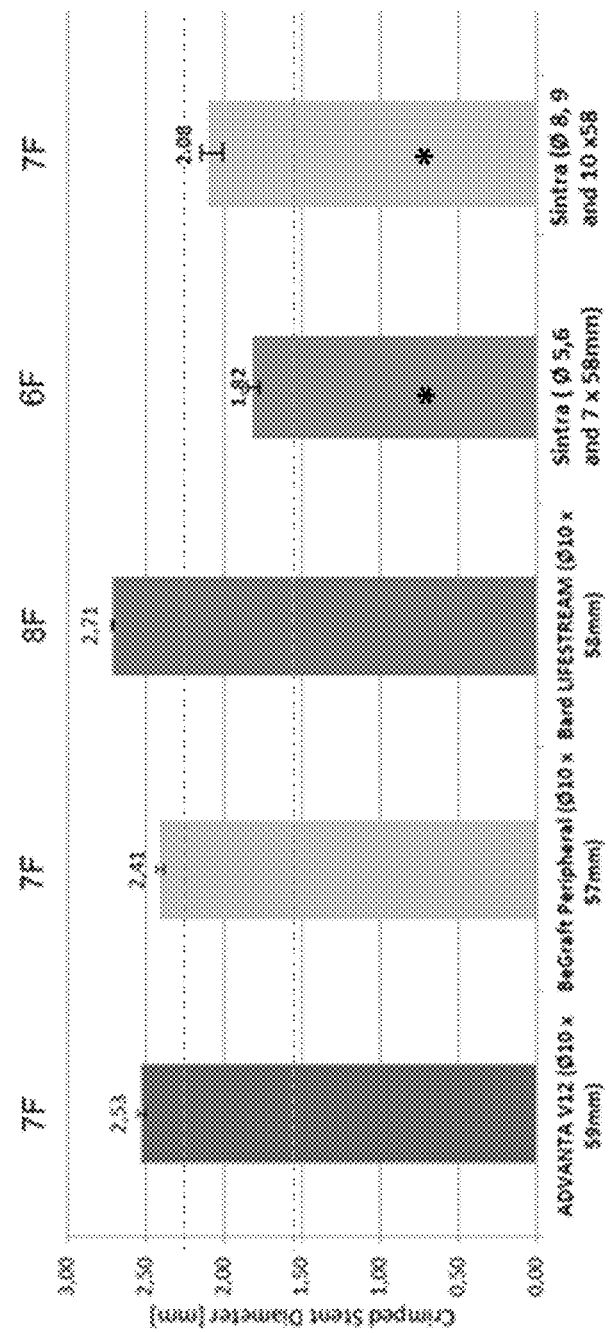
FIGS. 34A and 34B illustrate the results of performance testing for crimped testing (e.g., crimped stent profile testing).

The crimping and expanding of the stents described herein were also examined and compared to prior art stents. As shown in FIGS. 34A-34B, the stents described herein (e.g., 5×18 mm, 8×38 mm, and 10×58 mm) all showed stent crimp profiles that were equivalent or superior to those of prior art stents (see, FIG. 34B), having a crimp stent diameter of less than about 2.25 mm (e.g., less than 2.2 mm, less than 2.15 mm, less than 2.10 mm, etc.) and greater than about 1.5 mm (e.g., 1.7 mm 1.8 mm, etc.). Thus, the improved stents described herein may be crimped down onto a balloon for later expansion at narrower diameters while expanding to equivalent diameters with relatively low force.

Figures 35A, 35B:
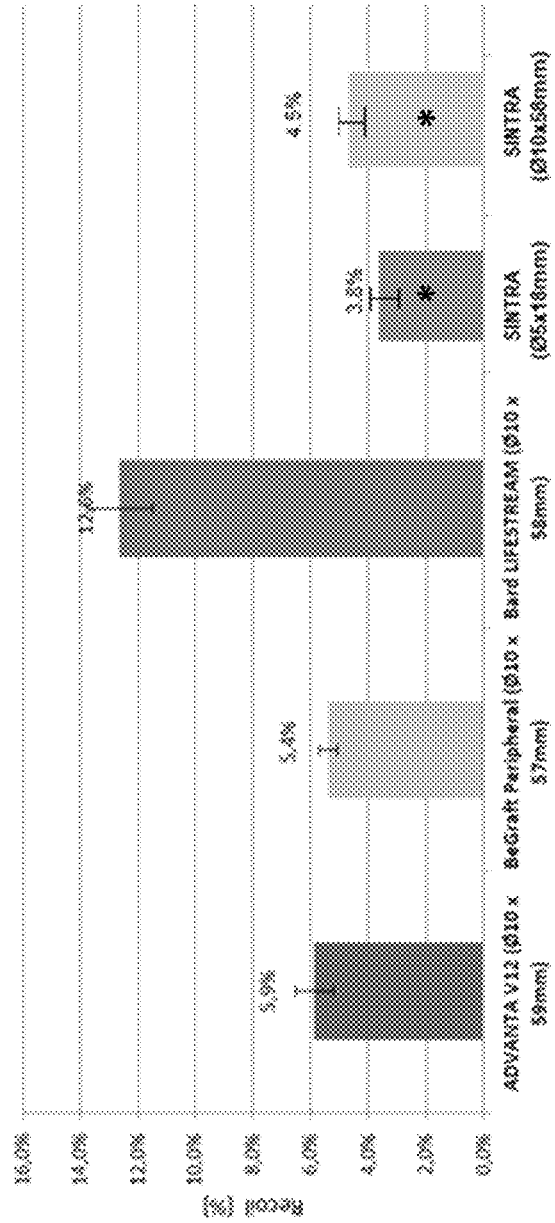
FIGS. 35A and 35B illustrate the results of performance testing for recoil (e.g., recoil testing).

In addition, the stents described herein (e.g., as shown in FIGS. 20A-20E, 21, 22B, 23B, 25A-31C, and 37A-37C) typically have a much lower stent recoil following balloon expansion than prior art stents. This was tested for different dimensions of the stents described herein, including 5×18 mm and 10×58 mm stents, as shown in the table of FIG. 35A. FIG. 35B illustrates the formula for calculating the percentage of stent recoil (e.g., the difference between the inflated outer diameter and the final outer diameter divided by the inflated outer diameter, expressed as a percentage). In FIG. 35B the percent recoil of these new (indicated by "*") stents of different dimensions is shown compared to a typical range of prior art stents. The percent stent recoil for the new stents is less than 5% (e.g., less than 4.8%, less than 4.6%, etc.), which may be advantageous in maintaining placement and stability when using the stent.

Figure 36:
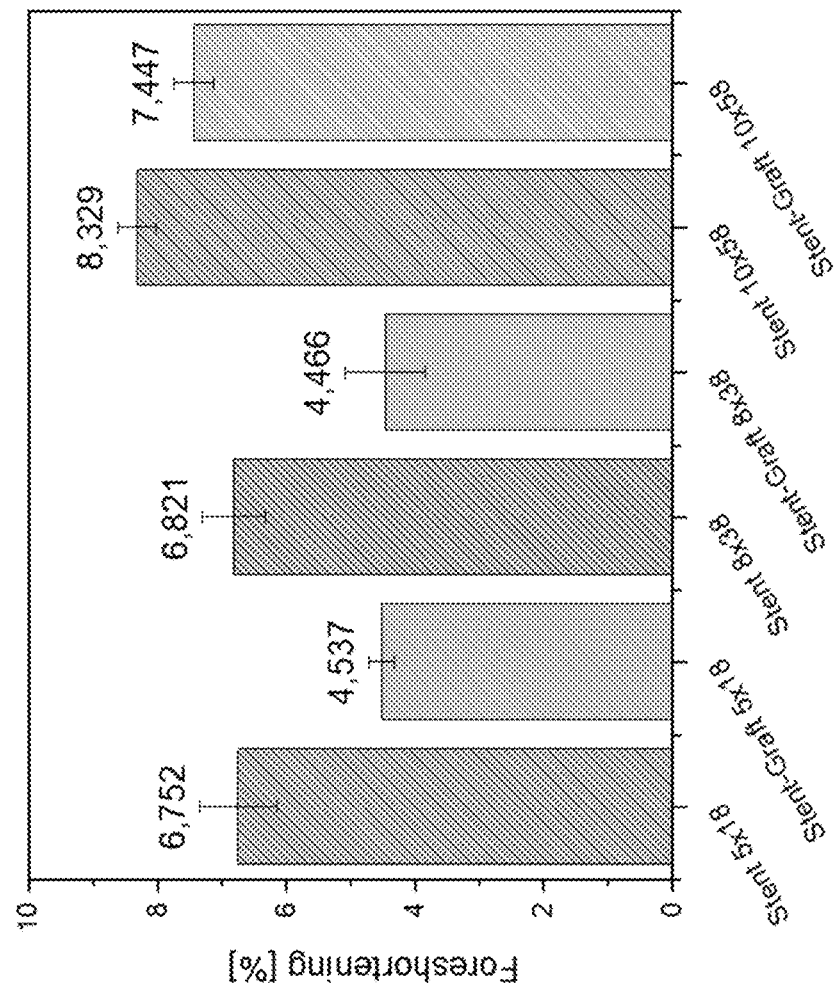
FIG. 36 is a graph illustrating the stent foreshortening of the stent configurations described herein.

Similarly, the improved stents described herein (e.g., as shown in FIGS. 20A-20E, 21, 22B, 23B, 25A-31C, and 37A-37C) have a relatively low percent of stent foreshortening from the compressed (crimped) to the expanded configuration, as graphically illustrated in FIG. 36. FIG. 36 also shows the equation for estimating percent foreshortening (e.g., the difference between crimped stent length and expanded stent length, divided by the crimped stent length, and expressed as a percentage). In general, the percent foreshortening was less than 8.5% (e.g., less than about 8.4%). This also compares favorably to existing prior art stents, which may shorten more when transitioning between crimped and expanded configurations, resulting in a less predictable and stable implantation into the vessel.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the disclosure. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present disclosure.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

In general, any of the apparatuses and methods described herein should be understood to be inclusive, but all or a sub-set of the components and/or steps may alternatively be exclusive, and may be expressed as "consisting of" or alternatively "consisting essentially of" the various components, steps, sub-components or sub-steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the disclosure as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the disclosure as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. A stent device, the device comprising:
  a plurality of adjacent rings arranged transverse to a length of the device in a proximal to distal direction, wherein each ring comprises a repeating pattern of alternating flattened tops and flattened bottoms extending transverse to the length of the device, wherein the flattened tops are connected to the flattened bottoms by sigmoid-shaped intermediate sections so that each flattened top forms part of a proximal-facing U-shape and each flattened bottom forms part of a distal-facing U-shape;
  a plurality of crosslink connectors connecting adjacent rings, wherein each crosslink connector connects a middle region of one of the flattened tops to a middle region of one of the flattened bottoms on an adjacent ring;

wherein the crosslink connectors form a helically winding arrangement around the length of the device, further wherein the cross-link connectors comprises: omega-shaped crosslink connectors having trans-configured L-shaped segments at each end; and wherein the stent device has a first configuration in which the plurality of adjacent rings has a first diameter, and the stent device has a second configuration in which the plurality of adjacent rings has a second diameter that is greater than the first diameter, and wherein the flattened tops and the flattened bottoms are configured to remain parallel to each other as the stent device is expanded from the first configuration to the second configuration.

2. The device of claim 1, wherein the repeating pattern of alternating flattened tops, flattened bottoms, and sigmoid-shaped intermediate sections comprises a repeating pattern of biphasic cells, wherein each biphasic cell includes a first open trapezoidal portion having a first side, a second side and a third side forming an opening of the proximal-facing U-shape and a second open trapezoidal portion having a fourth side, a fifth side and a sixth side forming an opening of the distal-facing U-shape, wherein the second side forms one of the flattened tops and the fifth side forms one of the flattened bottoms.

3. The device of claim 1, wherein each ring of the plurality of adjacent rings is connected by between 1 and 3 crosslink connectors extending between the rings.

4. The device of claim 1, wherein each of the crosslink connectors connecting the plurality of adjacent rings is oriented in the same direction.

5. The device of claim 1, further comprising a maximum of 2 crosslink connectors between adjacent rings.

6. The device of claim 1, wherein the flattened tops of each ring are radially offset from the flattened bottoms.

7. The device of claim 6, wherein the radial offset is configured to increase as the stent device transitions from the first configuration to the second configuration.

8. The device of claim 1, wherein the first diameter is between 0.5 mm and 4 mm and the second diameter is between 2 mm and 12 mm.

9. The device of claim 1, wherein the length of the device is between about 12 mm and about 80 mm.

10. The device of claim 1, wherein the device comprises one or more of: an alloy of chromium cobalt, a stainless steel and a magnesium alloy.

11. The device of claim 1, further comprising a sleeve comprising a polymeric matrix in which the plurality of rings are encapsulated.

12. The device of claim 11, wherein the sleeve comprises a porous material.

13. The device of claim 1, wherein the flattened tops and the flattened bottoms comprise rounded edges.

14. The device of claim 1, wherein the device is configured to foreshorten less than about 8.5% when expanding from the first configuration to the second configuration.

15. The device of claim 1, wherein the stent device is configured to bend at least 90 degrees in the first configuration without kinking.

16. A stent device having a length extending in a distal to proximal direction, the device comprising:
a plurality of adjacent rings arranged transverse to the length of the device, wherein each ring comprises a length of material arranged radially around the length of the stent device as a plurality of repeating biphasic cells, each biphasic cell comprising a first open trapezoidal portion having a first side, a second side and a third side forming a proximal-facing opening, and a second open trapezoidal portion having a fourth side, a fifth side and a sixth side forming a distal-facing opening, wherein the second side and the fifth side are parallel, further wherein the first open trapezoidal portion is radially offset from the second open trapezoidal portion and the third side of the first open trapezoidal portion is connected to the fourth side of the second open trapezoidal portion by a first connector region, and wherein the first side of the first open trapezoidal portion connects to a sixth side of an adjacent biphasic cell in the ring by a second connector;

between one and three s-shaped crosslink connectors connecting each ring that is adjacent to a more distal ring to the more distal ring, wherein each s-shaped crosslink connector connects between the first side and the second side of one of the first open trapezoidal portions of the plurality of biphasic cells in the ring that is adjacent to the more distal ring to between the fifth side and sixth side of one of the second open trapezoidal portions of the plurality of biphasic cells of the more distal ring, wherein the device has a first configuration in which a first diameter of the plurality of adjacent rings is between 0.5 mm and 4 mm, and a second configuration in which a second diameter of the plurality of adjacent rings is between 2 mm and 12 mm, and wherein the second sides and the fifth sides of the plurality of adjacent rings are configured to remain parallel as the stent device expands from the first configuration to the second configuration.

17. The device of claim 16, wherein the first and third sides are parallel in the first configuration.

18. The device of claim 16, wherein each of the s-shaped crosslink connectors connecting the plurality of adjacent rings are oriented in the same direction.

19. The device of claim 16, further comprises a sleeve comprising a polymeric matrix in which the plurality of rings are encapsulated in a sandwich configuration.

20. The device of claim 16, wherein the first, second, third, fourth, fifth, and sixth sides comprise rounded edges.

21. The device of claim 16, wherein the device is configured to foreshorten less than about 4.5-8.5% when expanding from the first configuration to the second configuration.

22. The device of claim 16, wherein each s-shaped crosslink connector has a width that is smaller than a width of a length of material forming the biphasic cells.

* * * * *